(12) United States Patent
Lovley et al.

(10) Patent No.: US 12,320,802 B2
(45) Date of Patent: Jun. 3, 2025

(54) MICROBIAL NANOWIRES MODIFIED TO CONTAIN PEPTIDES AND METHODS OF MAKING

(71) Applicant: University of Massachusetts, Boston, MA (US)

(72) Inventors: Derek R. Lovley, Amherst, MA (US); Toshiyuki Ueki, Amherst, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 855 days.

(21) Appl. No.: 17/440,632

(22) PCT Filed: Mar. 20, 2020

(86) PCT No.: PCT/US2020/023824
§ 371 (c)(1),
(2) Date: Sep. 17, 2021

(87) PCT Pub. No.: WO2020/191281
PCT Pub. Date: Sep. 24, 2020

(65) Prior Publication Data
US 2023/0160885 A1   May 25, 2023

Related U.S. Application Data

(60) Provisional application No. 62/821,208, filed on Mar. 20, 2019.

(51) Int. Cl.
*G01N 33/543* (2006.01)
*C07K 14/195* (2006.01)

(52) U.S. Cl.
CPC ....... *G01N 33/5438* (2013.01); *C07K 14/195* (2013.01); *C07K 2319/42* (2013.01)

(58) Field of Classification Search
None
See application file for complete search history.

(56) References Cited

U.S. PATENT DOCUMENTS

| | | | |
|---|---|---|---|
| 7,498,155 B2 | 3/2009 | Lovley et al. | |
| 8,232,584 B2 | 7/2012 | Lieber et al. | |
| 8,608,921 B2 | 12/2013 | Li et al. | |
| 8,729,233 B2 | 5/2014 | Reguera et al. | |
| 9,102,521 B2 | 8/2015 | Lieber et al. | |
| 9,234,508 B2 | 1/2016 | Sahin | |
| 9,697,460 B2 | 7/2017 | Collins et al. | |
| 9,784,249 B2 | 10/2017 | Li et al. | |
| 10,083,974 B1 | 9/2018 | Huang et al. | |
| 10,311,357 B2 | 6/2019 | Nugent et al. | |
| 10,388,370 B2 | 8/2019 | Schmidt et al. | |
| 10,684,244 B2 | 6/2020 | Chen | |
| 10,741,778 B2 | 8/2020 | Kirsch et al. | |
| 11,043,265 B2 | 6/2021 | Li et al. | |
| 11,063,227 B2 | 7/2021 | Kirsch et al. | |
| 11,066,449 B2 | 7/2021 | Lovley et al. | |
| 11,133,058 B1 | 9/2021 | Philip et al. | |
| 11,631,824 B2 | 4/2023 | Yao et al. | |
| 11,823,808 B2 | 11/2023 | Lovley et al. | |
| 11,982,637 B2 | 5/2024 | Yao et al. | |
| 2006/0113880 A1 | 6/2006 | Pei et al. | |
| 2007/0157967 A1 | 7/2007 | Mershin et al. | |
| 2008/0283799 A1 | 11/2008 | Alden et al. | |
| 2009/0188784 A1 | 7/2009 | Lee et al. | |
| 2010/0119879 A1 | 5/2010 | Girguis et al. | |
| 2012/0053319 A1 | 3/2012 | Reguera et al. | |
| 2014/0239237 A1 | 8/2014 | Reguera et al. | |
| 2014/0330337 A1 | 11/2014 | Linke et al. | |
| 2014/0336357 A1 | 11/2014 | Reguera et al. | |
| 2018/0007819 A1 | 1/2018 | Vajo et al. | |
| 2018/0195997 A1 | 7/2018 | Li et al. | |
| 2018/0202964 A1 | 7/2018 | Alam et al. | |
| 2018/0371029 A1 | 12/2018 | Lovley et al. | |
| 2019/0148085 A1 | 5/2019 | Kim et al. | |
| 2020/0090830 A1 | 3/2020 | Lovley et al. | |
| 2021/0002332 A1 | 1/2021 | Malvankar et al. | |
| 2021/0070811 A1 | 3/2021 | Reguera et al. | |
| 2021/0336169 A1 | 10/2021 | Yao et al. | |
| 2021/0341406 A1 | 11/2021 | Yao et al. | |
| 2021/0344286 A1 | 11/2021 | Yao et al. | |

(Continued)

FOREIGN PATENT DOCUMENTS

| | | |
|---|---|---|
| CN | 1527051 A | 9/2004 |
| CN | 108365776 A | 8/2018 |
| KR | 10-1203181 B1 | 11/2012 |

(Continued)

OTHER PUBLICATIONS

The Protein Man (https://info.gbiosciences.com/blog/bid/198500/8-protein-tags-explained; 2014).*

Malvankar et al., "Visualization of charge propagation along individual pili proteins using ambient electrostatic force microscopy" Nature Nanotechnology, vol. 9, Dec. 2014, pp. 1-10.

Marquez, A et al., "Nanoporous silk films with capillary action and size-exclusion capacity for sensitive glucose determination in whole blood," Lab Chip 21, 608-615 (2021).

Miaudet et al, "Thermo-electrical properties of PVA-nanotube composite fibers," ELSEVIER, ScienceDirect, Polymer 48 (2007) 4068-4074.

Milano, Gianluca, et al, "Self-limited single nanowire systems combining all-in—One memristive and neuromorphic functionalities", Dec. 2018, Nature Communications, Article No. 5151. pp. 1-10 (Year: 2018).

(Continued)

*Primary Examiner* — Brian Gangle
(74) *Attorney, Agent, or Firm* — Hamilton, Brook, Smith & Reynolds, P.C

(57) ABSTRACT

The present invention provides, in various embodiments, electrically conductive protein nanowires (e-PNs) having surface exposed peptides that confer additional sensing capabilities and/or enhance binding to other materials, as well as fusion proteins and methods for making such nanowires. The present invention also provides sensor devices comprising the nanowires.

20 Claims, 13 Drawing Sheets

Specification includes a Sequence Listing.

(56) References Cited

U.S. PATENT DOCUMENTS

| | | |
|---|---|---|
| 2023/0040959 A1 | 2/2023 | Lovley et al. |
| 2023/0344369 A1 | 10/2023 | Jun et al. |

FOREIGN PATENT DOCUMENTS

| | | | | |
|---|---|---|---|---|
| WO | WO-2013033456 A2 * | 3/2013 | ............... | B82Y 5/00 |
| WO | 2017/015306 A2 | 1/2017 | | |
| WO | 2019/144931 A1 | 8/2019 | | |
| WO | 2019/169331 A1 | 9/2019 | | |
| WO | 2020/069523 A1 | 4/2020 | | |
| WO | 2020/191281 A1 | 9/2020 | | |
| WO | 2021/102327 A1 | 5/2021 | | |

OTHER PUBLICATIONS

Nevin et al., "Anode Biofilm Transcriptomics Reveals Outer Surface Components Essential for High Density Current 14 Production in Geobacter sulfurreducens Fuel Cells", PLoS ONE, vol. 4, Issue 5, May 2009, pp. 1-11.

Nevin et al., "Power output and columbic efficiencies from biofilms of Geobacter sulfurreducens comparable to mixed 15 community microbial fuel cells", Environmental Microbiology, vol. 10, No. 10, 2008, pp. 2505-2514.

Ogura et al., "A Conductive and Humidity-Sensitive Composite Film Derived from Poly(o-phenylenediamine) and Polyvinyl Alcohol," J. Electrochem. Soc., vol. 142, No. 9, Sep. 1995.

Pang, et al, "The pressure exerted by a confined ideal gas," J. Phys. A: Math. Theor. 44, 365001 (2011).

Paradiso, et al., "Energy scavenging for mobile and wireless electronics," IEEE Pervasive Comp. 4, 18-27 (2005).

Qin, Y. et al., "Constant electricity generation in nanostructured silicon by evaporation-driven water flow," Angew. Chem. Int. Ed 59, 10619-10625 (2020).

Reardon, P.N. and Mueller, K.T., "Structure of the Type IVa Major Pilin from the Electrically Conductive Bacterial Nanowires of Geobacter sulfurreducens," The Journal of Biological Chemistry, vol. 288; No. 41; 29250-29256 (2013).

Reguera et al., "Extracellular electron transfer via microbial nanowires", Nature, vol. 435, Jun. 2005, pp. 1098-1101.

Ren, G. et al., "A facile and sustainable hygroelectric generator using whole-cell Geobacter sulfurreducens," Nano Energy 89, 106361 (2021).

Revil, et al., "Theory of ionic-surface electrical conduction in porous media," Phys. Rev. B 55, 1757-1773 (1997).

Rezende, et al., "Detection of charge distributions in insulator surfaces," J. Phys. Condens. Matter 21, 263002 (2009).

Richter 2011; Mutational Analysis of Geopilin Function in Geobacter sulfurreducens; Dissertation University of Massachusetts; Open Access Dissertations. 378. https://scholarworks.umass.edu/open_access_dissertations/378; (Year: 2011).

Rico, A.L. et al., "Functional reconstitution of the type IVa pilus assembly system from enterohaemorrhagic *Escherichic coli*," Mol. Microbiol., vol. 111; No. 3; 732-749 (2019).

Shen, et al., "Moisture-enabled electricity generation: from physics and materials to self-powered applications," Adv. Mater. 32, 2003722 (2020).

Shih et al., "Tryptophan-Accelerated Electron Flow Through Proteins", Science, vol. 320, Jun. 27, 2008, pp. 1760-1762.

Sisman, et al., "Quantum boundary layer: a non-uniform density distribution of an ideal gas in thermodynamic equilibrium," Phys. Lett. A 362, 16-20 (2007).

Sisman, et al., "The Casimir-like size effects in ideal gases," Phys. Lett. A 320, 360-366 (2004).

Stokes, et al., "A Standard solutions for humidity control at 25° C," Ind. Eng. Chem. 41, 2013 (1949).

Sun et al, "Flexible polydimethylsiloxane/multi-walled carbon nanotubes membranous metacomposites with negative permittivity," Elsevier, Polymer 125 (2017) 50-57.

Sun, Z. et al., "Emerging design principles, materials, and applications for moisture-enabled electric generation," eScience (2022) https://doi.org/10.1016/j.esci.2021.12.009.

Tan et al., "Synthetic Biological Protein Nanowires with High Conductivity," small 2016, 12, No. 33, 4481-4485.

Tan et al., "Expressing the Geobacter metallireducens PilA in Geobacter sulfurreducens Yields Pili with Exceptional Conductivity," American Society for Microbiology, Jan./Feb. 2017, vol. 8, Issue 1 e02203-16.

Tang et al, "Effect of pH on Protein Distribution in Electrospun PVA/BSA Composite Nanofibers," 2012 American Chemical Society, 1269-1278.

Tang, et al., "Compilation and evaluation of gas phase diffusion coefficients of reactive trace gases in the atmosphere: vol. 2. Diffusivities of organic compounds, pressure-normalized mean free paths, and average Knudsen numbers for gas uptake calculations," Atoms. Chem. Phys. 15, 5585-5598 (2015).

Tseng et al., "Digital memory device based on tobacco mosaic virus conjugated with nanoparticles," nature hanotechnology, vol. 1., Oct. 2006, pp. 72-77.

Ueki T., et al., "An *Escherichia coli* Chassis for Production of Electrically Conductive Protein Nanowires," 9(3):647-654 ACS Synth Biol. (2020).

Ueki T., et al., "Decorating the Outer Surface of Microbially Produced Protein Nanowires with Peptides," ACS Synth Biol. X;8{8}:1809-1817 (2019).

Ueki, Toshiyuki, et al. "Decorating microbially produced protein nanowires with peptide ligands." bioRxiv (2019): 590224.

Vargas et al., "Aromatic Amino Acids Required for Pili Conductivity and Long-Range Extracellular Electron Transport in Geobacter sulfurreducens", mBio, vol. 4, Issue 2, Mar./Apr. 2013, pp. 1-6.

Walker et al., "Electrically conductive pili from pilin genes of phylogenetically diverse microorganisms," The ISME Journal (2018) 12, 48-58.

Wu, S., et al, "Regulation of expression of pilA gene in Myxococcus xanthus," Journal of Bacteriology, 179 (24):7748-7758 (1997).

Yang, Yen-Chun, et al, "PilR enhances the sensitivity of Xanthomonas axonopodis pv. citri to the infection of filamentous bacteriophage Cf," Current Microbiology, 48(4):251-261 (2004).

Yi Cui et al, "Nanowire Nanosensors for Highly Sensitive and Selective Detection of Biological and Chemical Species", Aug. 2021, Science Magazine, vol. 293, pp. 1289-1292. (Year: 2021).

Yin, B., et al., "Bioinspired and bristled microparticles for ultrasensitive pressure and strain sensors," Nat. Commun. 9, 5161 (2018).

Zezelj et al., Publisher's Note: From percolating to dense random stick networks: Conductivity model nvestigation [Phys. Rev_ B 86, 134202 (2012)]. Physical Review B 86, 139904(E) (2012).

Zhang et al., "Composite films of nanostructured polyaniline with poly(vinyl alcohol)," Elsevier, Synthetic Metals 12E (2002) 83-89.

Zhang et al., "Electrical and dielectric behaviors and their origins in the three-dimensional polyvinyl alcohol/MWCN-Composites with low percolation threshold," Elsevier, Carbon 47 (2009) 1311-1320.

Zhang, et al., "Digestion of ambient humidity for energy generation," Joule 4, 2532-2536 (2020).

Zhang, et al., "Emerging hydrovoltaic technology," Nat. Nanotechnol. 13, 1109-1119 (2018).

Zhang, et al., "Sub-10 nm wide cellulose nanofibers for ultrathin nanoporous membranes with high organic permeation," Adv. Funct. Mater. 26, 792-800 (2016).

Zhao, F. et al., "Direct power generation from a graphene oxide film under moisture," Adv. Mater. 27, 4351-4357 (2015).

Zhou, et al., "Origin of the chemical and kinetic stability of graphene oxide," Sci. Rep. 3, 2484 (2013).

Zhou, Jiangfeng, et al, "Development of nanowire-modified electrodes applied in the locally enhanced electric field treatment (LEE FT) for water disinfection", 2020, Journals of Materials Chemistry. Article, 12262-12277 (Year: 2020).

Adhikari et al., "Conductivity of individual Geobacter pili," RSC Advances., 2016, 6, 8354-8357.

Al-abadleh, et al., "FT-IT study of water adsorption on aluminum oxide surfaces," Langmuir 19, 341-347 (2003).

Amrin et al., "Electrical properties and conduction mechanism in carboxylfunclionalized multiwalled carbon hanolubes/poly(vinyl alcohol) composites," J Maler Sci (2016) 51:2453-2464.

(56) References Cited

OTHER PUBLICATIONS

Bai, J. et al., "Sunlight-coordinated high-performance moisture power in natural condition," Adv. Mater. (2022) https://doi.org/10.1002/adma.202103897.
Balberg et al., "Excluded volume and its relation to the onset of percolation," Physical Review B, vol. 30, No. 7, Oct. 1, 1984.
Bauhofer et al, "A review and analysis of electrical percolation in carbon nanolube polymer composites," Elsevier, Composites Science and Technology 69 (2009) 1486-1498.
Byrne et al., "Recent Advances in Research on Carbon Nanolube-Polymer Composites," Advanced Materials, 2010,22, 1672-1688.
Celzard et al,"Critical concentration in percolating systems containing a high-aspect-ratio filler," Physical Review 8, vol. 53, No. 10, Mar. 1, 1996.
Chandrakishore et al, "Facile synthesis of carbon nanolubes and their use in the fabrication of resistive switching memory devices," RSC Advances, 2014, 4, 9905-9911.
Chen et al., "Electrical Conductivity of Polymer Blends of Poly(3,4-ethylenedioxythiophene) : Poly (styrenesulfonate) :N-Methyl-2-pyrrolidinone and Polyvinyl Alcohol," Journal of Applied Polymer Science, vol. 125, 3134-3141 (2012).
Cheng, H. et al., "Spontaneous power source in ambient air of a well-directionally reduced graphene oxide bulk," Energy Environ. Sci. 11, 2839 (2018).
Childers et al., "Geobacter metallireducens accesses insoluble Fe(III) oxide by chemotaxis" Nature, vol. 416, Apr. 18, 2002, pp. 767-769.
Cho et al., "Synthesis and electrical properties of polymer composites with polyaniline nanoparticles," Elsevier, Materials Science and Engineering C 24 (2004) 15-18.
Coppi et al., "Development of a Genetic System for Geobacter sulfurreducens", Applied and Environmental Microbiology, vol. 67, No. 7, Jul. 2001, pp. 3180-3187.
Cui, Yi, et al, "Nanowire Nanosensors for Highly Sensitive and Selective Detection of Biological and Chemical Species", Aug. 2021, Science Magazine, vol. 293, pp. 1289-1292. (Year: 2021).
Fu, T. et al., "Self-sustained green neuromorphic interfaces," Nat. Commun. 12, 3351 (2021).
Fu, Tianda, et al, "Bioinspired bio-voltage memristors", Nature Communications, 2020, Article pp. 1-10 (Year: 2020).
Gangopadhyay et al., "Polyaniline-poly(vinyl alcohol) conducting composite: material with easy processability 2nd novel application potential," Elsevier, Synthetic Metals 123 (2001) 21-31.
Gerald F. Audette et al, "Protein Nanotubes: From Bio-nanotech towards Medical Applications", Jun. 2019, Biomedicines Journal, vol. 7/46. (Year: 2019).
Gielen, et al., "The role of renewable energy in the global energy transformation," Energy Strategy Rev. 24, 38-50 (2019).
Green et al, "Conductive Hydrogels: Mechanically Robust Hybrids for Use as Biomalerials," Macromolecular Bioscience, 2012, 12, 494-501.
Guo et al, "Flexible transparent conductors based on metal nanowire networks," Elsevier, Materials Today, vol. 18, No. 3, Apr. 2015.
Guterman, et al., "Toward Peptide-Based Bioelectronics: Reductionist Design of Conductive Pili Mimetics," Bioelectron Med (Lond.) May 2018: 1(2): 131-137.
Han, et al., "Facile synthesis of poly(3,4-ethylenedioxythiophene) nanofibers from an aqueous surfactant solution," Small 2, 1164-1169 (2006).
Ho, et al., "Gas Transport in Porous Media," (Springer, 2006).
International Search Report and Written Opinion received for PCT Patent Application No. PCT/US2020/023824, mailed on Jul. 24, 2020, 9 pages.
Jerry A. Fereira et al, "Tunneling explains efficient electron transport via protein junctions", Weizmann Institute of SCience Reports, Nov. 2017, vol. 114, No. 20 (Year: 2017).

Kaunda, et al., "Hydropower in the context of sustainable energy supply: a review of technologies and challenges," ISRN Renewable Energy 2012, 730631 (2012).
Kumar, Anish, et al, "Protein Biosensors Based on Polymer Nanowires, Carbon Nanotubes and Zinc Oxide Nanorods", Sensors Journal, May 2011, 5087-5111 {Year: 2011).
Langmuir, "Vapor pressures, evaporation, condensation and adsorption," J. Am. Chem. Soc. 54, 2798-2832 (1932).
Li et al, "Ordered multiphase polymer nanocomposites for high-performance solid-slate supercapacitors," Elsevier, Composites: Part B 71 (2015), 40-44.
Liu et al, "Flexible supercapacitor sheets based on hybrid nanocomposite materials," Elsevier, Nano Energy (2013) 133-137.
Liu et al., "A Geobacter sulfurreducens Strain Expressing Pseudomonas aeruginosa Type IV Pili Localizes OmcS on Pili but Is Deficient in Fe(III) Oxide Reduction and Current Production", Applied and Environmental Microbiology, vol. 80, No. 3, Feb. 2014, pp. 1219-1224 (cited in specification on p. 14).
Liu X., et al., "Power Generation from Ambient Humidity Using Protein Nanowires," Nature; 578: 550-554 (2020).
Liu, et al., "Biological Synthesis of High-Conductive Pili in Aerobic Bacterium Pseudomonas Aeruginosa," Applied Microbiology and Biotechnology (2019) 103:1535-1544.
Liu, et al., "Induced potential in porous carbon films through water vapor absorption," Angew. Chem. Int. Ed. 55, 8003-8007 (2016).
Liu, T. et al., "Regulating the interlayer spacing of graphene oxide membranes and enhancing their stability by use of PACl," Environ. Sci. Technol. 53, 11949-11959 (2019).
Liu, X. et al., "Multifunctional protein nanowire humidity sensors for green wearable electronics," Adv. Electron. Mater. 6, 2000721 (2020).
Lovely,D., et al., "Geobacter Protein Nanowires", Front. Microbial. 10, 2078 (2019).
Lovley et al., "Seeing is believing: novel imaging techniques help clarify microbial nanowire structure and function", Environmental microbiology, vol. 17, Issue 7, 2015, pp. 2209-2215.
Lovley, "e-Biologics: Fabrication of Sustainable Electronics with 'Green' Biological Materials," American Society for Microbiology, May/Jun. 2017, vol. 8, Issue 3 e00695-17.
Lovley, "Electrically conductive pili: Biological function and potential applications in electronics," Science Direct, Current Opinion in Electrochemistry 2017, 4: 190-198.
Lovley, et al., "Intrinsically conductive microbial nanowires for 'green' electronics with novel functions," Trends Biotechnol. 39, 940-952 (2021).
Makhlouki et al., "Transport Properties in Polypyrrole-PVA Composites: Evidence for Hopping Conduction," Journal of Applied Polymer Science, vol. 44, 443-446 (1992).
Malhofer et al., "Direct visualization of percolation paths in carbon nanolube/polymer composites," Elsevier, Organic Electronics 45 (2017) 151-158.
Malvankar et al., "Lack of cytochrome involvement in long-range electron transport through conductive biofilms and nanowires of Geobacter sulfurreducens", Energy & Environmental Science, vol. 5, 2012, pp. 8651-8686.
Malvankar et al., "Structural Basis for Metallic-Like Conductivity in Microbial Nanowires", mBio, vol. 4, Issue 2, Mar./Apr. 2015, pages. mBio 6:e00084-00015.
Malvankar et al., "Tunable metallic-like conductivity in microbial nanowires", Nature Nanotechnology, vol. 6, Sep. 2011, pp. 573-579.
Malvankar et al., "Microbial nanowires for bioenergy applications", Current Opinion in Biotechnology, vol. 27, 2017, pp. 88-95.
Malvankar et al., "Microbial Nanowires: A New Paradigm for Biological Electron Transfer and Bioelectronics", ChemSusChem Concepts, vol. 5, 2012, pp. 1039-1046.

* cited by examiner

Wild-type pilA (SEQ ID NO: 1)
ATGCTTCAGAAACTCAGAAACAGGAAAAGGTTTCACCCTTATCGAGCTGCTGATCGTCGTT
GCGATCATCGGTATTCTCGCTGCAATTGCGATTCCGCAGTTCTCGGCGTATCGTGTCAAG
GCGTACAACAGCGCGGCGTCAAGCGACTTGAGAAACCTGAGAAACCTGAAGACTGCTCTTGAGTCCGCA
TTTGCTGATGATCAAACCTATCCGCCCGAAAGTTAA pilA-6His (SEQ ID NO: 12)
ATGCTTCAGAAACTCAGAAACAGGAAAAGGTTTCACCCTTATCGAGCTGCTGATCGTCGTT
GCGATCATCGGTATTCTCGCTGCAATTGCGATTCCGCAGTTCTCGGCGTATCGTGTCAAG
GCGTACAACAGCGCGGCGTCAAGCGACTTGAGAAACCTGAAGACTGCTCTTGAGTCCGCA
TTTGCTGATGATCAAACCTATCCGCCCGAAAGTCACCACCACCACCACCACTAA pilA-HA (SEQ ID NO: 14)
ATGCTTCAGAAACTCAGAAACAGGAAAAGGTTTCACCCTTATCGAGCTGCTGATCGTCGTT
GCGATCATCGGTATTCTCGCTGCAATTGCGATTCCGCAGTTCTCGGCGTATCGTGTCAAG
GCGTACAACAGCGCGGCGTCAAGCGACTTGAGAAACCTGAAGACTGCTCTTGAGTCCGCA
TTTGCTGATGATCAAACCTATCCGCCCGAAAGTTACCCGTACGACGTCCCGGACTACGCGTAA

FIG. 1

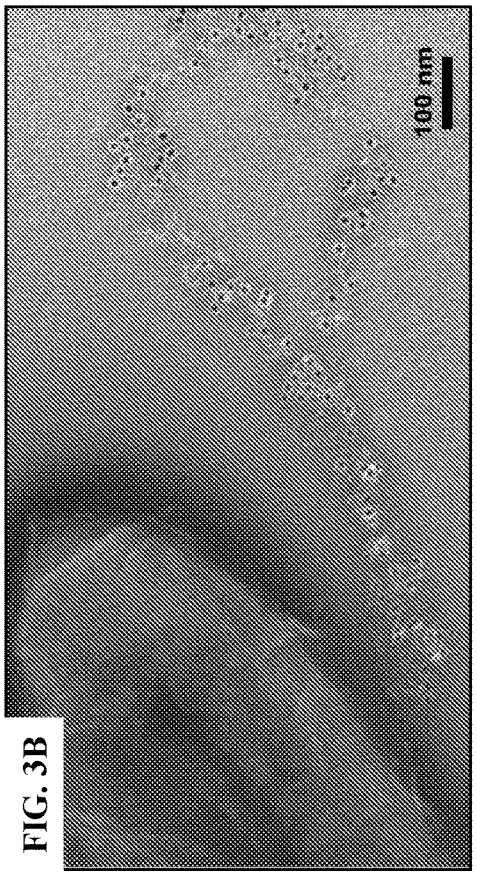
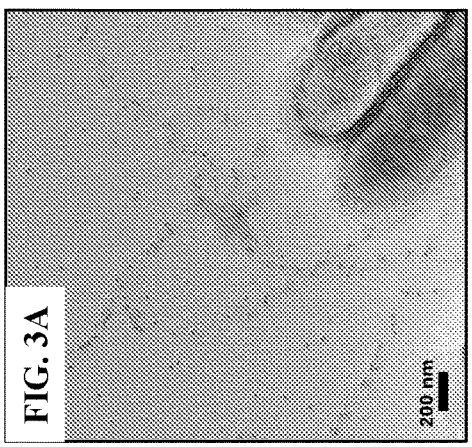
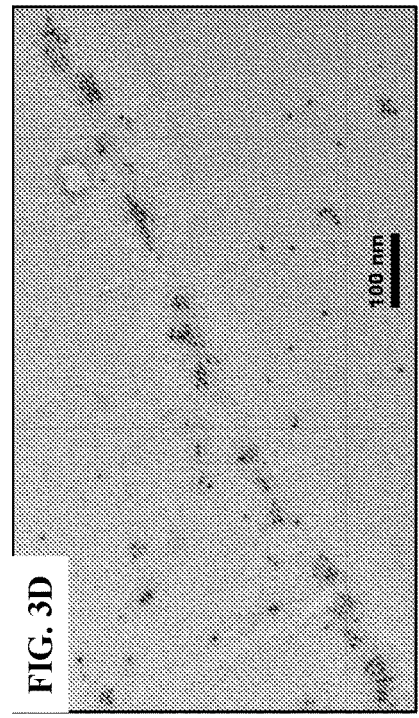
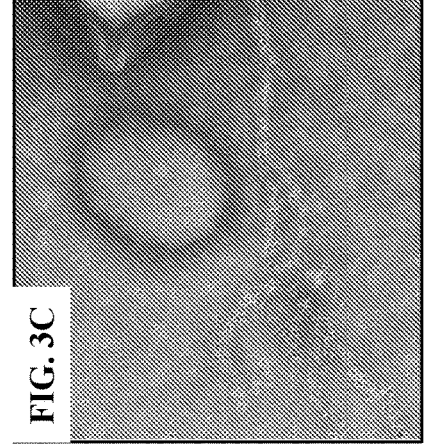
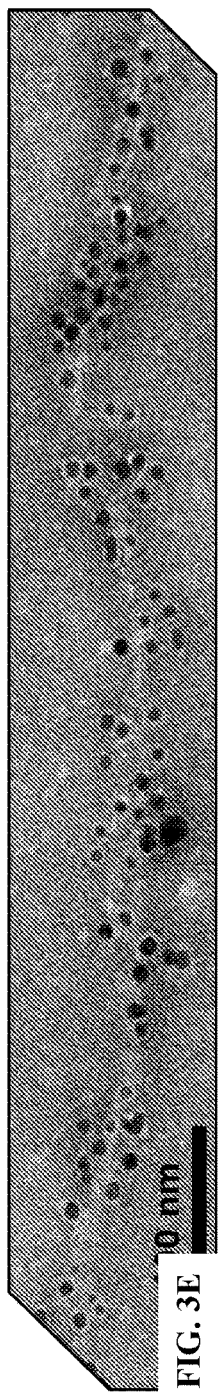

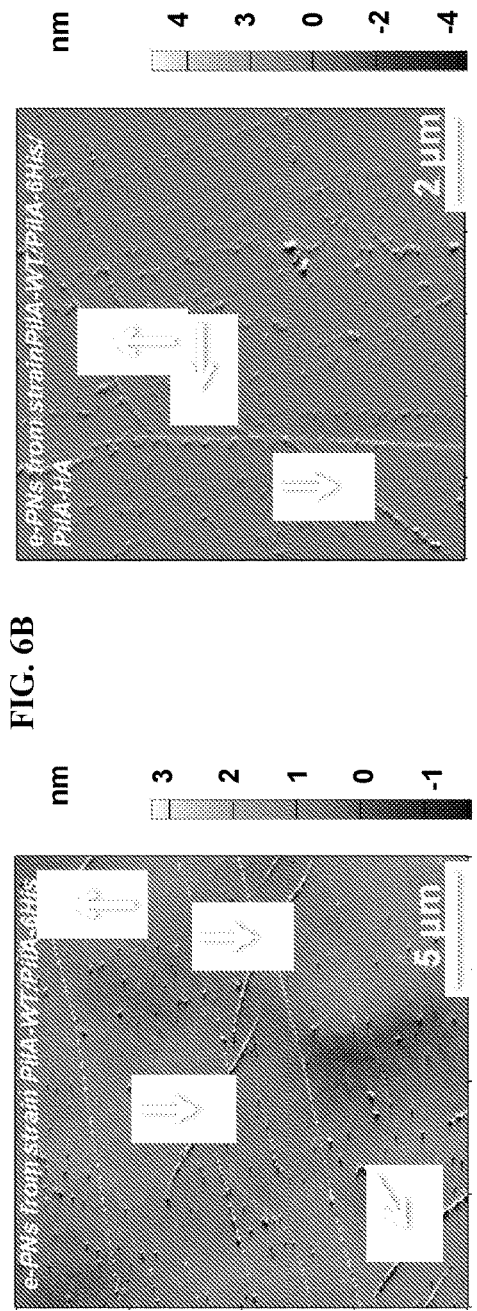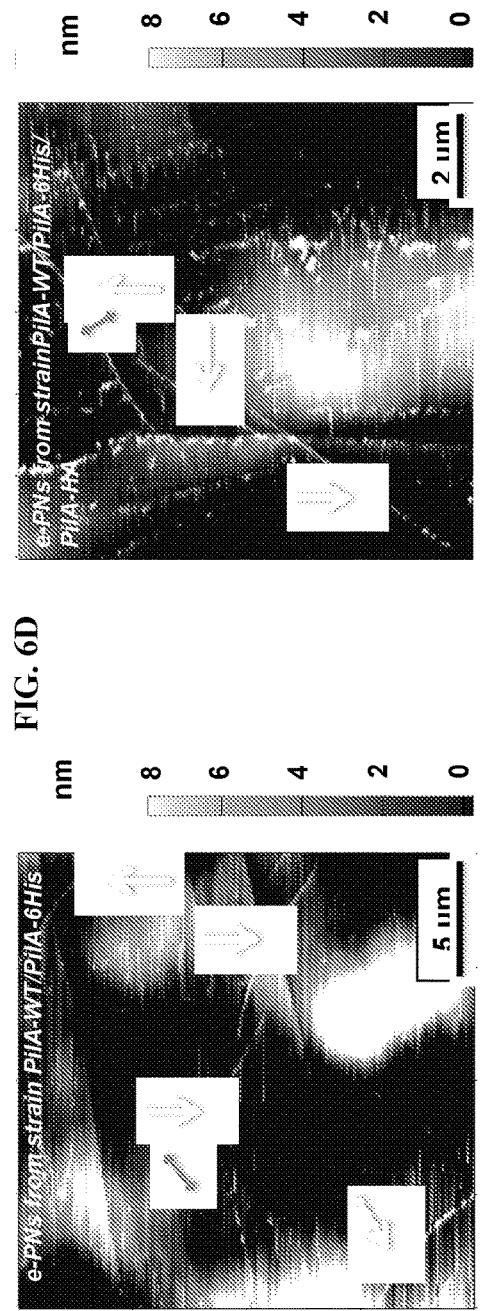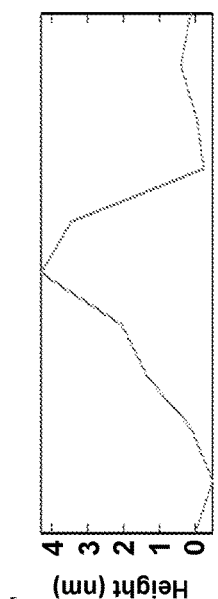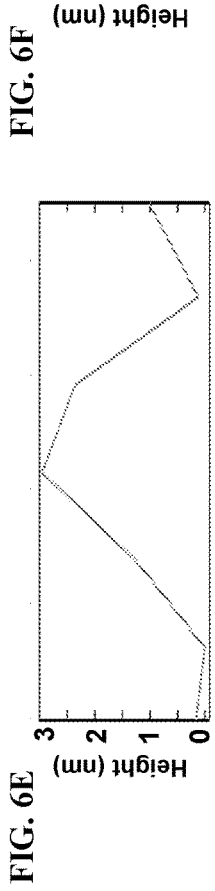
FIG. 6A  FIG. 6B  FIG. 6C  FIG. 6D  FIG. 6E  FIG. 6F

PilA-HA
```
 1          11         21         31         41         51         61
FTLIELLIVVAIIGILAAIAIPQFSAYRVKAYNSAASSDLRNLKTALESAFADDQTYPPES YPYDVPDYA
                                                     (SEQ ID NO: 15)
```
FIG. 8A
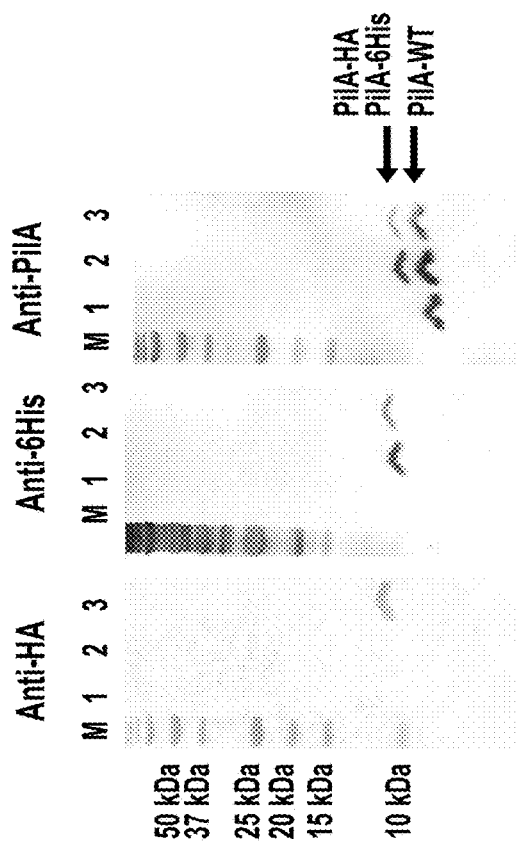
FIG. 8B
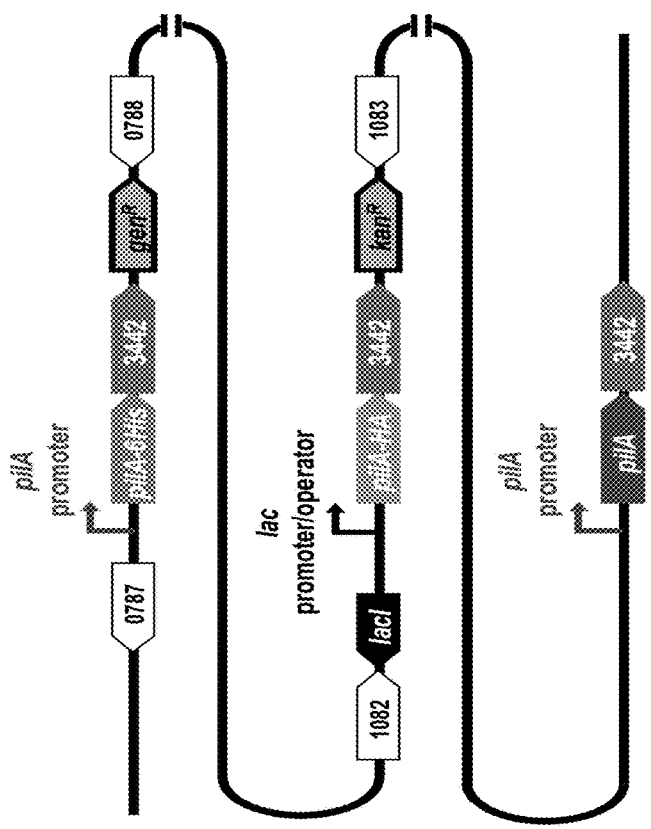
FIG. 8C

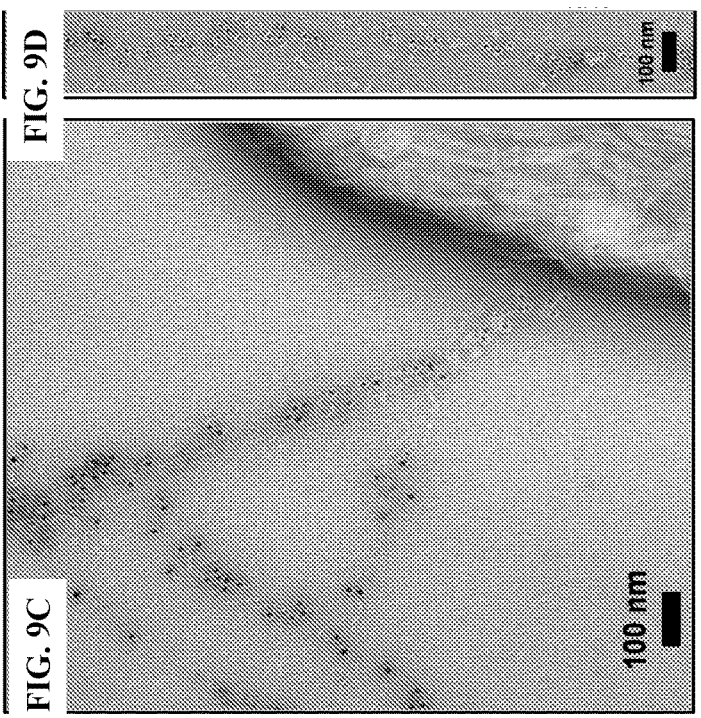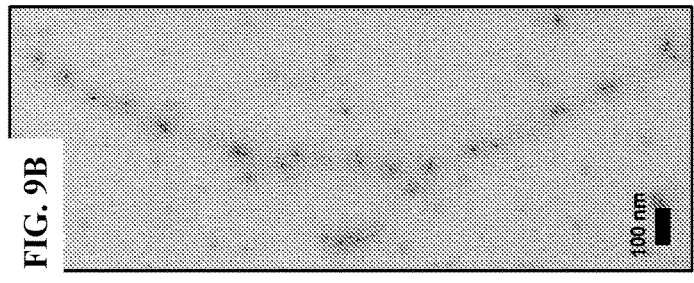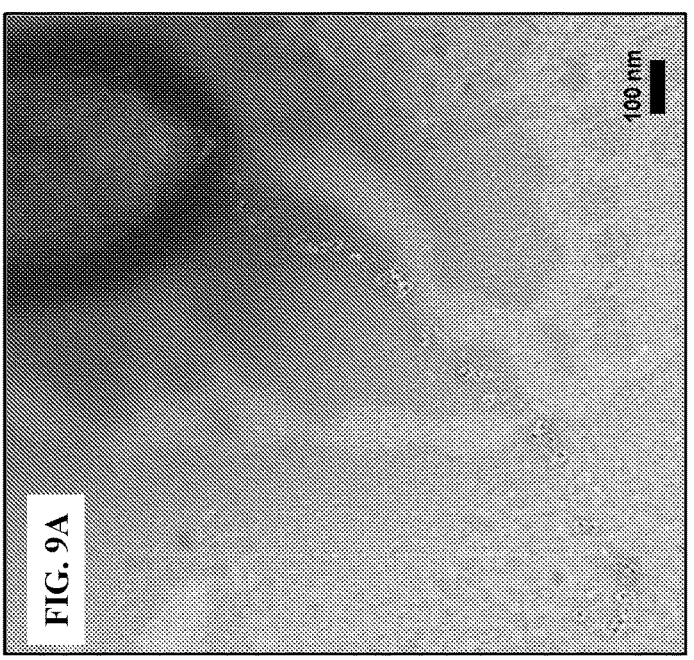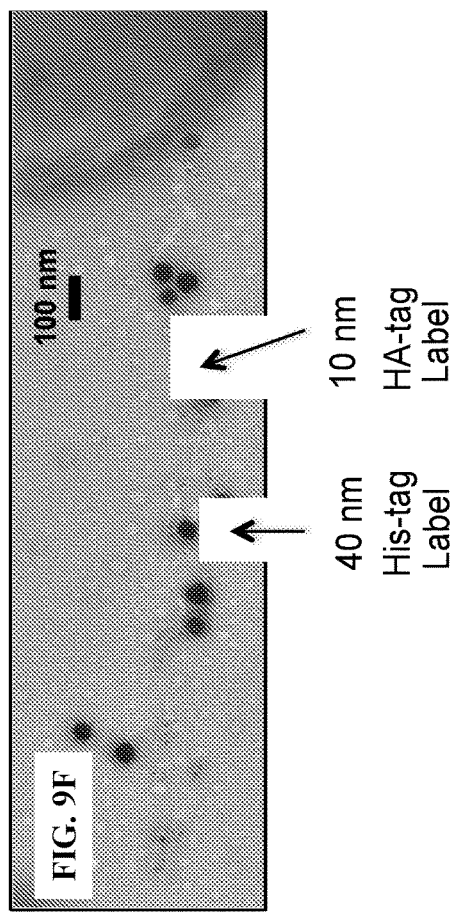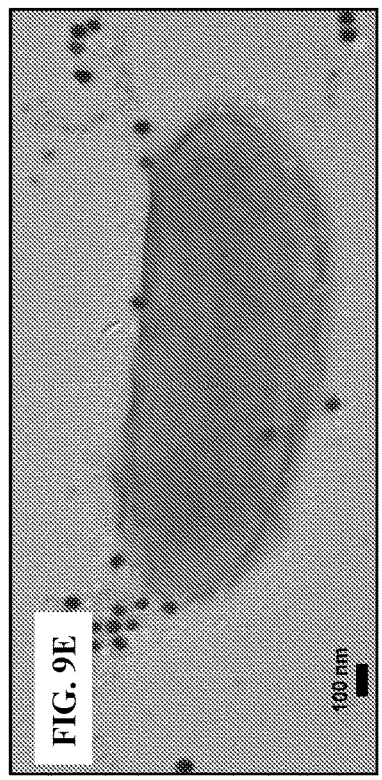

MICROBIAL NANOWIRES MODIFIED TO CONTAIN PEPTIDES AND METHODS OF MAKING

RELATED APPLICATION(S)

This application is the U.S. National Stage of International Application No. PCT/US2020/023824, filed Mar. 20, 2020, published in English, which claims the benefit of U.S. Provisional Application No. 62/821,208, filed on Mar. 20, 2019. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
  a) File name: 46821013002_Sequence_Listing_revised.txt; created Apr. 15, 2022, 51,005 Bytes in size.

BACKGROUND

Microbially produced, electrically conductive protein nanowires (e-PNs) possess properties and possibilities for functionalization not found in other electronic nanowire materials. Diverse microorganisms in both the Bacteria and Archaea produce e-PNs. Functional analysis of Geobacter e-PNs have demonstrated that, when attached to cells, they serve as conduits for long-range electron exchange with other cells or minerals.

The most intensively studied e-PNs are the electrically conductive pili of the microorganism *Geobacter sulfurreducens*. *G. sulfurreducens* assembles the thin (3 nm), long (10-30 μm) e-PNs from multiple copies of just one short (61 amino acids) monomer peptide. Even though they are comprised of protein, the e-PNs produced with *G. sulfurreducens* are remarkably robust. They retain function under conditions required for the fabrication of electronic materials, including stability in a range of organic solvents and temperatures greater than 100° C. The *G. sulfurreducens* e-PNs are produced from renewable feedstocks. No harsh chemicals are required for e-PN production and there are no toxic components in the final product. Unlike silicon nanowires, e-PNs do not dissolve in water or bodily fluids, a distinct advantage for wearable and environmental electronic sensor applications, as well as implantable electronics. e-PNs have evolved for making cell-to-cell electrical connections, suggesting they may be more biocompatible than other nanowire materials. The dramatic change in e-PN conductivity in response to pH suggests that they may be readily adapted for diverse sensor functions.

SUMMARY

The potential applications of e-PNs may be expanded if their outer surface is modified to confer additional sensing capabilities, enhance binding to other materials, and/or confer other functions. Accordingly, there is a need for modifying naturally occurring e-PNs to confer additional functionalities.

The invention described herein generally relates to electrically conductive protein nanowires having peptide ligands (e.g., surface-exposed peptides) that confer additional functionalities (e.g., a sensing functionality, a binding functionality) to the nanowires.

One aspect of the invention relates to a fusion protein, wherein the fusion protein comprises a type IV pilin monomer and a tag at the C-terminus of the type IV pilin monomer. In some embodiments, the tag is a peptide. In other embodiments, the tag is a single amino acid.

Another aspect of the invention relates to an electrically conductive nanowire, wherein the electrically conductive nanowire comprises a fusion protein comprising a type IV pilin monomer and a tag at the C-terminus of the type IV pilin monomer.

Another aspect of the invention relates to a nanowire sensor device comprising: an electrically conductive nanowire that comprises a fusion protein comprising a type IV pilin monomer and a tag at the C-terminus of the type IV pilin monomer; a first electrode having a first electrode terminal, wherein the first electrode is configured to support and is in physical contact with the electrically conductive nanowire; a second electrode having a second electrode terminal, wherein the second electrode is configured to support and is in physical contact with the electrically conductive nanowire; an electrical resistance connected between the first and the second electrode terminals; and an electrical current monitor in electrical communication with the electrical resistance. The electrical current monitor is configured to measure an electrical current passing through the electrical resistance in the device.

Another aspect of the invention relates to a polynucleotide that encodes a fusion protein comprising a type IV pilin monomer and a tag at the C-terminus of the type IV pilin monomer.

Another aspect of the invention relates to an expression vector comprising a polynucleotide that encodes a fusion protein comprising a type IV pilin monomer and a tag at the C-terminus of the type IV pilin monomer.

Another aspect of the invention relates to a host cell comprising a polynucleotide or an expression vector comprising a polynucleotide, wherein the polynucleotide encodes a fusion protein comprising a type IV pilin monomer and a tag at the C-terminus of the type IV pilin monomer.

Another aspect of the invention relates to a method of producing electrically conductive protein nanowires, comprising the steps of:
  a) introducing a polynucleotide or an expression vector comprising the polynucleotide into a host cell, wherein the polynucleotide encodes a fusion protein comprising a type IV pilin monomer and a tag at the C-terminus of the type IV pilin monomer;
  b) placing the host cell in a culture medium conditioned for producing type IV pili;
  c) culturing the host cell for a time sufficient to produce a desired quantity of the type IV pili; and
  d) isolating the type IV pili from the culture medium.

BRIEF DESCRIPTION OF THE DRAWINGS

FIG. 1 depicts the DNA sequence of the pilA, pilA-6His and pilA HA coding sequences. The coding sequence for the tag is underlined in pilA-6His and pilA-HA sequences.

FIG. 2A depicts amino acid sequences of wild-type PilA and PilA-6His. FIG. 2B shows the location of wild-type pilA and pilA-6His genes on the chromosome. Numbers are gene numbers from the genome sequence (NCBI, NC_017454.1). gen$^R$ is the gentamicin resistance gene. FIG. 2C is a Western blot of wild-type (lane 1) and PilA-WT/

PilA-6His (lane 2) strains. Lane M is the molecular weight standard markers. The headings designate the antibodies employed.

FIGS. 3A-3E are transmission electron micrographs showing that 6His-tag is incorporated into the e-PNs of *G. sulfurreducens* strain PilA-WT/PilA-6His. FIGS. 3A-3B and 3C-3E are immunogold labeling and $Ni^{2+}$-NTA-gold labeling of 6His-tag, respectively.

FIGS. 4A-4D are transmission electron micrographs showing a lack of filaments labeling of 6His-tag in the wild-type strain. FIGS. 4A-4B and 4C-4D are immunogold labeling and $Ni^{2+}$-NTA-gold labeling of 6His-tag, respectively.

Figure 5:
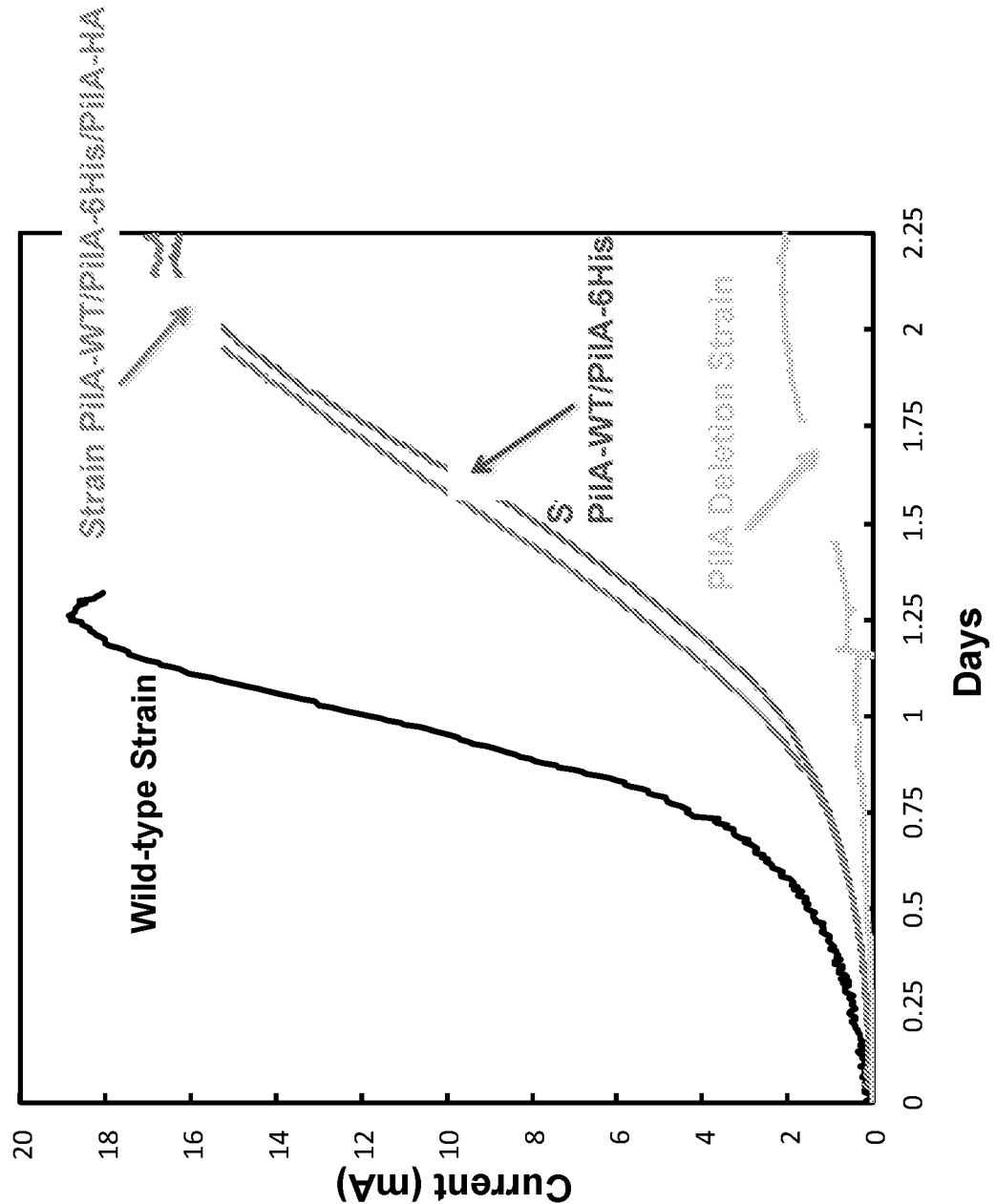

FIG. 5 depicts current production of wild-type *G. sulfurreducens* and *G. sulfurreducens* strains PilA-WT/PilA-6His and PilA-WT/PilA-6His/PilA-HA.

Figure 6G:
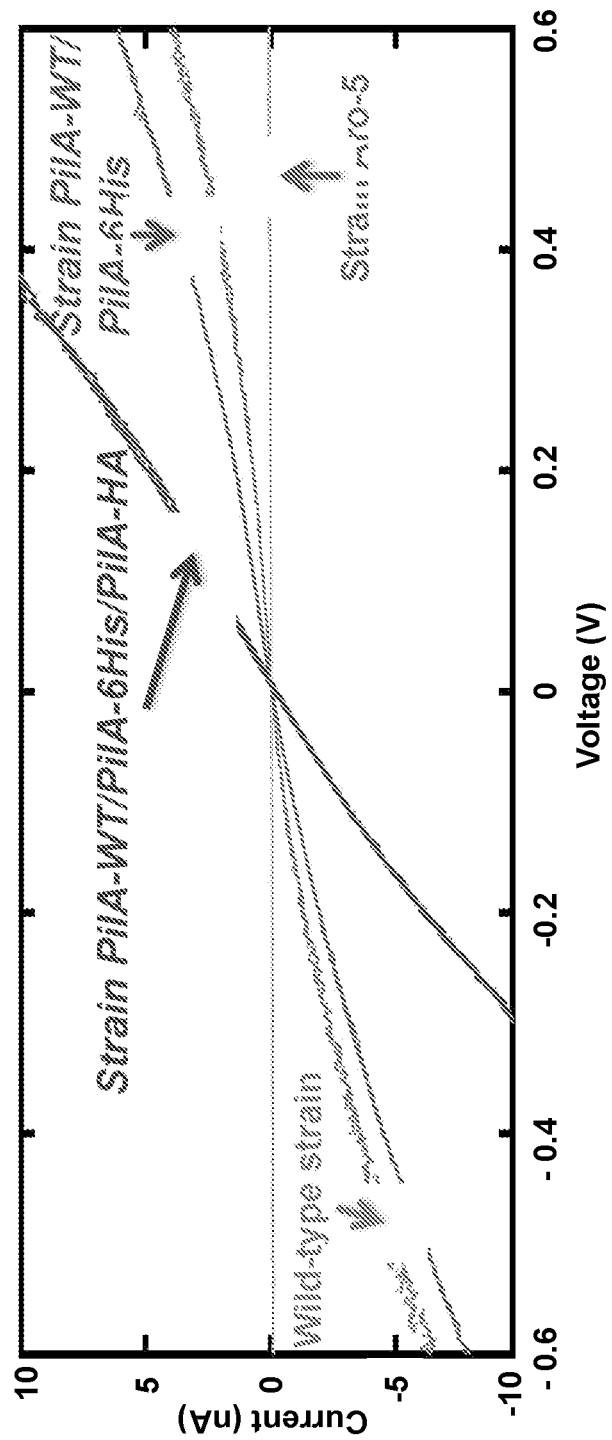

FIGS. 6A-6G show conductance of synthetic e-PNs decorated with peptide tags. FIGS. 6A-6F are representative contact topological imaging of e-PNs from *G. sulfurreducens* strains PilA-WT/PilA-6His and PilA-WT/PilA-6His/PilA-HA. FIG. 6G Point-mode current response (I-V) spectroscopy of e-PNs from PilA-WT/PilA-6His and PilA-WT/PilA-6His/PilA-HA, compared to previously published data on e-PNs from the wild-type strain of *G. sulfurreducens* and strain Aro-5, which expresses poorly conductive pili.

Figures 7A, 7B, 7C:
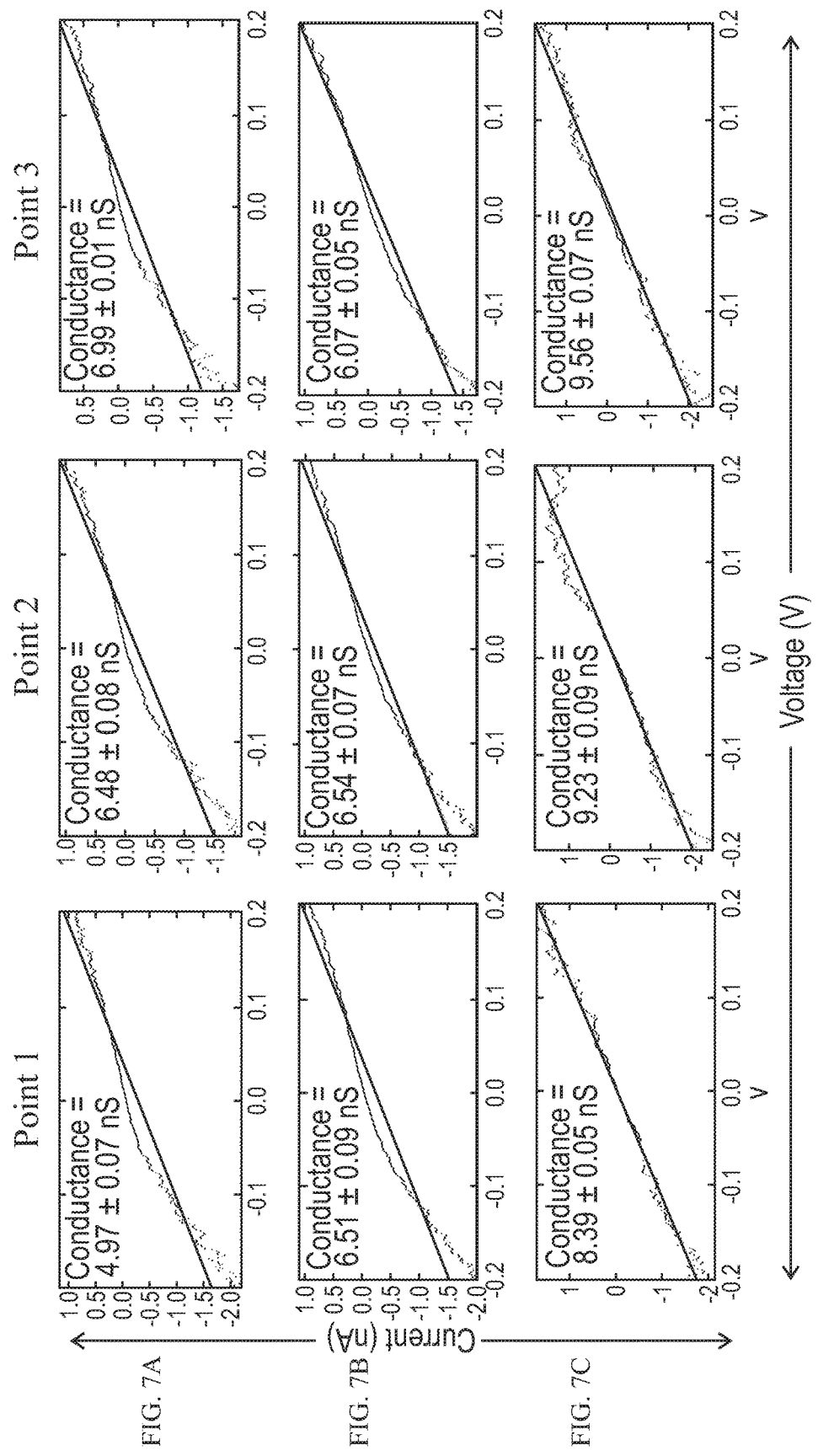

FIGS. 7A-7C show conductance for *G. sulfurreducens* strain PilA-WT/PilA-6His using point-mode current response (I-V) spectroscopy. Three individual wires (FIGS. 7A, 7B and 7C) were measured at three independent points (1-3). Calculations were made using a linear fit model between −0.2 V and 0.2 V. S: Siemen.

FIGS. 8A-8C depict the construction of *G. sulfurreducens* strain PilA-WT/PilA-6His/PilA-HA and expression of pilin monomers. FIG. 8A depicts the amino acid sequence of the PHA-HA. FIG. 8B depicts the location of wild-type pilA, pilA-6His, and pilA-HA genes on the chromosome. lad is the Lac repressor gene. $kan^R$ is the kanamycin resistance gene. FIG. 8C Western blot analysis of cell lysates of wild-type (lane 1), PilA-WT/PilA-6His (lane 2), and PilA-WT/PilA-6His/PilA-HA (lane 3) strains. Lane M is the molecular weight standard markers. Headings designate the antibodies employed.

FIGS. 9A-9F are transmission electron microscopy images of immunogold labeling of *G. sulfurreducens* strain PilA-WT/PilA-6His/PilA-HA for 6His-tag (FIGS. 9A-9B), HA-tag (FIGS. 9C-9D), and both tags (FIGS. 9E-9F). The diameters of the gold nanoparticles were 10 nm in FIGS. 9A-9D and 40 nm in FIGS. 9E-9F.

Figure 10A:
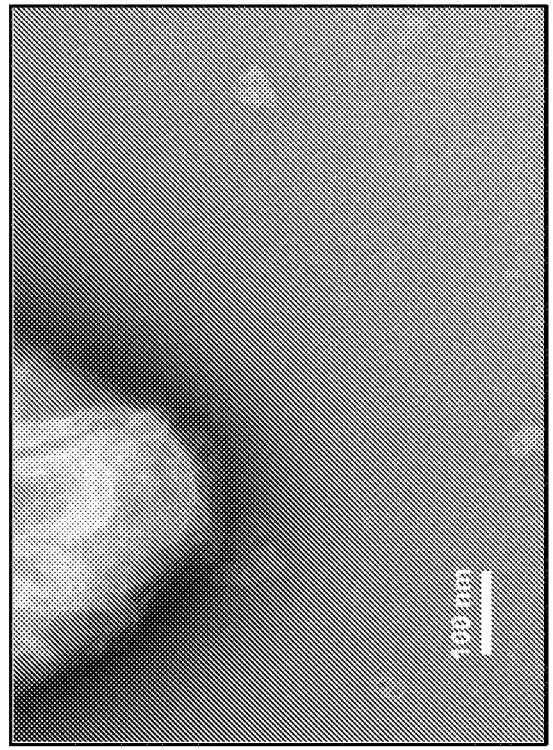
Figure 10B:
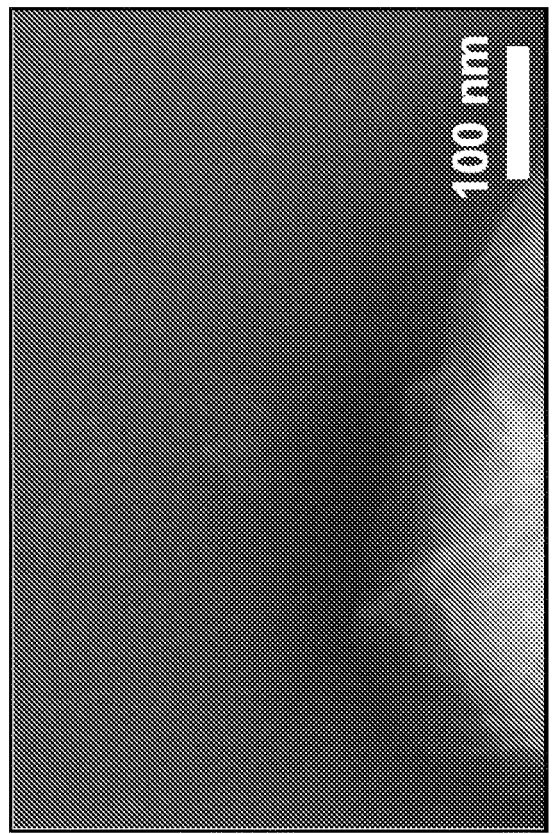

FIGS. 10A and 10B are transmission electron microscopy images demonstrating a lack of immunogold labeling of the HA-tag in the PilA-WT (FIG. 10A) and PilA-6His (FIG. 10B) strains.

Figures 11A, 11B, 11C:
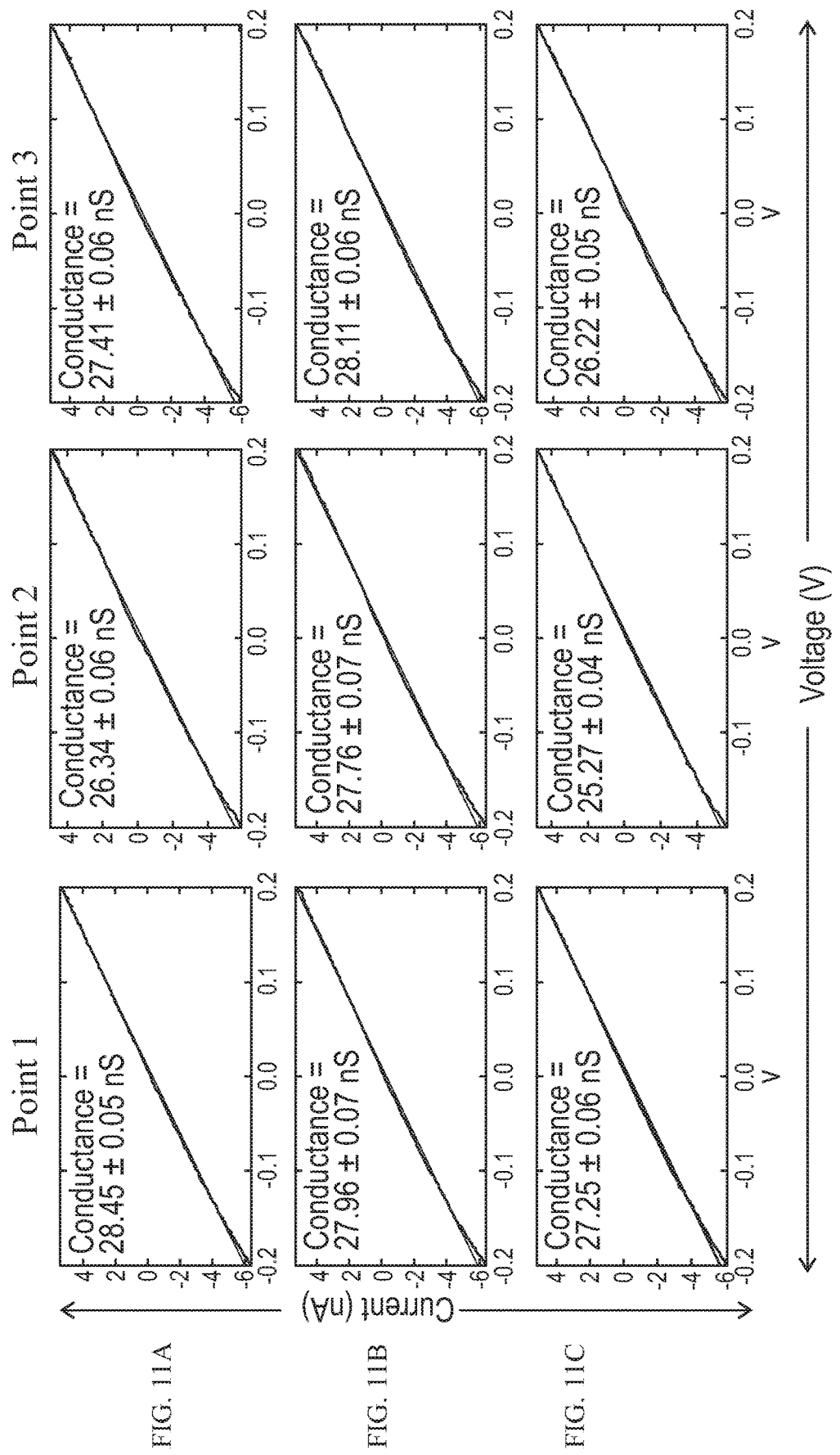

FIGS. 11A-11C show conductance for *G. sulfurreducens* strain PilA-WT/PilA-6His/PilA-HA filaments using point-mode current response (I-V) spectroscopy. Three individual wires (FIGS. 11A, 11B and 11C) were measured at three independent points (1-3). Calculations were made using a linear fit model between −0.2 V and 0.2 V. S: Siemen.

Figure 12A:
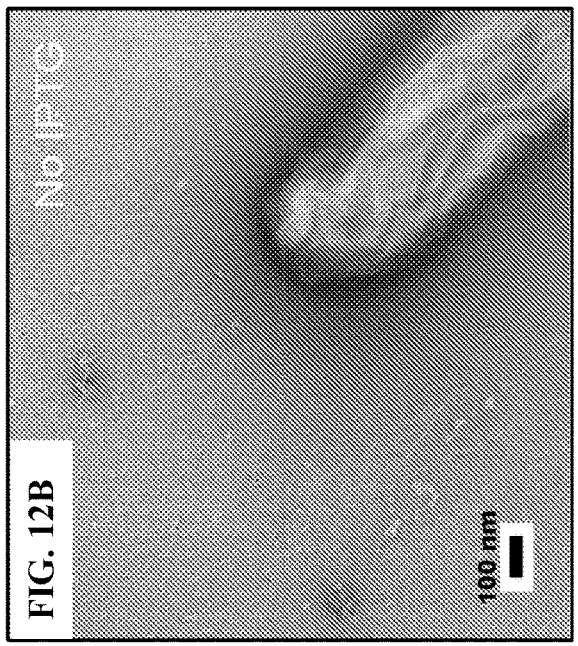
Figure 12B:
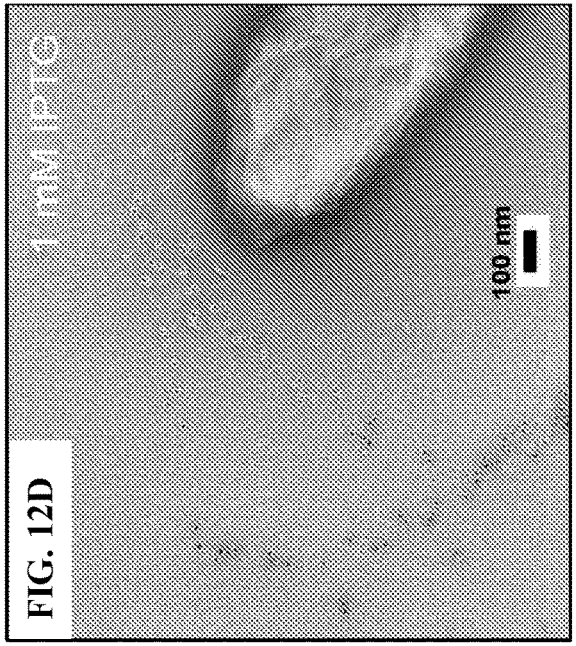
Figure 12C:
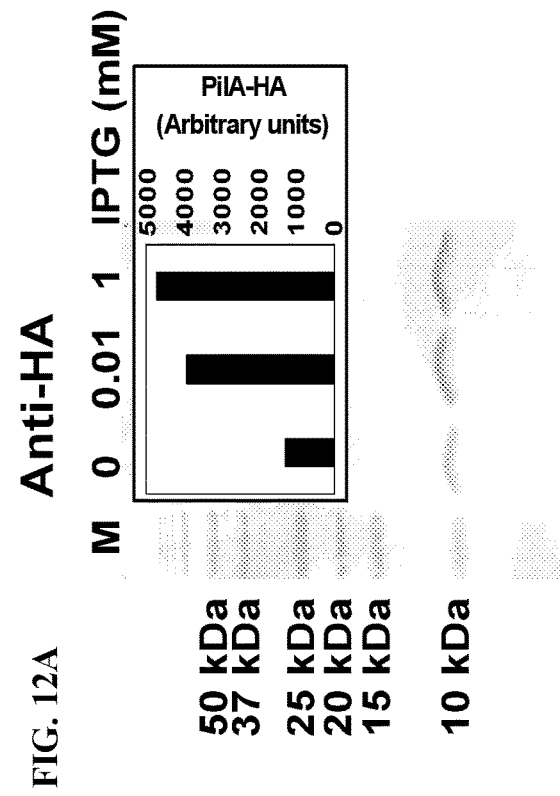
Figure 12D:
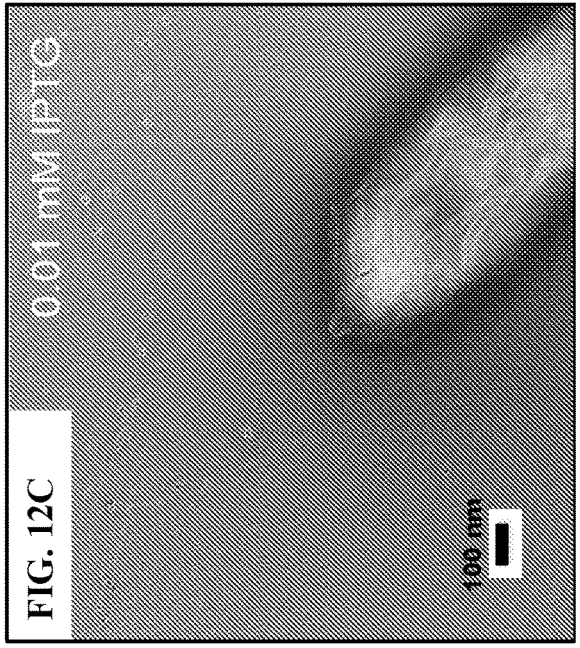

FIGS. 12A-12D depict the transcriptional control of PHA-HA expression and incorporation into e-PNs in strain PilA-WT/PilA-6His/PilA-HA evaluated with an anti-HA antibody. FIG. 12A is a Western blot of cell lysates. Lane M is the molecular weight standard markers. FIGS. 12B-12D are images showing immunogold labeling of HA-tag in e-PNs during growth in the absence or presence of the designated concentration of IPTG.

DETAILED DESCRIPTION

A description of example embodiments follows.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

The terminology used herein is for the purpose of describing particular embodiments only and is not intended to be limiting.

As used herein, the indefinite articles "a," "an" and "the" should be understood to include plural reference unless the context clearly indicates otherwise.

The terms "protein," "peptide" and "polypeptide" are used interchangeably herein to denote a polymer of at least two amino acids covalently linked by an amide bond, regardless of length or post-translational modification (e.g., glycosylation or phosphorylation). A protein, peptide or polypeptide can comprise any suitable L- and/or D-amino acid, for example, common a-amino acids (e.g., alanine, glycine, valine), non-a-amino acids (e.g., b-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in Organic Synthesis*," John Wiley and Sons, 1991. The functional groups of a protein, peptide or polypeptide can also be derivatized (e.g., alkylated) or labeled (e.g., with a detectable label, such as a fluorogen or a hapten) using methods known in the art. A protein, peptide or polypeptide can comprise one or more modifications (e.g., amino acid linkers, acylation, acetylation, amidation, methylation, terminal modifiers (e.g., cyclizing modifications), N-methyl-a-amino group substitution), if desired. In addition, a protein, peptide or polypeptide can be an analog of a known and/or naturally-occurring peptide, for example, a peptide analog having conservative amino acid residue substitution(s).

As used herein, the term "sequence identity," refers to the extent to which two nucleotide sequences, or two amino acid sequences, have the same residues at the same positions when the sequences are aligned to achieve a maximal level of identity, expressed as a percentage. For sequence alignment and comparison, typically one sequence is designated as a reference sequence, to which a test sequences are compared. The sequence identity between reference and test sequences is expressed as the percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide or amino acid residue at 70% of the same positions over the entire length of the reference sequence.

Alignment of sequences for comparison to achieve maximal levels of identity can be readily performed by a person of ordinary skill in the art using an appropriate alignment method or algorithm. In some instances, the alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Nat'l. Acad. Sci. USA* 85:2444 (1988), computerized implementations of these algorithms (GAP, BESTFIT, FASTA, and TFASTA in the Wisconsin Genetics Software Package, Genetics Computer Group, 575 Science Dr., Madison, Wis.), and visual inspection (see generally Ausubel et al., *Current Protocols in Molecular Biology*).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., 1990).

Fusion Proteins Comprising a Type IV Pilin Monomer and a Tag(s)

In one aspect, the present invention provides a fusion protein comprising a type IV pilin monomer and a tag. In some embodiments, the tag is at the C-terminus of the type IV pilin monomer.

The term "fusion protein" refers to a synthetic, semisynthetic or recombinant single protein molecule. A fusion protein can comprise all or a portion of two or more different proteins and/or peptides that are attached by covalent bonds (e.g., peptide bonds).

Fusion proteins of the invention can be produced recombinantly or synthetically, using routine methods and reagents that are well known in the art. For example, a fusion protein of the invention can be produced recombinantly in a suitable host cell (e.g., bacteria) according to methods known in the art. See, e.g., *Current Protocols in Molecular Biology*, Second Edition, Ausubel et al. eds., John Wiley & Sons, 1992; and *Molecular Cloning: a Laboratory Manual*, 2nd edition, Sambrook et al., 1989, Cold Spring Harbor Laboratory Press. For example, a nucleic acid molecule comprising a nucleotide sequence encoding a fusion protein described herein can be introduced and expressed in suitable host cell (e.g., *E. coli*), and the expressed fusion protein can be isolated/purified from the host cell (e.g., in inclusion bodies) using routine methods and readily available reagents. For example, DNA fragments coding for different protein sequences (e.g., a light-responsive domain, a heterologous peptide component) can be ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., Current Protocols in Molecular Biology, 1992).

In some embodiments, the fusion protein is encoded by a nucleic acid sequence that comprises SEQ ID NO: 12. In some embodiments, the fusion protein comprises, consists of, or consists essentially of SEQ ID NO: 13.

In some embodiments, the fusion protein is encoded by a nucleic acid sequence that comprises SEQ ID NO: 14. In some embodiments, the fusion protein comprises, consists of, or consists essentially of SEQ ID NO: 15.

In some embodiments, the fusion protein comprises, consists of, or consists essentially of SEQ ID NO: 16.

In some embodiments, the fusion protein comprises, consists of, or consists essentially of SEQ ID NO: 17.

In various embodiments, the fusion protein comprises a type IV pilin monomer. A "type IV pilin monomer" refers to a constituent part of a type IV pilus structure that can made by several different species of bacteria. The term "type IV pilin monomer" encompasses naturally occurring (e.g., wildtype) and artificial (e.g, variant, truncated) type IV pilin monomers. One of ordinary skill in the art to which this invention pertains can readily identify type IV pilin monomers from any of several bacterial species that make type IV pili.

In some embodiments, the type IV pilin monomer is selected from the group consisting of PilA, PilE, GspG, EspG, OxpG, NE1308, SO0854, PulG, HofG, Yts1G, and combinations thereof. Additional non-limiting examples of type IV pilin monomers include type IV pilin monomers from *Geobacter metallireducens* (SEQ ID NO: 18), *Calditerrivibrio nitroreducens* (SEQ ID NO: 19), *Desulfurvibrio alkaliphilus* (SEQ ID NO: 20), *Felxistipes sinusarabici* (SEQ ID NO: 21), *Synthrophus aciditrophicus* (SEQ ID NO: 22), *Syntrophus gentianae* (SEQ ID NO: 23), *Smithella* sp. F21 (SEQ ID NO: 24), *Syntrophobacter fumaroxidans* (SEQ ID NO: 25), *Syntrophobacter* sp. DG_60 (SEQ ID NO: 26), *Syntrophobacter* sp. SbD1 (SEQ ID NO: 27), *Syntrophorhabdus aromaticivorans* (SEQ ID NO: 28), *Desulfatibacillum alkenivorans* (SEQ ID NO: 29), *Syntrophomonas zehnderi* (SEQ ID NO: 30), *Syntrophaceticus schinkii* (SEQ ID NO: 31), *Tepidanaerobacter acetatoxydans* (SEQ ID NO: 32), *Thermacetogenium phaeum* (SEQ ID NO: 33), or a combination thereof (Table 2).

In some embodiments, the type IV pilin monomer comprises, consists of, or consists essentially of a sequence selected from the group consisting of SEQ ID NOs: 18-33

(Table 2). In some embodiments, the type IV pilin monomer has an amino acid sequence that has at least 80% sequence identity to a sequence selected from the group consisting of SEQ ID NOs: 18-33 (Table 2). In some embodiments, the type IV pilin monomer has an amino acid sequence that has at least 85%, at least 90%, at least 95%, at least 98%, or about 99%, sequence identity to a sequence selected from the group consisting of SEQ ID NOs: 18-33 (Table 2).

In some embodiments, the type IV pilin monomer is a wildtype type IV pilin monomer produced in a gram-negative bacterium. In some embodiments, the type IV pilin monomer is a variant of the wildtype type IV pilin monomer produced in a gram-negative bacterium. In some embodiments, the variant comprises an amino acid sequence that has at least 80% sequence identity to the amino acid sequence of a wildtype type IV pilin monomer. In some embodiments, the type IV pilin monomer variant comprises an amino acid sequence that has at least 85%, at least 90%, at least 95%, at least 98%, or about 99%, sequence identity to the amino acid sequence of a wildtype type IV pilin monomer.

In some embodiments, the type IV pilin monomer is the wildtype *Geobacter sulfurreducens* PilA monomer (SEQ ID NO: 2) (Table 1).

In some embodiments, the type IV pilin monomer is a variant of the wildtype *Geobacter sulfurreducens* PilA monomer (SEQ ID NO: 2).

In some embodiments, the variant of the wildtype *Geobacter sulfurreducens* PilA monomer is a N-terminal truncation lacking from 1-5 (e.g., 1, 2, 3, 4, or 5) amino acids at the N-terminus of the wildtype *Geobacter sulfurreducens* PilA (SEQ ID NO: 2). In some embodiments, the variant is a C-terminal truncation lacking from 1-5 (e.g., 1, 2, 3, 4, or 5) amino acids at the C-terminus of the wildtype *Geobacter sulfurreducens* PilA (SEQ ID NO: 2). In some embodiments, the variant is a N-terminal addition having from 1-5 (e.g., 1, 2, 3, 4, or 5) additional amino acids at the N-terminus of the wildtype *Geobacter sulfurreducens* PilA (SEQ ID NO: 2).

In some embodiments, the variant of the wildtype *Geobacter sulfurreducens* PilA monomer comprises an addition of an aromatic amino acid to the wildtype *Geobacter sulfurreducens* PilA (SEQ ID NO: 2). In some embodiments, about 1-10 aromatic amino acids are added to SEQ ID NO: 2. The number of aromatic amino acids added in SEQ ID NO: 2 may be 1, 2, 3, 4, 5, 6, 7, 8, 9 or 10 amino acids; at least 1, 2, 3, 4, 5, 6, 7, 8 or 9 amino acids; or about 1-8, about 2-8, about 2-6, about 3-6 or about 4-6 amino acids.

In some embodiments, the variant of the wildtype *Geobacter sulfurreducens* PilA monomer comprises a deletion of one or more aromatic amino acids in the wildtype *Geobacter sulfurreducens* PilA (SEQ ID NO: 2). In some embodiments, about 1-10 aromatic amino acids are deleted from SEQ ID NO: 2. The number of aromatic amino acids deleted in SEQ ID NO: 2 may be 1, 2, 3, 4, 5, 6, 7, 8, 9 or 10 amino acids; at least 1, 2, 3, 4, 5, 6, 7, 8 or 9 amino acids; or about 1-8, about 2-8, about 2-6, about 3-6 or about 4-6 amino acids.

In some embodiments, the variant of the wildtype *Geobacter sulfurreducens* PilA monomer comprises a substitution of an aromatic amino acid. In some embodiments, about 1-10 aromatic amino acids are substituted in SEQ ID NO: 2. The number of aromatic amino acids substituted in SEQ ID NO: 2 may be 1, 2, 3, 4, 5, 6, 7, 8, 9 or 10 amino acids; at least 1, 2, 3, 4, 5, 6, 7, 8 or 9 amino acids; or about 1-8, about 2-8, about 2-6, about 3-6 or about 4-6 amino acids. In some embodiments, the aromatic amino acid is substituted with a non-aromatic amino acid (e.g., alanine (A)). In some embodiments, the aromatic amino acid is substituted with a different aromatic amino acid (e.g., phenylalanine (F)-to-tryptophan (W) or tyrosine (Y)-to-W).

In some embodiments, the deleted or substituted aromatic amino acid is F24, F51, Y27, Y32, Y57, or a combination thereof in SEQ ID NO: 2. In some embodiments, the substitution is F24A, F51A, Y27A, Y32A, Y57A, or a combination thereof in SEQ ID NO: 2. In some embodiments, the substitution is F24W, F51W, Y27W, Y32W, Y57W, or a combination thereof in SEQ ID NO: 2.

In some embodiments, the variant of the wildtype *Geobacter sulfurreducens* PilA monomer comprises a substitution of a non-aromatic amino acid with an aromatic amino acid. In some embodiments, about 1-10 non-aromatic amino acids are substituted in SEQ ID NO: 2. The number of non-aromatic acids substituted in SEQ ID NO: 2 may be 1, 2, 3, 4, 5, 6, 7, 8, 9 or 10 amino acids; at least 1, 2, 3, 4, 5, 6, 7, 8 or 9 amino acids; or about 1-8, about 2-8, about 2-6, about 3-6 or about 4-6 amino acids.

In some embodiments, the type IV pilin monomer comprises an amino acid sequence that has at least 80% sequence identity to the amino acid sequence of wildtype *Geobacter sulfurreducens* PilA (SEQ ID NO: 2). In some embodiments, the type IV pilin monomer comprises an amino acid sequence that has at least 85%, at least 90%, at least 95%, at least 98%, or about 99%, sequence identity to the amino acid sequence of wildtype *Geobacter sulfurreducens* PilA (SEQ ID NO: 2).

In various embodiments, the fusion protein comprises a tag at the C-terminus of a type IV pilin monomer. As used herein, the term "tag" refers to one or more amino acids that are covalently attached to a type IV pilin monomer (e.g., at the C-terminus of a type IV pilin monomer). In some embodiments, the tag is covalently attached to a type IV pilin monomer by a peptide bond.

In some embodiments, the tag is a single amino acid. In some embodiments, the single amino acid is cysteine.

In some embodiments, the peptide tag has a length of about (e.g., consists of) 2-200 amino acids, e.g., about 2-180, about 3-180, about 3-160, about 4-160, about 4-140, about 5-140, about 5-120, about 6-120, about 6-100, about 7-100, about 7-80, about 8-80, about 8-60, about 9-60, about 9-50, about 10-50, about 10-40, about 12-40, about 12-35, about 15-35, about 15-30, or about 20-30 amino acids. In some embodiments, the peptide tag consists of about 2-100 amino acids, e.g., about 2-90, about 3-90, about 3-80, about 4-80, about 4-70, about 5-70, about 5-60, about 6-60, about 6-50, about 7-50, about 7-40, about 8-40, about 8-30, about 9-30, about 9-20, or about 10-20 amino acids. In some embodiments, the peptide tag consists of about 2-50 amino acids. In some embodiments, the peptide tag consists of about 5-15 amino acids.

In some embodiments, the tag is a peptide. In some embodiments, the peptide tag comprises, consists of, or consists essentially of a polyhistidine sequence, for example, 2-10 consecutive histidine amino acids, e.g., a 2×His tag, 3×His tag, 4×His tag (SEQ ID NO: 3), 5×His tag (SEQ ID NO: 4), 6×His (SEQ ID NO: 5), 7×His tag (SEQ ID NO: 6), 8×His tag (SEQ ID NO: 7), 9×His tag (SEQ ID NO: 8), or 10×His tag (SEQ ID NO: 9). In some embodiments, the peptide tag comprises, consists of, or consists essentially of a 6×His tag (SEQ ID NO: 5).

In some embodiments, the peptide tag comprises, consists of, or consists essentially of HHHHHHC (SEQ ID NO: 10).

In some embodiments, the peptide tag comprises, consists of, or consists essentially of a human influenza hemagglutinin (HA) sequence (SEQ ID NO: 11).

In some embodiments, the peptide tag comprises or consists of a binding motif. Non-limiting examples of the binding motif include nucleic acid (e.g., DNA or RNA)-binding sequences, protein-binding sequences (e.g., an epitope tag or calmodulin binding protein (CBP)), and chemical-binding sequences, etc. Non-limiting examples of epitope tags include HA, FLAG, AU1, AUS, Myc, Glu-Glu, OLLAS, T7, V5, VSV-G, E-Tag, S-Tag, Avi, HSV, KT3, and TK15, etc. Non-limiting examples of chemical-binding sequences include 6His, beta-galactosidase, Strep-tag, Strep-tag II, maltose binding protein, glutathione S transferase (GST), etc. Additional non-limiting examples of tags can be found in Table 3.

Electrically Conductive Nanowires

The fusion proteins described herein can be joined covalently (e.g., by peptide bonds) to one another to make a polymer. The resultant polymer is referred to herein as a nanowire. In various embodiments, the nanowire is an electrically conductive nanowire.

Accordingly, in another aspect, the present invention provides an electrically conductive nanowire, wherein the electrically conductive nanowire comprises one or more fusion proteins described herein.

In some embodiments, the electrically conductive nanowire comprises one fusion protein described herein. In some embodiments, the electrically conductive nanowire comprises at least 2 fusion proteins described herein, e.g., 2, 3, 4, 5, 6, 7, 8, 9 or 10; at least 3, 4, 5, 6, 7, 8 or 9; or about 2-10, about 2-8, about 2-6, about 3-6 or about 4-6 fusion proteins described herein.

In some embodiments, the electrically conductive nanowire further comprises one or more untagged type IV pilin monomers. The untagged type IV pilin monomer can be any one of the type IV pilin monomers described herein (e.g., a wildtype type IV pilin monomer, a N- or C-terminal truncation, a N-terminal addition, or a variant of the wildtype type IV pilin monomer). In some embodiments, the electrically conductive nanowire comprises one untagged type IV pilin monomer. In some embodiments, the electrically conductive nanowire comprises at least 2 untagged type IV pilin monomers, e.g., 2, 3, 4, 5, 6, 7, 8, 9 or 10; at least 3, 4, 5, 6, 7, 8 or 9; or about 2-10, about 2-8, about 2-6, about 3-6 or about 4-6 untagged type IV pilin monomers.

In some embodiments, the molar ratio of fusion protein to untagged type IV pilin monomer in the nanowire is in the range of about 2:1-1:20, e.g., about 2:1-1:18, about 3:2-1:18, about 3:2-1:15, about 1:1-1:15, about 1:1-1:10, about 1:1-1:9, about 1:1-1:8, about 1:1-1:7, about 1:1-1:6, about 1:1-1:5, about 1:1-1:4, about 1:1-1:3, or about 1:1-1:2. In some embodiments, the molar ratio of fusion protein to untagged type IV pilin monomer in the nanowire is at least 1:20, e.g., at least 1:18, at least 1:16, at least 1:15, at least 1:14, at least 1:12, at least 1:10, at least 1:9, at least 1:8, at least 1:7, at least 1:6, at least 1:5, at least 1:4, at least 1:3, at least 1:2, at least 1:1, at least 3:2, or at least 2:1. In some embodiments, the molar ratio of fusion protein to untagged type IV pilin monomer in the nanowire is in the range of about 20:1-1:20, e.g., about 20:1-1:18, about 18:1-1:18, about 18:1-1:16, about 16:1-1:16, about 16:1-1:14, about 14:1-1:14, about 12:1-1:14, about 12:1-1:12, about 10:1-1:12, about 8:1-1:10, about 8:1-1:8, about 6:1-1:8, about 6:1-1:6, about 4:1-1:6, about 4:1-1:4, about 2:1-1:4, about 2:1-1:2, or about 1:1-1:2. In some embodiments, the molar ratio of fusion protein to untagged type IV pilin monomer in the nanowire is in the range of about 10:1 to about 1:10. In some embodiments, the molar ratio of fusion protein to untagged type IV pilin monomer in the nanowire is in the range of about 1:1 to about 1:10.

In some embodiments, the electrically conductive nanowire contains no untagged type IV pilin monomers (e.g., the wire consists of fusion proteins described herein).

In some embodiments, a plurality of the tags (e.g., peptide tags) are surface exposed. In some embodiments, at least 2% of the tags (e.g., peptide tags), e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or 100% of tags (e.g., peptide tags) are surface exposed.

In some embodiments, the electrically conductive nanowire has a diameter of about 3-10 nm, e.g., about 3 nm, about 4 nm, about 5 nm, about 6 nm, about 7 nm, about 8 nm, about 9 nm, about 10 nm, about 3-9 nm, about 3-8 nm, about 3-7 nm, about 3-6 nm, or about 3-5 nm. In some embodiments, the electrically conductive nanowire has a diameter of from about 3-4 nm.

In some embodiments, the electrically conductive nanowire has a length of about 0.1-100 µm, e.g., about 0.2-100 µm, about 0.2-80 µm, about 0.3-80 µm, about 0.3-60 µm, about 0.4-60 µm, about 0.4-40 µm, about 0.5-40 µm, about 0.6-20 µm, about 0.6-18 µm, about 0.7-18 µm, about 0.7-16 µm, about 0.8-16 µm, about 0.8-14 µm, about 0.9-14 µm, about 0.9-12 µm, about 1-12 µm, about 1-10 µm, about 1.5-9 µm, about 1.5-8 µm, about 2-8 µm, about 2-6 µm, about 3-6 µm, or about 3-4 µm. In some embodiments, the electrically conductive nanowire has a length of about 0.5 µm to about 20 µm.

In some embodiments, the electrically conductive nanowire has a conductivity of about 10 µS/cm-500 S/cm (e.g., at about 25° C. and pH 7), e.g., about 20 µS/cm-500 S/cm, about 20 µS/cm-400 S/cm, about 30 µS/cm-400 S/cm, about 30 µS/cm-300 S/cm, about 40 µS/cm-200 S/cm, about 50 µS/cm-200 S/cm, about 50 µS/cm-100 S/cm, about 60 µS/cm-100 S/cm, about 60 µS/cm-50 S/cm, about 70 µS/cm-50 S/cm, about 80 µS/cm-20 S/cm, about 80 µS/cm-10 S/cm, about 90 µS/cm-10 S/cm, about 9 µS/cm-5 S/cm, or about 100 µS/cm-50 S/cm. In some embodiments, the electrically conductive nanowire has a conductivity of about 40 µS/cm to about 300 S/cm (e.g., at about 25° C. and pH 7).

Polynucleotides, Expression Vectors, Host Cells

In another aspect, the present invention provides a polynucleotide, wherein the polynucleotide encodes a fusion protein comprising a type IV pilin monomer and a tag, and wherein the tag is at the C-terminus of the type IV pilin monomer. The fusion protein, the type IV pilin monomer and the tag can be any of the fusion proteins, type IV pilin monomers and tags described herein. In some embodiments, the polynucleotide comprises a nucleotide sequence that is at least 70% identical to SEQ ID NO: 1, SEQ ID NO: 12 or SEQ ID NO: 14 (Table 1), e.g., at least 75%, at least 80%, at least 85%, at least 90%, at least 95%, at least 98%, or at least 99% identical to SEQ ID NO: 1, SEQ ID NO: 12 or SEQ ID NO: 14. In some embodiments, the polynucleotide comprises SEQ ID NO: 1, SEQ ID NO: 12 or SEQ ID NO: 14.

In another aspect, the present invention provides an expression vector comprising a polynucleotide. The polynucleotide is any one of the polynucleotides described herein. In some embodiments, the expression vector further comprises an expression control polynucleotide sequence operably linked to the polynucleotide, a polynucleotide sequence encoding a selectable marker, or both. In some embodiments, the expression control polynucleotide sequence comprises a promoter sequence, an enhancer sequence, or both. In some embodiments, the expression control polynucleotide sequence comprises an inducible promoter sequence. In some embodiments, transcription of the fusion protein can be regulated by an inducer. In some embodiments, the inducer is Isopropyl β-D-1-thiogalactopyranoside (IPTG).

The term "promoter" refers to a region of DNA to which RNA polymerase binds and initiates the transcription of a gene.

The term "operably linked" means that the nucleic acid is positioned in the recombinant polynucleotide, e.g., vector, in such a way that enables expression of the nucleic acid under control of the element (e.g., promoter) to which it is linked.

The term "selectable marker element" is an element that confers a trait suitable for artificial selection. Selectable marker elements can be negative or positive selection markers.

In another aspect, the present invention provides a host cell, wherein the host cell comprises a polynucleotide or an expression vector. The polynucleotide and the expression vector can be any of the polynucleotides and expression vectors described herein.

In some embodiments, the host cell is a bacterium. In some embodiments, the bacterium normally expresses type IV pili. In some embodiments, the bacterium is a Geobacter cell or a genetically modified Geobacter cell. In some embodiments, the bacterium is a *Geobacter sulfurreducens* cell or a genetically modified *Geobacter sulfurreducens* cell. In some embodiments, the bacterium is a *Geobacter sulfurreducens* KN400 cell or a genetically modified *Geobacter sulfurreducens* KN400 cell.

In some embodiments, the bacterium is an *Escherichia coli* cell or a genetically modified *Escherichia coli*. In some embodiments, the genetically modified *Escherichia coli* cell expresses a gene selected from the group consisting of: hofB, hofC, hofM, hofN, hofO, hovP, hofQ, ppdA, ppdB, ygdB, ppdC, gspO and combinations thereof.

In some embodiments, the bacterium is selected from the group consisting of: *Geobacter sulfurreducens, Escherichia coli, Geobacter metallireducens, Calditerrivibrio nitroreducens, Desulfurvibrio alkahphilus, Felxistipes sinusarabici, Synthrophus aciditrophicus, Syntrophus gentianae, Smithella* sp. F21, *Syntrophobacter fumaroxidans, Syntrophobacter* sp. DG_60, *Syntrophobacter* sp. SbD1, *Syntrophorhabdus aromaticivorans, Desulfatibacillum alkenivorans, Syntrophomonas zehnderi, Syntrophaceticus schinkii, Tepidanaerobacter acetatoxydans, Thermacetogenium phaeum*, or a genetically modified variant thereof.

In some embodiments, the polynucleotide is integrated into the chromosome of the bacterium (e.g., *Geobacter sulfurreducens* or *Escherichia coli*). In some embodiments, the polynucleotide is located on an extrachromosomal plasmid in the bacterium (e.g., *Geobacter sulfurreducens* or *Escherichia coli*).

In some embodiments, the host cell further comprises a polynucleotide encoding any one of the untagged type IV pilin monomer described herein. In some embodiments, the polynucleotide encoding the untagged type IV pilin monomer is integrated into the chromosome of the host cell. In some embodiments, the polynucleotide encoding the untagged type IV pilin monomer is located on an extrachromosomal plasmid in the host cell.

Methods of Producing Electrically Conductive Protein Nanowires

In another aspect, the present invention provides a method of producing the modified, electrically conductive protein nanowires described herein, comprising the steps of:
a) introducing a polynucleotide or an expression vector into a host cell;
b) placing the host cell in a culture medium conditioned for producing type IV pili;
c) culturing the host cell for a time sufficient to produce a desired quantity of the type IV pili; and
d) isolating the type IV pili from the culture medium, thereby producing the electrically conductive protein nanowires.

The electrically conductive protein nanowires, the polynucleotide, the expression vector, and the host cells employed in the method are as described herein.

In some embodiments, the culture medium comprises an Fe(III) compound. In some embodiments, the Fe(III) compound is Fe(III) oxide. In some embodiments, the culture medium comprises about 20 mM acetate and about 40 mM fumarate. In some embodiments, the host cell is cultured under an anaerobic condition at about 30° C. In some embodiments, the method further comprises culturing the host cell in the presence of an inducing molecule. In some embodiments, the inducing molecule is Isopropyl β-D-1-thiogalactopyranoside (IPTG).

In another aspect, the present invention provides *Geobacter sulfurreducens* PilA nanowires functionalized to include surface exposed peptide ligands are provided. In one embodiment, the nanowires are electrically conductive.

In another aspect, the present invention provides a method of making synthetic electrically conductive protein nanowires having surface exposed peptide ligands, the method including modifying the *Geobacter sulfurreducens* gene for the monomer that assembles into e-PNs to include peptide ligands at the carboxyl terminus of the monomer.

Nanowire Sensor Devices

In another aspect, the present invention provides a nanowire sensor device comprising:
an electrically conductive nanowire described herein, comprising one or more of the fusion proteins described herein;
a first electrode having a first electrode terminal;
a second electrode having a second electrode terminal;
an electrical resistance connected between the first and the second electrode terminals; and
an electrical current monitor in electrical communication with the electrical resistance,
wherein:
the first and second electrodes are each configured to support and are each in physical contact with the electrically conductive nanowire; and
the electrical current monitor is configured to measure an electrical current passing through the electrical resistance.

The electrically conductive nanowire in the sensor device can be any one of the electrically conductive nanowires described herein, comprising one or more of the fusion proteins described herein.

In some embodiments, the first electrode is an anode electrode configured to be imbedded in a material; and the second electrode is a cathode electrode in electrical contact with the material. In some embodiments, the first electrode is a cathode electrode configured to be imbedded in a material and the second electrode is an anode electrode in electrical contact with the materials.

In some embodiments, the material is a liquid (e.g., solution) or a solid.

In some embodiments, the nanowire sensor device measures the pH of the material. In some embodiments, the peptide tag can detect and/or quantify a chemical or biological analyte. Non-limiting examples of the analytes include aluminium, $Ca^{2+}$, Cobalt, $Cu^{2+}$, Fe—Pt Alloy, germania, $Hg^{2+}$, $Ni^{2+}$, palladium, $Pb^{2+}$, platinum, stainless steel, $Zn^{2+}$, $H_2O_2$, acetone, ATP, *Anthrax* protective antigen, atrazine, BRCA1, cardiac troponin I, caspase-3, carbonic anhydrase, CEA, DA, Dioxins, Dioxins and PCBs, diuron, EDCs Enterotoxin B, HA, hCG, HPV, Hydroxyapatite, IgY, methotrexate, MDB, MMP-2, MMP-7, myofibers, prolactin, porphyrin, PSA, streptavidin, substance P, TNF-α, TNT, VOCs, K562 cells, *Pseudomonas aeruginosa* whole cells, and SW620 metastatic cells, etc. Additional non-limiting examples of the analytes can be found in Table 3.

EXAMPLES

Fabrication of electrically conductive protein nanowires (e-PNs) with *G. sulfurreducens* offers tight, reproducible, and consistent control of nanowire structure and electronic properties, combined with the potential for broad possibilities in the design of e-PNs through genetic modification of the monomer peptide. For example, the conductivity of e-PNs produced with *G. sulfurreducens* have been tuned over six orders of magnitude (ca. 1 mS/cm to 1 kS/cm) by genetically manipulating the abundance of aromatic amino acids in the monomer peptide.

As described herein, a strategy for functionalizing e-PNs with surface-exposed peptide ligands has been developed. The *G. sulfurreducens* gene for the monomer that assembles into e-PNs was modified to add known peptide ligands at the carboxyl terminus of the monomer. Strains of *G. sulfurreducens* were constructed that fabricated synthetic e-PNs with a six-histidine 'His-tag' or both the His-tag and a nine-peptide 'HA-tag' exposed on the outer surface. The abundance in HA-tag in e-PNs was controlled by placing expression of the gene for the synthetic monomer with the HA-tag under inducible transcriptional regulation.

*G. sulfurreducens* express e-PNs containing monomers in which peptide ligands were added to the carboxyl terminus. The peptide ligands introduced are accessible on the outer surface of the e-PNs. The potential impact of the added peptide ligands on e-PN conductivity was studied. Addition of the peptide ligands did not diminish e-PN conductivity.

Thus, genetic modification of e-PN structure makes it feasible to decorate the outer surface of e-PNs with short peptides. The results also indicate that *G. sulfurreducens* e-PNs can be decorated with a diversity of outer surface peptide ligands to introduce new binding properties. The present disclosure suggests broad possibilities for tailoring e-PN properties for diverse applications.

Example 1. Methods and Materials

Strains and Growth Conditions

*G. sulfurreducens* strains were grown under anaerobic conditions at 30° C. in a defined medium with acetate as the electron donor and fumarate as the electron acceptor as previously described. *Escherichia coli* was cultivated with Luria-Bertani medium with or without antibiotics.

Construction of *G. sulfurreducens* PilA-WT/PilA-6His Strain

*G. sulfurreducens* PilA-WT/PilA-6His strain was constructed with *G. sulfurreducens* KN400. A gene for PilA-6His, the gene KN400_3442, which is located downstream of the PilA gene (KN400_1523) on the chromosome, and the putative transcription terminator were integrated at a non-coding region between KN400_0788 and KN400_0787 in the chromosome. The primer pair upKpnI (CTAGGTACCGTGGTGGACCCCCCTTACCGGT) (SEQ ID NO: 134) /upSpeI (CGAACTAGTTGTGACCGCTGCCGGCTCCG) (SEQ ID NO: 135) was used to amplify by PCR ca. 550 bp of KN400_0788 upstream of the integration site with the genomic DNA as template. This PCR product was digested with KpnI/SpeI and ligated with the vector pCR2.1GmrloxP 40, resulting in pCR2.1UP-GmrloxP. The 6His tag was fused to the C-terminal end of PilA by PCR with the primer pair PilAdnNotI (CACGCGGCCGCAAGAG-GAGCCAGTGACGAAAATC) (SEQ ID NO: 136) /PilA-CHis (GAGTTAGTGGTGGT-GGTGGTGGTGACTTTCGGGCGGATAGGTTTGATC) (SEQ ID NO: 137). For the construction of PilA-6His-KN400_3442, two PCR products were generated before being combined by recombinant PCR. PilA-6His was amplified with the primer pair PilAdnNotI/PilAHisrecup (CTCCAGTATGTATTTAATCAATT-AGTGGTGGTGGTGGTGGTG) (SEQ ID NO: 138) while KN400_3442 was amplified with the primer pair PilAHis-recdn (CACCACCACCACCACCACTAATTGAT-TAAATACATACTGGAG) (SEQ ID NO: 139) /GSU1497XhoIAvrII (CTGCTCGAGGATACCTAGGCT-ATTCCGACAACTACGAGAC) (SEQ ID NO: 140). The primer pair PilAdnNotI/GSU1497XhoIAvrII was then used to amplify PilA-6His-KN400_3442 by recombinant PCR. PilA-6His-KN400_3442 was cloned at NotI/XhoI sites in pCR2.1UP-GmrloxP downstream of GmrloxP, resulting in pCR2.1UP-GmrloxP-PilAHis-3442. The primer pair dnAvrII (CATCCTAGGAGGGCAGACATTGCG-GAACGT) (SEQ ID NO: 141) /dnXhoI (CATCTCGAGCGGGTTCCGCTGCCGTCGTAC) (SEQ ID NO: 142) was used to amplify by PCR ca. 530 bp of KN400_0787 downstream of the integration site. This PCR product was cloned at AvrII/XhoI sites in pCR2.1UP-Gmr-loxP-PilAHis-3442, resulting in pCR2.1UP-GmrloxP-PilA-His-3442-DN. The final plasmid was linearized with XhoI for transformation as previously described. Transformants were selected with the medium containing gentamicin (20 μg/ml) and were verified by PCR.

Construction of *G. sulfurreducens* PilA-WT/PilA-6his/PilA-HA Strain

*G. sulfurreducens* PilA-WT/PHA-6His/PHA-HA strain was constructed by introducing a gene encoding PilA monomer with the HA tag (PHA-HA) together with the gene KN400_3442 in the chromosome of the *G. sulfurreducens* PilA-WT/PHA-6His strain. The PHA-HA gene was amplified by PCR with a primer pair TCTGGATCCAGGAGGA-GACACTTATGCTTCAGAAAC/GTATTTAATCAAT-TACGCGTAGTCCGGCACGTCGTACGG-GTAACTTTCGGGCGGATAG (SEQ ID NO: 143). The gene KN400_3442 was amplified by PCR with a primer pair CTATCCGCCCGAAAGT-TACCCGTACGACGTGCCGGACTACGCGTAATTGAT-TAAATAC (SEQ ID NO: 144) /TCTGAATTCCGA-TATGACTACTGCGAC (SEQ ID NO: 145). The PHA-HA gene and the KN400_3442 gene were connected by PCR with a primer pair TCTGGATCCAGGAGGAGACACT-TATGCTTCAGAAAC/TCTGAATTCCGATATGAC-TACTGCGAC (SEQ ID NO: 146). The PCR product of PHA-HA/KN400_3442 was digested with BamHI/EcoRI and cloned in the plasmid pKIkan, which is a derivative of pKIapr and has a kanamycin-resistance gene instead of the apramycin-resistance gene. The sequences of KN400_1082 and 1083 used for homologous recombination for introduction of PHA-HA/KN400_3442 are same as those of GSU1106 and 1107 for homologous recombination sequences in pKIkan, respectively. The plasmid thus constructed was linearized with XhoI for electroporation.

Western Blot Analysis

The wild-type, PilA-WT/PHA-6His, and PilA-WT/PHA-6His/PHA-HA strains were grown with acetate and fumarate at 25° C. IPTG was added at 1 mM for the PHA-WT/PHA-6His/PHA-HA strain with the exception of the study of the impact on IPTG concentrations on incorporation of PHA-HA in filaments. Cell extracts were prepared with B-PER Complete Bacterial Protein Extraction Reagent (Thermo Fisher Scientific) and the amount of protein was measured with the Bradford Protein Assay (Bio-Rad) as instructed by the manufacturer. Cell extracts were separated on 16.5% Tris-Tricine gel (Bio-Rad). An anti-PilA antibody was obtained against peptide, ESAFADDQTYPPES (SEQ ID NO: 147), corresponding to the C-terminal end of PilA (New England Peptide). An anti-6His antibody (6x-His Tag Polyclonal Antibody) and an anti-HA antibody (HA Tag Polyclonal Antibody) were purchased from Invitrogen. Western blot analysis was conducted as described previously. (Leang, C.; Qian, X.; Mester, T.; Lovley, D. R., Alignment of the c-type cytochrome OmcS along pili of *Geobacter sulfurreducens*. Appl Environ Microbiol 2010, 76, 4080-4084.)

Immunogold Labeling

The strains were grown with acetate and fumarate at 25° C. The PilA-WT/PilA-6His/PilA-HA strain was grown with 1 mM IPTG unless otherwise specified. Immunogold labeling was conducted as previously described. (Leang, C.; Qian, X.; Mester, T.; Lovley, D. R., Alignment of the c-type cytochrome OmcS along pili of *Geobacter sulfurreducens*. Appl Environ Microbiol 2010, 76, 4080-4084.) For immunogold labeling of just one type of ligand, the 6x-His Tag Polyclonal Antibody or HA Tag Polyclonal Antibody was the primary antibody and the anti-rabbit IgG-gold (10 nm) antibody (Sigma-Aldrich) was the secondary. Dual immunogold labeling was conducted with 6x-His Tag Monoclonal Antibody (Invitrogen) and the HA Tag Polyclonal Antibody as primary antibodies and an anti-mouse IgG-gold (40 nm) antibody (40 nm Goat Anti-Mouse IgG gold conjugate, Expedeon) and the anti-rabbit IgG-gold (10 nm) antibody as secondary antibodies. Samples were examined with transmission electron microscopy.

$Ni^{2+}$-Binding Assay

The wild-type and PilA-WT/PilA-6His strains were grown with acetate and fumarate at 25° C. $Ni^{2+}$-binding assay was conducted with Ni-NTA-Nanogold (5 nm) (Nanoprobes). Seven μl of the culture was placed on a copper grid and incubated for 5 min. The grid was floated upside down in phosphate-buffered saline (PBS) for 5 min, in PBS containing 3% bovine serum albumin (BSA) and 40 mM imidazole for 15 min, and in PBS containing 0.3% BSA, 40 mM imidazole, and the Ni-NTA-Nanogold for 30 min at room temperature. The grid was washed with PBS containing 40 mM imidazole three times and with water once. Samples were stained with 2% uranyl acetate and examined by transmission electron microscopy.

Current Production

The capacity to produce current was determined in the two-chambered H-cell system with a continuous flow of medium with acetate (10 mM) as the electron donor and graphite stick anode (65 cm$^2$) poised at 300 mV versus Ag/AgCl as the electron acceptor.

Conductance of Individual e-PNs

An aliquot (100 μl) of cell culture was drop-cast onto highly oriented pyrolytic graphite (HOPG). Conducting probe atomic force microscopy was preformed using an Oxford Instruments/Asylum Research Cypher ES atomic force microscope with a Pt/Ir-coated Arrow-ContPT tip (NanoWorld AG, Neuchâtel, Switzerland). Topographical imaging was performed in contact mode with a force of 0.1 nN. Point-mode current response (I-V) spectroscopy was achieved by applying a 1 nN force to the top of the wire and conducting quadruplicate voltage sweeps of −0.6-0.6 V at 0.99 Hz. The voltage sweep was averaged for each of the I-V curves and conductance was calculated from the linear portion of the I-V curve (−0.2-0.2 V). Average conductance and standard deviation were calculated using 3 independent points on 3 independent e-PNs of each strain. Average height and standard deviation were calculated from 6 independent points on 3 independent e-PNs.

Example 2. Wires Decorated with Histidine Ligand

To evaluate displaying peptide ligands on the outer surface of e-PNs, the wild-type *G. sulfurreducens* gene for the pilin monomer (PilA) was modified to encode six histidines (i.e., a 'His-tag') at the carboxyl end. FIG. 1 shows the DNA sequence of wild-type pilA, pilA-6His, and pilA-HA genes. Sequences for the His-tag and HA-tag are indicated in solid and dashed underline, respectively.

Figures 2A, 2B, 2C:
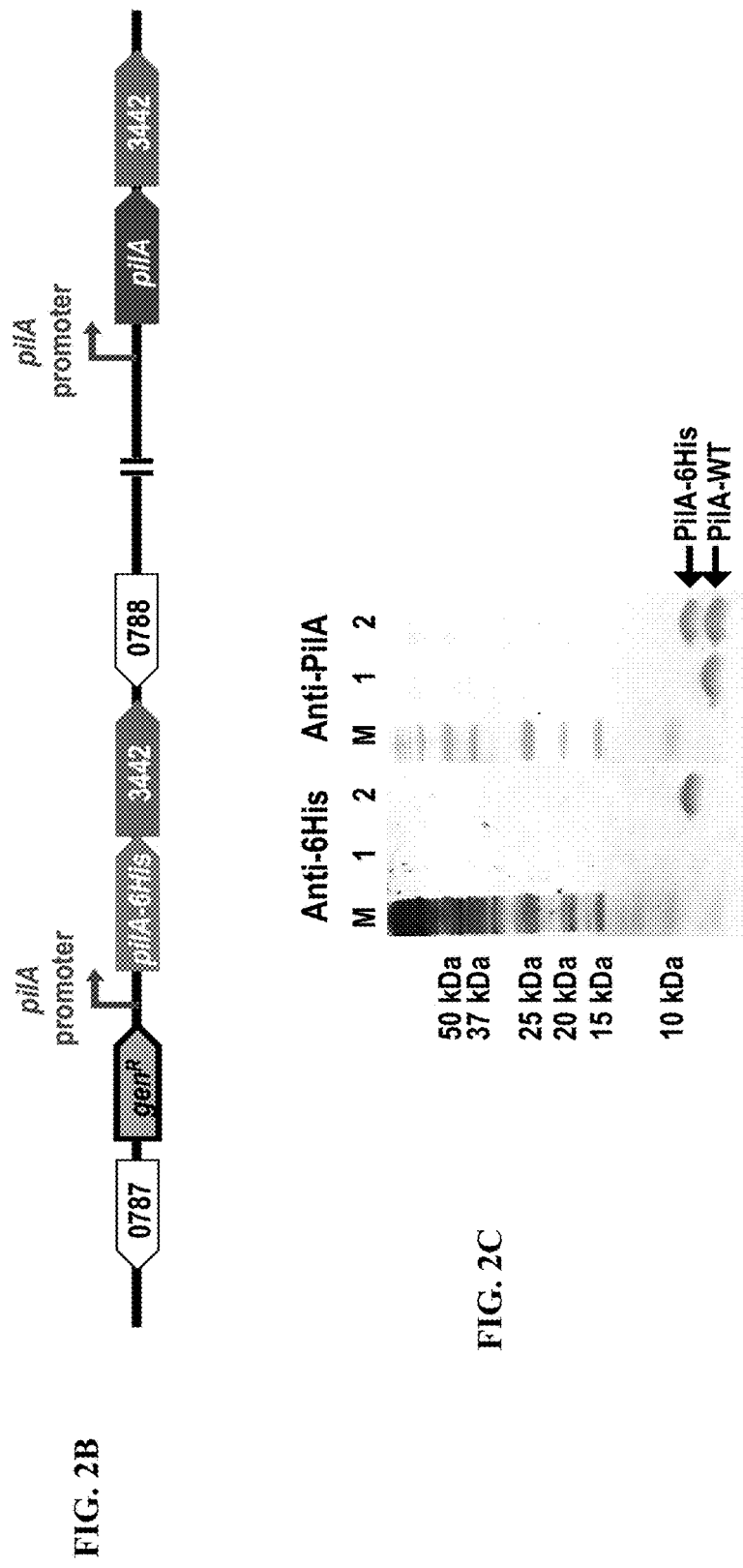
FIGS. 2A-2C depict construction of *G. sulfurreducens* strain PilA-WT/PilA-6His and expression of pilin monomers.

FIG. 2A shows the amino acid sequence of the wild-type PilA and of the PHA-6His. As shown in FIG. 2B, the synthetic gene was inserted into the chromosome of *G. sulfurreducens* strain KN400, along with the gene for the protein Spc (gene KN400_3442) that may be required for pilin monomer stability. The resultant strain, which contained genes for the wild-type PilA as well as the histidine-modified PilA pilin monomer (PilA-6His), was designated strain PilA-WT/PilA-6His. Western blot analysis with anti-6His antibody of cell lysates of strain PilA-WT/PilA-6His separated with SDS-PAGE revealed a single protein band at the molecular weight expected for the PilA-6His monomer (FIG. 2C). There was no corresponding band in lysates of wild-type cells. Western blot analysis with antibody that detected wild-type PilA detected a single band in wild-type cell lysates and two bands in lysates of strain PilA-WT/PilA-6His (FIG. 2C). The additional band in the strain PHA-WT/PilA-6His lysate was positioned at the higher molecular weight position detected with the anti-6His antibody.

Figure 4C:
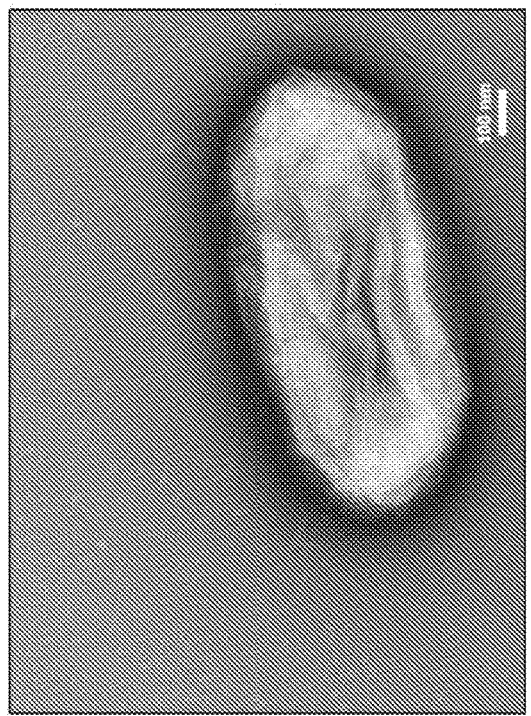
Figure 4D:
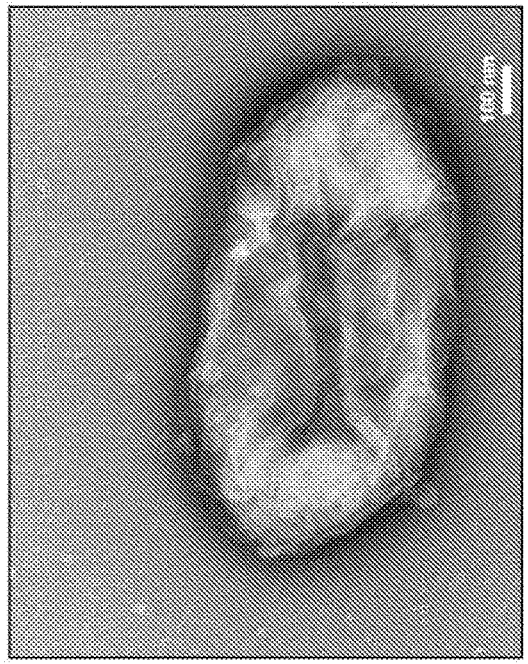
Figure 4A:
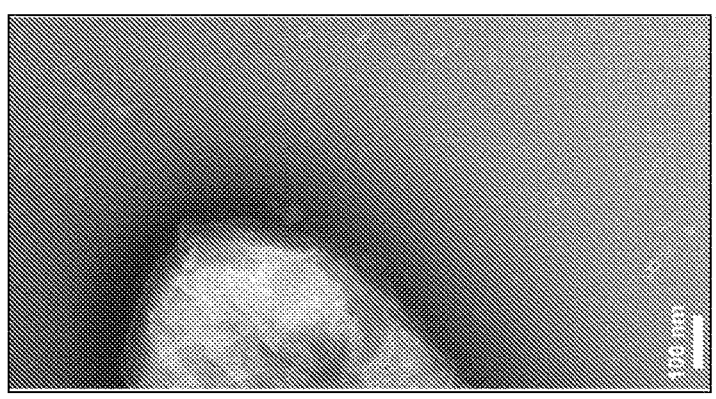
Figure 4B:
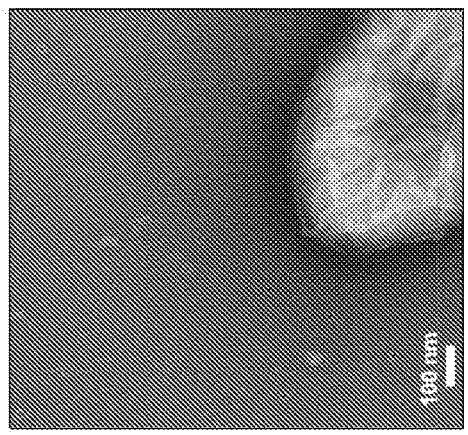

Referring to FIGS. 3A-3B, transmission electron microscopy of cells labeled with the anti-6His antibody and a secondary antibody conjugated with gold revealed abundant His-tag loci along the wires that were accessible to the antibody. As shown in FIGS. 4A-4B, there was no gold labeling of wild-type cells.

When strain PilA-WT/PHA-6His cells were treated with a $Ni^{2+}$-NTA-gold reagent designed to label His-tags, the gold nanoparticles were specifically localized along the wires (FIGS. 3C-3E). As shown in FIGS. 4C-4D, wild-type cells were not labeled. These results further demonstrate that the His-tag ligand was accessible on the outer surface of the wires.

*G. sulfurreducens* can only produce high current densities on graphite electrodes if its pili are electrically conductive. *G. sulfurreducens* strain PilA-WT/PHA-6His produced maximum currents comparable to the wild-type strain with just a slightly longer lag in the initiation of current production (FIG. 5). This result indicates that introducing the His-tag did not substantially decrease pili conductivity.

Conductivity of individual wires was more directly evaluated with conducting tip atomic force microscopy. The wires were readily identified in topographical imaging in contact mode and had a diameter of 3.1+0.3 nm (mean+standard deviation; n=18, 6 points on 3 wires). The conductive tip was lightly applied to the top of the wire (1 nN), and point-mode current response (I-V) spectroscopy revealed a conductance of 7.2+1.5 nS (mean+standard deviation; n=9) (FIGS. 6 and 7). This is comparable to previously observed conductance of 4.5+0.3 nS for e-PNs comprised solely of the wild-type monomer and much higher than the previously reported conductance of the e-PNs from strain *G. sulfurreducens* strain Aro-5, which lacks key aromatic amino acids required for high conductivity.

Example 3. Wires Decorated with Two Different Peptide Ligands

To determine whether two peptide ligands with different functions could be displayed on one e-PN, a gene (FIG. 1) encoding the nine-peptide 'HA-tag' (YPYDVPDYA) (SEQ ID NO: 15) at the carboxyl end of the wild-type PilA pilin monomer (FIG. 8A) was incorporated into the chromosome along with the PilA-6His and wild-type (WT) genes (FIG. 8B). The gene for the PilA with the HA-tag (PHA-HA) was located downstream of the IPTG-inducible lac promoter/operator to provide the option of controlling the stoichiometry of incorporation of the PHA-HA monomer in the e-PNs (FIG. 8B). This strain was designated *G. sulfurreducens* strain PilA-WT/PHA-6His/PHA-HA. Western blot analysis demonstrated that, in the presence of 1 mM IPTG, monomers of WT-PilA, PHA-6His, and PHA-HA were expressed in this strain (FIG. 8C).

Immunogold labeling for just the His-tag (FIGS. 9A-9B) or the HA-tag (FIGS. 9C-9D) demonstrated that both tags were abundant in the e-PNs from strain PilA-WT/PilA-6His/PilA-HA grown with 1 mM IPTG. Dual labeling with secondary antibodies with different size gold particles demonstrated that both tags were present in the same e-PNs (FIGS. 9E-9F). e-PNs of strain PilA-WT/PilA-6His cells were not immunogold labeled with the anti-HA antibody (FIG. 10). The current production of strain PilA-WT/PilA-6His/PilA-HA was similar to that of strain PilA-WT/PilA-6His, indicating the addition of the HA-tag did not significantly diminish pili conductivity (FIG. 5). Analysis of individual e-PNs of strain PilA-WT/PilA-6His/PilA-HA (FIGS. 5 and 11A-11C) yielded higher currents at equivalent applied voltages than observed with the e-PNs with just the His-tag, with an estimated conductance of 27.2+1.0 nS (n=9). A potential explanation for this is that the HA-tag contains multiple aromatic amino acids, which may promote electron transport.

Some PHA-HA was expressed in strain PilA-WT/PilA-6His/PilA-HA even in the absence of the IPTG inducer (FIG. 12A). However, the concentration of PHA-HA monomer in the cells was greater with added IPTG (FIG. 12A). Increased pools of PHA-HA were associated with e-PNs that labeled more heavily with immunogold labeling for the HA-tag (FIGS. 12B-12D). These results demonstrate that it is possible to control the abundance of a specific peptide ligand displayed on e-PNs with transcriptional control of the expression of the monomer with that ligand.

The results demonstrate that e-PNs produced with *G. sulfurreducens* can be decorated with one or more peptide ligands while maintaining or increasing their conductivity. The stoichiometry of ligand density can be controlled with transcriptional regulation. These capabilities greatly expand the potential applications of e-PNs in electronic devices and for the fabrication of electrically conductive composite materials.

For example, sensors developed from other nanowire materials can provide highly sensitive and specific, real-time electrical response for detection of diverse chemicals and biologics. Analytes of interest are detected as a change in nanowire conductivity that results from changes in pH associated with the activity of enzymes incorporated into the sensors, or binding of analytes to nanowires functionalized with antibodies, peptides, or other ligands. The conductivity of *G. sulfurreducens* e-PNs have already been shown to be highly responsive to pH. Short peptides for binding enzymes and antibodies displayed on the outer-surface of e-PNs could be an effective method for functionalizing e-PN-based sensors. Furthermore, peptides can be designed to function as ligands for a wide diversity of chemical and biological analytes or to enhance attachment to cells. Thus, the simplicity of modifying the peptides displayed on e-PNs and controlling the abundance of peptide display provide unprecedented flexibility in nanowire sensor design not readily achieved with other nanowire materials. In a similar manner modifying the surface chemistry of e-PNs with short peptides or unnatural amino acids may enable chemical linkages with polymers or enhance binding to materials to aid in e-PN alignment in electronic devices.

Peptides of up to 9 amino acids can be added to the 61-amino acid monomer backbone of *G. sulfurreducens* e-PNs. However, much larger peptide can be used to decorate e-PNs because the monomers of other conductive pili have an N-terminal end homologous to the *G. sulfurreducens* monomer, but are comprised of over 100 amino acids. These broad possibilities for modifying e-PNs with peptides coupled with the advantages of e-PNs as a "green" sustainable material can lead to the development of e-PN-based electronic devices and materials.

While example embodiments have been particularly shown and described, it will be understood by those skilled in the art that various changes in form and details may be made therein without departing from the scope of the embodiments encompassed by the appended claims.

TABLE 1

*Geobacter sulfurreducens* PilA, Tag, and Fusion Protein Sequences

Wildtype *Geobacter sulfurreducens* PilA DNA and Protein Sequences

SEQ ID NO: 1
ATGCTTCAGAAACTCAGAAACAGGAAAGGTTTCACCCTTATCGAG
CTGCTGATCGTCGTTGCGATCATCGGTATTCTCGCTGCAATTGCG
ATTCCGCAGTTCTCGGCGTATCGTGTCAAGGCGTACAACAGCGCG
GCGTCAAGCGACTTGAGAAACCTGAAGACTGCTCTTGAGTCCGCA
TTTGCTGATGATCAAACCTATCCGCCCGAAAGTTAA

SEQ ID NO: 2
FTLIELLIVVAIIGILAAIAIPQFSAYRVKAYNSAASSDLRNLKT
ALESAFADDQTYPPES

Example Histidine (His) Tags

SEQ ID NO: 3
HHHH

SEQ ID NO: 4
HHHHH

SEQ ID NO: 5
HHHHHH

TABLE 1-continued

Geobacter sulfurreducens PilA, Tag, and Fusion Protein Sequences

SEQ ID NO: 6    HHHHHH

SEQ ID NO: 7    HHHHHHH

SEQ ID NO: 8    HHHHHHHH

SEQ ID NO: 9    HHHHHHHHH

SEQ ID NO: 10   HHHHHHC

Human Influenza Hemagglutinin (HA) Tag

SEQ ID NO: 11   YPYDVPDYA

Geobacter sulfurreducens PilA-6His Fusion Protein

SEQ ID NO: 12   ATGCTTCAGAAACTCAGAAACAGGAAAGGTTTCACCCTTATCGAG
CTGCTGATCGTCGTTGCGATCATCGGTATTCTCGCTGCAATTGCG
ATTCCGCAGTTCTCGGCGTATCGTGTCAAGGCGTACAACAGCGCG
GCGTCAAGCGACTTGAGAAACCTGAAGACTGCTCTTGAGTCCGCA
TTTGCTGATGATCAAACCTATCCGCCCGAAAGTCACCACCACCAC
CACCACTAA

SEQ ID NO: 13   FTLIELLIVVAIIGILAAIAIPQFSAYRVKAYNSAASSDLRNLKT
ALESAFADDQTYPPESHHHHHH

Geobacter sulfurreducens PilA-HA Fusion Protein

SEQ ID NO: 14   ATGCTTCAGAAACTCAGAAACAGGAAAGGTTTCACCCTTATCGAG
CTGCTGATCGTCGTTGCGATCATCGGTATTCTCGCTGCAATTGCG
ATTCCGCAGTTCTCGGCGTATCGTGTCAAGGCGTACAACAGCGCG
GCGTCAAGCGACTTGAGAAACCTGAAGACTGCTCTTGAGTCCGCA
TTTGCTGATGATCAAACCTATCCGCCCGAAAGTTACCCGTACGAC
GTGCCGGACTACGCGTAA

SEQ ID NO: 15   FTLIELLIVVAIIGILAAIAIPQFSAYRVKAYNSAASSDLRNLKT
ALESAFADDQTYPPESYPYDVPDYA

Geobacter sulfurreducens PilA-Cys Fusion Protein

SEQ ID NO: 16   FTLIELLIVVAIIGILAAIAIPQFSAYRVKAYNSAASSDLRNLKT
ALESAFADDQTYPPEC

Geobacter sulfurreducens PilA-6His-Cys Fusion Protein

SEQ ID NO: 17   FTLIELLIVVAIIGILAAIAIPQFSAYRVKAYNSAASSDLRNLKT
ALESAFADDQTYPPESHHHHHHC

TABLE 2

Non-limiting Examples of Type IV Pilin Monomer Sequences

Geobacter metallireducens

SEQ ID NO: 18   FTLIELLIVVAIIGILAAIAIPQFAAYRQKAFNSAAESD
LKNTKTNLESYYSEHQFYPN

Calditerrivibrio nitroreducens

SEQ ID NO: 19   FTLIELLVVAIIAILAAIAIPQFAKYRENAAKASAVAD
AKNIATAIESYYADTQSFPSSISDGSIVPLGTQTFSLSK
NNSFKGYYYNNPSYTFVVSNTAFNRSVTFNSATGGVDVN
VW

Desulfurvibrio alkaliphilus

SEQ ID NO: 20   FTLVELMIVVAIIGILAAVAIPQFAQYRIRGFNSSALSD
VRNLTTAQEAFFADWLRYAVTHEAADVTEVKATGDLLEG
PSTGAMVLAQWARQAHQQLPLAIGNGVVMQADVIPATAV
SYVAISKHLQGNTMYGATNTSTAIHRDQETLVPGQGGDV
LPITGYMPEPHETDDPFIDHEEFEAQ

Felxistipes sinusarabici

SEQ ID NO: 21   FTLIELLVVVAIIGILAAIAIPQFAKYRINAFNSAAQSD
LANVKSALESYYAENFTYPSP

Synthrophus aciditrophicus

SEQ ID NO: 22   FTLIELMIVIAIIGILAAIAIPQFQQYRTRGYNTAAKAD
AKNAYTAAQAYFSDHPSVTISSITDLANYGFKASADVTT
TAAGDMDGLAITAKHSASDTTYQVDSQGTITP

Syntrophus gentianae

SEQ ID NO: 23   FTLIELMIVIAIIGILAAIAIPQFTQYRKRAYDASSKAD
LKSAYTAAQAWFNDNPSGTLPAATITSATTTGELPGNGF
KASTGVTATVTSGTMGTFSIATTHSQGTKTYNITAGGTL
TES

Smithella sp. F21

SEQ ID NO: 24   FTLIELMIVVAIIGILAAIAIPQFANYRTKGYNTKAKAE
LKSAYTACQAYFSDNPGATACANATLGGFNNSSDVNIAV
GLSTPTGWTATASHIGGNQTFTVDNGGRITP

Syntrophobacter fumaroxidans

SEQ ID NO: 25   FTLVELMIVVAIIGILAAVAVPYYQKYIQKSRMVSKVFP
GMHAIETNMGTYFSFKNTLLDVGSTATFGQFVQDADTKC
FSPSWAGEYLLITIKDPTLCQELKALTGMTLSATPRMDT
SRTKIRGWALAGPLAVQLGLEGEQ

Syntrophobacter sp. DG_60

SEQ ID NO: 26   FTLIELMIVAAIIAILAAIAIPQYKKFQLKAKTSEAKAN
LGSIRSCEEAYSAETDNYVFCGWTPSNAPTAAGQAWVTT
SGHEGFVSIGFAPAGTSRYCYCVGGSVNTAGTDAATNAF
NEGNVDIYMTAKGDLDGDGSNQWFYATDEDLKVMADYSQ
DDF

Syntrophobacter sp. SbD1

SEQ ID NO: 27   FTLVELMIVVAIIGILAAVAVPYYQKYIQKARLTSKVIP
GIHSIQTDLATYFSFQQMFPGAGATVNAMFTDANTHCFT
PTVTSAAGATSNFKITFAIVGAGCTELSSLYNQTITASP
ILGNNAQVITGWTFGGTLAANMGLAGAQ

Syntrophorhabdus aromaticivorans

SEQ ID NO: 28   FTLIELLIVIAIIGVLAAIAIPAYTGYTKKAKVGEIIHA
LGAIKSAVSVYYSEAGATTDATTADLIRTTYGVDVPTGR
ASFQYTATSREIQATSKITGVTGTMTLTGSTDFKTWTWD
GTMDKAYIPKN

Desulfatibacillum alkenivorans PilA

SEQ ID NO: 29   FTLIELMIVIAIIGILAAIAIPNFVSYRKKAYNRTAQAD
LSSAYSTVMAYYADEKHKEIDNFTLDNLKDAGFKQTVGV
AVTVTSVNFQDFELTARHSQGDIVYTIDAAGARSHN

TABLE 2-continued

Non-limiting Examples of Type IV Pilin Monomer Sequences

*Syntrophomonas zehnderi* PilA

SEQ ID NO: 30  FTLIEILVALFLAILVASSLVTVFQMSHHIFYRDFSRSE
LQYMARKAMEDIIDYVVQAQPDSLAVNGAEGSQLEFILS
SGAKIQYSQGANYWLYRKGPDSGPPQPIVEQIAKVKFCL
SGPHILTVDVVAGNEKNSFTLTQMIVPRAEIDENDWLNS
L

*Syntrophaceticus schinkii* PilA

SEQ ID NO: 31  FTLVELMVVLLIIGILVAIAIPIYNKTQENAQKRACQSN
LRTLDSAAAQYGAATGNYPTDPLNNANFVGENGYVKTKP
TCPAGGVYNYDATNGKFSCNVPDHVYP

*Tepidanaerobacter acetatoxydans* PilA

SEQ ID NO: 32  FTLIELILALGLLSLIMTTSFTIYSAGQKTYEYENSKIF
VQQNARQAFLWLSTSIKQARSVEVMSENSIKTVAGDGET
IIYYFKNGVLYREKNNGINPIAELSQLKFKQPKDKQYIE
IFLAAQGKEGDDIIIKTKATPFGLWVN

*Thermacetogenium phaeum* PilA

SEQ ID NO: 33  FTMIEMMVVLIIIAVLIAGGIRFYLGYVERAKVTKAKSE
ITTMQAALDSYYAEKGEYPDDENDRELVKAGLATDRISI
STEGNDSIQYIYEGGGNSYKIITTATFRAGKLVGEGQDG
KSTEPDFGSGE

TABLE 3

Non-limiting Examples of Tags and their Corresponding Targets

| Target/Analyte | Peptide | SEQ ID NO: |
|---|---|---|
| Table 1 in Karimzadeh et al. (2018) | | |
| MMP-2 | Biotin-Gly-Pro-Leu-Gly-Val-Arg-Gly-Lys-Gly-Gly-Cys | 34 |
| PSA | CEHSSKLQLAK-NH2 | 35 |
| HPV | Ac-(Glu)3-CATACACCTCCAGC-Lys(AQ)NH2 | 36 |
| PSA | Diphenylalanine | |
| MMP-7 | Fc-Lys-Thr-Phe-Lys-Gly-Gly-Gly-Gly-Gly-Gly-Cys | 37 |
| MMP-7 | NH2-KKKRPLALWRSCCC-SH | 38 |
| Caspase-3 | Asp-Glu-Val-Asp | 39 |
| ATP | EKEKEKE-PPPPC | 40 |
| hCG | PPLRINRHILTR | 41 |
| HA | YPYDVPDYA | 42 |
| Caspase-3 | Phe-Arg-Arg | |
| $H_2O_2$ | Diphenylalanine | |
| PSA | CHSSLKQK | 44 |
| K562 cells | Diphenylalanine | |
| MMP-7 | biotin-RPLALWRSCCC-SH | 46 |
| $Hg^{2+}$ | peptide nucleic acid | |
| Substance P | Phe-Phe | |
| TNF-α | Phe-Phe | |
| IgY | H2N-QSPSYPDREYSDEDRQIKQMLHQECPRL-CONH2 | 47 |
| $Pb^{2+}$ | Cys-Thr-Asn-Thr-Leu-Ser-Asn-Asn-Cys (-S-S-) | 48 |
| Prolactin | peptide hormone prolactin | |
| BRCA1 | EKEKEKE | 49 |
| MMP-2 | biotin-GPLGVRGKGGC | 50 |
| MDB | peptide nucleic acid | |
| CEA | peptide-conjugated hemin/G-quadruplex | |

TABLE 3-continued

Non-limiting Examples of Tags and their Corresponding Targets

| Target/Analyte | Peptide | SEQ ID NO: |
|---|---|---|
| DA | Phe-Phe | |
| MMP-7 | NH2-KKKRPLALWRSCCC-SH | 51 |
| Table 1 in Pavan & Berti (2012) | | |
| $Cu^{2+}$ | 3-mer GGH | |
| $Cu^{2+}$ | 3-mer GGH | |
| $Cu^{2+}$ | 3-mer GGH | |
| $Cu^{2+}$ | 8-mer NCGAITIG | 52 |
| $Zn^{2+}$ | Zinc-finger peptide | |
| $Ni^{2+}$ | Tetanus toxin (P12) | |
| $Ni^{2+}$ | HCV sequence (NS4/7) | |
| $Ni^{2+}$ | poly-H sequence | |
| VOCs | Short-chain polypeptide: PAC1 | |
| VOCs | Short-chain polypeptide: PAC2 | |
| VOCs | Short-chain polypeptide: PAM1 | |
| VOCs | Short-chain polypeptide: PAM2 | |
| Dioxins and PCBs | [N]NFQG-aa-[C] | 53 |
| Dioxins | FLDQPhenylglycine (and other designed pentamers) | 54 |
| Atrazine, diuron | EYYY (and other 4-mers from combinatorial libraries) | 55 |
| Carbonic anhydrase | 42-mer helix-loop-helix peptide | |
| Table 2 in Pavan & Berti (2012) | | |
| Murine myofibers | 7-mer ASSLNIA | 56 |
| *Ps. Aeruginosa* whole cells | 9-mer QRKLAAKLT resembling the sequence of natural CPP | 57 |
| SW620 metastatic cells | 12-mer | |
| *Anthrax* protective antigen | 16-mer HKHAHNYRLPASGGGKK | 58 |
| Enterotoxin B | 12-mer | |
| Cardiac troponin I | 12-mer FYSHSFHENWPS | 59 |
| Streptavidin | 12-mer from filamentous R5C2 phages | |
| Methotrexate | 11-mer SIFPLCNSGAL selected directly on a QCM device | 60 |
| TNT | 12-mers sharing a HR consensus dyad | |
| Porphyrin | 5-mer HASYS peptide immobilized on Latex beads to allow 2:1 peptide-to-target complex formation | 61 |
| EDCs | Peptide α/β I | |

TABLE 3-continued

| Non-limiting Examples of Tags and their Corresponding Targets | | |
|---|---|---|
| Target/ Analyte | Peptide | SEQ ID NO: |
| | Table 3 in Pavan & Berti (2012) | |
| Taq DNA polymerase and IgA | 58-mer affibodies from phage display | |
| IgA | $(58\text{-mer})_n$ multimeric affibodies from phage display, by oligomerization of the peptides over the microarray slides | |
| IgE | $(58\text{-mer})_n$ multimeric affibodies from phage display, by oligomerization of the peptides over the microarray slides | |
| IgG | $(58\text{-mer})_n$ multimeric affibodies from phage display, by oligomerization of the peptides over the microarray slides | |
| TNF-α | $(58\text{-mer})_n$ multimeric affibodies from phage display, by oligomerization of the peptides over the microarray slides | |
| insulin | $(58\text{-mer})_n$ multimeric affibodies from phage display, by oligomerization of the peptides over the microarray slides | |
| Taq DNA polymerase | $(58\text{-mer})_n$ multimeric affibodies from phage display, by oligomerization of the peptides over the microarray slides | |
| HER-2 expressing tumor cells | 58-mer affibodies from phage display | |
| HIV-1 pseudopeptide adhesion inhibitors | 25-mer coiled coil from gp41 HIV protein. The peptide acts as an ion channel | |
| Antibodies | 15-mer gramicidin A. 6.3 helical ion channel displaying an antigen | |
| C-reactive protein | 35-mer helix-loop-helix chemically modified coiled coils | |
| Caffeine | 35-mer K coiled-coil randomized peptide from phage display | |
| *Botulinum* neurotoxin | 22-mer synaptotagmin-derived peptide | |
| Phosphoryl peptides | 33-mer WW phosphoprotein binding domain | |
| Nitric oxide released by captured cells | 12-mers derived from the integin-binding fibronectin domain and laminins | |
| Alcohols associated with *Salmonella typhimurium* in beef | LUSH protein sequence (81-93) | |
| VOCs xylene | Human olfactory receptor protein (P30953) fragment: horp61(61-72) | |
| ammonia | Human olfactory receptor protein (P30953) fragment: horp103(103-8) | |
| trimethylamine | Human olfactory receptor protein (P30953) fragment: horp109(109-14) | |
| acetic acid | Human olfactory receptor protein (P30953) fragment: horp193(193-99) | |
| VOCs 1-hexanol | Mouse olfactory receptor (OR744) sequence 210-216 | |
| 1-pentanol | Mouse olfactory receptor (OR744) sequence 210-216 | |

| Table 4 in Pavan & Berti (2012) | | |
|---|---|---|
| mAb against the FLAG peptide | CDYKDDDDK (FLAG) peptide | 62 |
| mAb (12 F10) against HCV protein ARFP (A97) | Polypeptide from HCVARFP | 63 |
| HIV-1 PR | Protease substrate DABCYL-SQNYPIVQ-EDANS | 64 |
| Trypsin | Trypsin substrate DABCYL-GPAXAALAIG-EDANS | 65 |
| Botulinum neurotoxins A | SNAP-25 (187-203 and derivates) | |
| Botulinum neurotoxins B | VAMP-2 (35-70 and derivates) | |
| Botulinum neurotoxins F | VAMP (60-94 and derivates) | |
| Caspase 3 | Peptide substrate SGDEVDSG | 66 |
| Botulinum neurotoxin LcA | SNAP-25 (187-202) modified | |
| Subtilisin | Decapeptide substrate | |
| MMP-7 | Helix peptide with sequence RPLALWRSC | 67 |
| Proteases | Fc-peptide monolayers | |
| Plasmin | Fc-peptide conjugate (KTFK) | 68 |
| Papain | Fc-peptide conjugates | |
| Caspase 3 (detection of apoptotic cells) | Fc-peptide conjugate (GDGDEVDGC) | 69 |
| HIV-1 PR | Fc-pepstatin | |
| HIV-1 PR | Fc-pepstatin conjugates | |
| Protein kinases | Peptide substrates for tyrosine kinases Abl and Src | |
| Protein kinases | ARCs. ARCs are potent inhibitors of protein kinases | |
| MMP-1 | Peptide substrate of catalytic domain (AMFLEA) | 70 |
| β-galactosidase | 20-mer YHNN and QYHH selected from a microarray based on β-galactosidase binding | 71, 72 |
| Table 1 in Puiu & Bala (2018) | | |
| Matrix metalloproteinase-9 (MMP-9) | GPLGMWSRC | 73 |
| Trypsin | GRPS-PEG disulfide | 74 |
| α-thrombin | RFSRPQL-PEG disulfide | 75 |
| Plasmin | KTKTC | 76 |
| Epidermal growth factor receptor | YHWYGYTPQNVI | 77 |
| Prostate specific antigen | HSSKLQL | 78 |
| Amyloid 1-42 | RGTWEGKWK | 79 |
| HIV anti-p24 antibody | EAAEWDRVHP | 80 |

| | | |
|---|---|---|
| Legumain | H2N-(CH2)4-CO-AAAN-NH-CH2- | 81 |
| Cathepsin B | H2N-(CH2)4-CO-LRFG-NH-CH2- | 82 |
| SW620 colorectal carcinoma cells | DDAGNRQP | 83 |//
| Table 1 in Seker & Demir (2011) | | |
| Gold | #VSGSSPDS | 84 |
| Gold | #LKAHLPPSRLPS | 85 |
| Gold | *TGTSVLIATPYV | 86 |
| Silver | *AYSSGAPPMPPF | 87 |
| Silver | *IRPAIHIIPISH | 88 |
| Silver | *WSWRSPTPHVVT | 89 |
| Silica | #MSPHPHPRHHHT | 90 |
| Silica | #RGRRRRLSCRLL | 91 |
| Silica | RLNPPSQMDPPF | 92 |
| Silica | QTWPPPLWFSTS | 93 |
| Silica | HPPMNASHPHMH | 94 |
| Silica | HTKHSHTSPPPL | 95 |
| Silica | CHKKPSKSC | 96 |
| Titania/Titanium | *RKLPDAPGMHTW | 97 |
| Titania/Titanium | *YPSAPPQWLTNT | 98 |
| Titania/Titanium | *STPLVTGTNNLM | 99 |
| Titania/Titanium | *QSGSHVTGDLRL | 100 |
| Titania/Titanium | *ATTLHPPRTSLP | 101 |
| Titania/Titanium | #SCSDCLKSVDFIPSSLASS | 102 |
| Titania/Titanium | #LNAAVPFTMAGS | 103 |
| Titania/Titanium | #ATWVSPY | 104 |
| Titania/Titanium | *RKKRTKNPTHKLGGGW | 105 |
| Titania/Titanium | *KSLSRHDHIHHHGGGW | 106 |
| Titania/Titanium | *TQHLSHPRYATKGGGW | 107 |
| Zinc Oxide | *EAHVMHKVAPRP | 108 |
| Zinc Oxide | *GLHVMHLVAPPR | 109 |
| Zinc Oxide | *VRTRDDARTHRK | 110 |
| Iridium Oxide | #AGETQQAM | 111 |
| Iron Oxide | #LSTVQTISPSNH | 112 |
| Germania | *TGHQSPGAYAAH | 113 |
| Germania | *SLKMPHWPHLLP | 114 |
| Platinum | *CPTSTGQAC | 115 |
| Platinum | *CTLHVSSYC | 116 |
| Palladium | *QQSWPIS | 117 |
| Palladium | *NFMSLPRLGHMH | 118 |

-continued

| | | |
|---|---|---|
| Palladium | #SVTQNKY | 119 |
| Palladium | #SPHPGPY | 120 |
| Palladium | #HAPTPML | 121 |
| Aluminium | #VPSSGPQDTRTT | 122 |
| Aluminium | #YSPDPRPWSSRY | 123 |
| Stainless Steel | *MTWDPSLASPRS | 124 |
| Stainless Steel | *ATIHDAFYSAPE | 125 |
| Stainless Steel | *NLNPNTASAMHV | 126 |
| Fe-Pt Alloy | #HNKHLPSTQPLA | 127 |
| Fe-Pt Alloy | SVSVGMKPSPRP | 128 |
| Fe-Pt Alloy | VISNHRESSRPL | 129 |
| Cobalt | #HSVRWLLPGAHP | 130 |
| Cobalt | KLHSSPHTLPVQ, | 131 |
| Hydroxyapatite | #SVSVGMKPSPRP | 132 |
| Hydroxyapatite | *CMLPHHGAC | 133 |

REFERENCES

1. Lovley, D. R. (2017) Electrically conductive pili: biological function and potential applications in electronics. Curr. Opin. Electrochem. 4, 190-198.
2. Lovley, D. R. (2017) e-Biologics: Fabrication of sustainable electronics with 'green' biological materials. mBio 8, e00695.
3. Guterman, T., and Gazit, E. (2018) Toward peptide-based bioelectronics: reductionist design of conductive pili mimetics. Bioelectron. Med. 1, 131-137.
4. Creasey, R. C. G., Mostert, A. B., Nguyen, T. A. H., Virdis, B., Freguia, S., and Laycock, B. (2018) Microbial nanowires—electron transport and the role of synthetic analogues. Acta Biomater. 69, 1-30.
5. Ing, N. L., El-Naggar, M. Y., and Hochbaum, A. I. (2018) Going the distance: long-range conductivity in protein and peptide bioelectronic materials. J. Phys. Chem. B 122, 10403-10423.
6. Zhou, W., Dai, X., Fu, T.-M., Xie, C., Liu, J., and Lieber, C. M. (2014) Long term stability of nanowire nanoelectronics in physiological environments. Nano Lett. 14, 1614-1619.
7. Malvankar, N. S., Vargas, M., Nevin, K. P., Franks, A. E., Leang, C., Kim, B.-C., Inoue, K., Mester, T., Covalla, S. F., Johnson, J. P., Rotello, V. M., Tuominen, M. T., and Lovley, D. R. (2011) Tunable metallic-like conductivity in nanostructured biofilms comprised of microbial nanowires. Nat. Nanotechnol. 6, 573-579.
8. Adhikari, R. Y., Malvankar, N. S., Tuominen, M. T., and Lovley, D. R. (2016) Conductivity of individual Geobacter pili. RSC Adv. 6, 8354-8357.
9. Lovley, D. R. (2017) Syntrophy goes electric: direct interspecies electron transfer. Annu. Rev. Microbiol. 71, 643-664.
10. Reguera, G., McCarthy, K. D., Mehta, T., Nicoll, J. S., Tuominen, M. T., and Lovley, D. R. (2005) Extracellular electron transfer via microbial nanowires. Nature 435, 1098-1101.
11. Tan, Y., Adhikari, R. Y., Malvankar, N. S., Ward, J. E., Woodard, T. L., Nevin, K. P., and Lovley, D. R. (2017) Expressing the Geobacter metallireducens PilA in Geobacter sulfurreducens yields pili with exceptional conductivity. mBio 8, e02203.
12. Holmes, D. E., Dang, Y., Walker, D. J. F., and Lovley, D. R. The electrically conductive pili of Geobacter species are a recently evolved feature for extracellular electron transfer. Microb. Genomics 2016, 2.
13. Sure, S., Ackland, M. L., Torriero, A. J., Adholeya, A., and Kochar, M. (2016) Microbial nanowires: an electrifying tale. Microbiology 162, 2017-2028.
14. Walker, D. J. F., Adhikari, R. Y., Holmes, D. E., Ward, J. E., Woodard, T. L., Nevin, K. P., and Lovley, D. R. (2018) Electrically conductive pili from genes of phylogenetically diverse microorganisms. ISME J. 12, 48-58.
15. Walker, D. J. F., Martz, E., Holmes, D. E., Zhou, Z., Nonnenmann, S. S., and Lovley, D. R. (2019) The archaellum of Methanospirillum hungatei is electrically conductive. mBio 10, e00579.
16. Cologgi, D. L., Lampa-Pastirk, S., Speers, A. M., Kelly, S. D., and Reguera, G. (2011) Extracellular reduction of uranium via Geobacter conductive pili as a protective cellular mechanism. Proc. Natl. Acad. Sci. U.S.A 108, 15248-15252.
17. Veazey, J. P., Reguera, G., and Tessmer, S. H. (2011) Electronic properties of conductive pili of the metal-reducing bacterium Geobacter sulfurreducens probed by scanning tunneling microscopy. Phys. Rev. 84, 060901.
18. Vargas, M., Malvankar, N. S., Tremblay, P.-L., Leang, C., Smith, J. A., Patel, P., Snoeyenbos-West, O., Nevin, K. P., and Lovley, D. R. (2013) Aromatic amino acids required for pili conductivity and longrange extracellular electron transport in Geobacter sulfurreducens. mBio 4, e00105.
19. Lampa-Pastirk, S., Veazey, J. P., Walsh, K. A., Feliciano, G. T., Steidl, R. J., Tessmer, S., and Reguera, G. (2016) Thermally activated charge transport in microbial protein nanowires. Sci. Rep. 6, 23517.

20. Malvankar, N. S., Yalcin, S. E., Tuominen, M. T., and Lovley, D. R. (2014) Visualization of charge propagation along individual pili proteins using ambient electrostatic force microscopy. Nat. Nanotechnol. 9, 1012-1017.
21. Malvankar, N. S., Vargas, M., Nevin, K. P., Tremblay, P.-L., Evans-Lutterodt, K., Nykypanchuk, D., Martz, E., Tuominen, M. T., and Lovley, D. R. (2015) Structural basis for metallic-like conductivity in microbial nanowires. mBio 6, e00084.
22. Tan, Y., Adhikari, R. Y., Malvankar, N. S., Pi, S., Ward, J. E., Woodard, T. L., Nevin, K. P., Xia, Q., Tuominen, M. T., and Lovley, D. R. (2016) Synthetic biological protein nanowires with high conductivity. Small 12, 4481-4485.
23. Ing, N. L., Nusca, T. D., and Hochbaum, A. I. (2017) Geobacter sulfurreducens pili support ohmic electronic conduction in aqueous solution. Phys. Chem. Chem. Phys. 19, 21791-21799.
24. Wang, F., Gu, Y., O'Brien, J. P., Yi, S. M., Yalcin, S. E., Srikanth, V., Shen, C., Vu, D., Ing, N. L., Hochbaum, A. I., Egelman, E. H., and Malvankar, N. S. (2019) Structure of microbial nanowires reveals stacked hemes that transport electrons over micrometers. Cell 177, 361-369.
25. Filman, D. J., Marino, S. F., Ward, J. E., Yang, L., Mester, Z., Bullitt, E., Lovley, D. R., and Strauss, M. (2019) Cryo-EM reveals the structural basis of long-range electron transport in a cytochrome based bacterial nanowire. Commun. Biol. 2, 219.
26. Lovley, D. R., and Walker, D. J. F. (2019) Geobacter protein nanowires. Peer J. Prepr. 7, e27773v1.
27. Yi, H., Nevin, K. P., Kim, B.-C., Franks, A. E., Klimes, A., Tender, L. M., and Lovley, D. R. (2009) Selection of a variant of Geobacter sulfurreducens with enhanced capacity for current production in microbial fuel cells. Biosens. Bioelectron. 24, 3498-3503.
28. Malvankar, N. S., Tuominen, M. T., and Lovley, D. R. (2012) Lack of involvement of c-type cytochromes in long-range electron transport in microbial biofilms and nanowires. Energy Environ. Sci. 5, 8651-8659.
29. Tan, Y., Adhikari, R. Y., Malvankar, N. S., Ward, J. E., Nevin, K. P., Woodard, T. L., Smith, J. A., Snoeyenbos-West, O. L., Franks, A. E., Tuominen, M. T., and Lovley, D. R. (2016) The low conductivity of Geobacter uraniireducens pili suggests a diversity of extracellular electron transfer mechanisms in the genus Geobacter. Front. Microbiol. 7, 980.
30. Nguyen, P. Q., Botyanszki, Z., Tay, P. K. R., and Joshi, N. S. (2014) Programmable biofilm-based materials from engineered curli nanofibres. Nat. Commun. 5, 4945.
31. Chen, A. Y., Deng, Z., Billings, A. N., Seker, U. O. S., Lu, M. Y., Citorik, R. J., Zakeri, B., and Lu, T. K. (2014) Synthesis and patterning of tunable multiscale materials with engineered cells. Nat. Mater. 13, 515-523.
32. Wang, Y., Pu, J., An, B., Lu, T. K., and Zhong, C. (2018) Emerging paradigms for synthetic design of functional amyloids. J. Mol. Biol. 430, 3720-3734.
33. Nguyen, P. Q., Dorval Courchesne, N.-M., Duraj-Thatte, A., Praveschotinunt, P., and Joshi, N. S. (2018) Engineered living materials: prospects and challenges for using biological systems to direct the assembly of smart Materials. Adv. Mater. 30, 1704847.
34. Hospenthal, M. K., Costa, T. R. D., and Waksman, G. (2017) A comprehensive guide to pilus biogenesis in Gram-negative bacteria. Nat. Rev. Microbiol. 15, 365-379.
35. Liu, X., Zhou, S., and Lovley, D. R. (2019) A pilin chaperone required for the expression of electrically conductive Geobacter sulfurreducens pili. Environ. Microbiol. 21, 2511-2522.
36. Malvankar, N. S., Mester, T., Tuominen, M. T., and Lovley, D. R. (2012) Supercapacitors based on c-type cytochromes using conductive nanostructured networks of living bacteria. ChemPhysChem 13, 463-468.
37. Liu, X., Tremblay, P.-L., Malvankar, N. S., Nevin, K. P., Lovley, D. R., and Vargas, M. (2014) A Geobacter sulfurreducens strain expressing Pseudomonas aeruginosa type IV pili localizes OmcS on pili but is deficient in Fe(III) oxide reduction and current production. Appl. Environ. Microbiol. 80, 1219-1224.
38. Smith, J. A., Tremblay, P.-L., Shrestha, P. M., Snoeyenbos-West, O. L., Franks, A. E., Nevin, K. P., and Lovley, D. R. (2014) Going wireless: Fe(III) oxide reduction without pili by Geobacter sulfurreducens strain JS-1. Appl. Environ. Microbiol. 80, 4331-4340.
39. Liu, X., Wang, S., Xu, A., Zhang, L., Liu, H., and Ma, L. Z. (2019) Biological synthesis of high-conductive pili in aerobic bacterium Pseudomonas aeruginosa. Appl. Microbiol. Biotechnol. 103, 1535-1544.
40. Field, J., Nikawa, J., Broek, D., MacDonald, B., Rodgers, L., Wilson, I. A., Lerner, R. A., and Wigler, M. (1988) Purification of a RAS-responsive adenylyl cyclase complex from Saccharomyces cerevisiae by use of an epitope addition method. Mol. Cell. Biol. 8, 2159-65.
41. Ueki, T., Nevin, K. P., Woodard, T. L., and Lovley, D. R. (2016) Genetic switches and related tools for controlling gene expression and electrical outputs of Geobacter sulfurreducens. J. Ind. Microbiol. Biotechnol. 43, 1561-1575.
42. Ahmad, R., Mahmoudi, T., Ahn, M. S., and Hahn, Y. B. (2018) Recent advances in nanowires-based field-effect transistors for biological sensor applications. Biosens. Bioelectron. 100, 312-325.
43. Zhang, A., and Lieber, C. M. (2016) Nano-Bioelectronics. Chem. Rev. 116, 215-57.
44. Zhu, C., Yang, G., Li, H., Du, D., and Lin, Y. (2015) Electrochemical sensors and biosensors based on nanomaterials and nanostructures. Anal. Chem. 87, 230-49.
45. Lu, Y., Huang, F., Wang, J., and Xia, J. (2014) Affinity-guided covalent conjugation reactions based on PDZ-peptide and SH3-peptide interactions. Bioconjugate Chem. 25, 989-99.
46. Yan, X., Zhou, H., Zhang, J., Shi, C., Xie, X., Wu, Y., Tian, C., Shen, Y., and Long, J. (2009) Molecular mechanism of inward rectifier potassium channel 2.3 regulation by tax-interacting protein-1. J. Mol. Biol. 392, 967-76.
47. Huang, J., Nagy, S. S., Koide, A., Rock, R. S., and Koide, S. (2009) A peptide tag system for facile purification and single molecule immobilization. Biochemistry 48, 11834-6.
48. Gaidamakova, E. K., Backer, M. V., and Backer, J. M. (2001) Molecular vehicle for target-mediated delivery of therapeutics and diagnostics. J. Controlled Release 74, 341-7.
49. Zakeri, B., Fierer, J. O., Celik, E., Chittock, E. C., Schwarz-Linek, U., Moy, V. T., and Howarth, M. (2012) Peptide tag forming a rapid covalent bond to a protein, through engineering a bacterial adhesin. Proc. Natl. Acad. Sci. U.S.A 109 (12), E690-7.
50. Skerra, A., and Schmidt, T. G. (2000) Use of the Strep-Tag and streptavidin for detection and purification of recombinant proteins. Methods Enzymol. 326, 271-304.

51. Pavan, S., and Berti, F. (2012) Short peptides as biosensor transducers. Anal. Bioanal. Chem. 402, 3055.
52. Liu, Q., Wang, J., and Boyd, B. J. (2015) Peptide-based biosensors. Talanta 136, 114-127.
53. Chen, H., Huang, J., Palaniappan, A., Wang, Y., Liedberg, B., Platt, M., and Tok, A. L. Y. (2016) A review on electronic bio-sensing approaches based on non-antibody recognition elements. Analyst 141, 2335.
54. Walker, D. J. F., Nevin, K. P., Nonnenmann, S. S., Holmes, D. E., Woodard, T. L., Ward, J. E., Rotaru, A.-E., McInerney, M. J., and Lovley, D. R. Syntrophus conductive pili demonstrate that common hydrogen-donating syntrophs can have a direct electron transfer option. bioRxiv 2018.
55. Coppi, M. V., Leang, C., Sandler, S. J., and Lovley, D. R. (2001) Development of a genetic system for *Geobacter sulfurreducens*. Appl. Environ. Microbiol. 67, 3180-3187.
56. Sambrook, J., and Russell, D. W. Molecular Cloning: A Laboratory Manual, 3rd ed.; Cold Spring Harbor: Cold Spring Harbor, NY, 2001.
57. Aklujkar, M., and Lovley, D. R. (2010) Interference with histidyl-tRNA synthetase by a CRISPR spacer sequence as a factor in the evolution of *Pelobacter carbinolicus*. BMC Evol. Biol. 10, 230.
58. Ueki, T., DiDonato, L. N., and Lovley, D. R. (2017) Toward establishing minimum requirements for extracellular electron transfer in *Geobacter sulfurreducens*. FEMS Microbiol. Lett. 364, fnx093.
59. Leang, C., Qian, X., Mester, T., and Lovley, D. R. (2010) Alignment of the c-type cytochrome OmcS along pili of *Geobacter sulfurreducens*. Appl. Environ. Microbiol. 76, 4080-4084.
60. Nevin, K. P., Kim, B.-C., Glaven, R. H., Johnson, J. P., Woodard, T. L., Methé, B. A., DiDonato, R. J., Jr, Covalla, S. F., Franks, A. E., Liu, A., and Lovley, D. R. (2009) Anode biofilm transcriptomics reveals outer surface components essential for high current power production in *Geobacter sulfurreducens* fuel cells. PLoS One 4, e5628.
61. Chen H, Huang J, Palaniappan A, Wang Y, Liedberg B, Platt M et al (2016). A review on electronic bio-sensing approaches based on non-antibody recognition elements. Analyst 141: 2335.
62. Gaidamakova E K, Backer M V, Backer J M (2001). Molecular vehicle for target-mediated delivery of therapeutics and diagnostics. J Control Release 74: 341-347.
63. Huang J, Nagy S S, Koide A, Rock R S, Koide S (2009). A peptide tag system for facile purification and single-molecule immobilization. Biochemistry 48: 11834-11836.
64. Karimzadeh A, Hasanzadeh M, Shadjou N, de la Guardia M (2018). Peptide based biosensors. Trends Anal Chem 107: 1-20.
65. Lee S H, Song K B (2009). Isolation of a Calcium-binding Peptide from Enzymatic Hydrolysates of Porcine Blood Plasma Protein. J Korean Soc Appl Biol Chem 52: 290-294.
66. Liu Q, Wang J, Boyd BJ (2015). Peptide-based biosensors. Talanta 136: 114-127.
67. Lu Y, Huang F, Wang J, Xia J (2014). Affinity-guided covalent conjugation reactions based on PDZ-peptide and SH3-peptide interactions. Bioconjug Chem 25: 989-999.
68. Mascini M, Pizzoni D, Perez G, Chiarappa E, Di Natale C, Pittia P et al (2017). Tailoring gas sensor arrays via the design of short peptides sequences as binding elements. Biosens Bioelectron 93: 161-169.
69. Pavan S, Berti F (2012). Short peptides as biosensor transducers. Anal Bioanal Chem 402.
70. Pizzoni D, Mascini M, Lanzone V, Del Carlo M, Di Natale C, Compagnone D (2014). Selection of peptide ligands for piezoelectric peptide based gas sensors arrays using a virtual screening approach. Biosens Bioelectron 52: 247-254.
71. Puiu M, Bala C (2018). Peptide-based biosensors: From self-assembled interfaces to molecular probes in electrochemical assays. Bioelectrochemistry 120: 66-75.
72. Seker U O S, Demir H V (2011). Material Binding Peptides for Nanotechnology. Molecules 16: 1426-1451.
73. Skerra A, Schmidt T G (2000). Use of the Strep-Tag and streptavidin for detection and purification of recombinant proteins. Methods in enzymology 326: 271-304.
74. Tang N, Skibsted L H (2016). Calcium Binding to Amino Acids and Small Glycine Peptides in Aqueous Solution: Toward Peptide Design for Better Calcium Bioavailability. J Agric Food Chem 64: 4376-4389.
75. Yan X, Zhou H, Zhang J, Shi C, Xie X, Wu Y et al (2009). Molecular mechanism of inward rectifier potassium channel 2.3 regulation by tax-interacting protein-1. Journal of molecular biology 392: 967-976.
76. Zakeri B, Fierer J O, Celik E, Chittock E C, Schwarz-Linek U, Moy V T et al (2012). Peptide tag forming a rapid covalent bond to a protein, through engineering a bacterial adhesin. Proc Natl Acad Sci USA 109: E690-697.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. An electrically conductive nanowire comprising a fusion protein comprising a type IV pilin monomer and a tag, wherein the tag is at the C-terminus of the type IV pilin monomer, and wherein the nanowire further comprises an untagged type IV pilin monomer.

2. The electrically conductive nanowire of claim 1, wherein the molar ratio of fusion protein to untagged type IV pilin monomer is in the range of about 10:1 to about 1:10.

3. The electrically conductive nanowire of claim 1, comprising a plurality of surface exposed peptide tags.

4. The electrically conductive nanowire of claim 1, wherein the nanowire has a diameter of from about 3 nm to about 4 nm.

5. The electrically conductive nanowire of claim 1, wherein the nanowire has a length of from about 0.5 µm to about 20 µm.

6. The electrically conductive nanowire of claim 1, wherein the nanowire has a conductivity of from about 40 µS/cm to about 300 S/cm at a temperature of about 25° C. and a pH of about 7.

7. A nanowire sensor device comprising:
the electrically conductive nanowire of claim 1;
a first electrode having a first electrode terminal, wherein the first electrode is configured to support and is in physical contact with the electrically conductive nanowire;
a second electrode having a second electrode terminal, wherein the second electrode is configured to support and is in physical contact with the electrically conductive nanowire;
an electrical resistance connected between the first electrode terminal and the second electrode terminal; and
an electrical current monitor in electrical communication with the electrical resistance, wherein the electrical current monitor is configured to measure an electrical current passing through the electrical resistance.

8. A polynucleotide encoding the electrically conductive nanowire of claim 1.

9. An expression vector comprising the polynucleotide of claim 8.

10. A host cell comprising the polynucleotide of claim 8.

11. A method of producing electrically conductive protein nanowires, comprising the steps of:

a) introducing the polynucleotide of claim 8 into a host cell;
b) placing the host cell in a culture medium conditioned for producing type IV pili;
culturing the host cell for a time sufficient to produce a desired quantity of the c) type IV pili; and
d) isolating the type IV pili from the culture medium,
thereby producing the electrically conductive protein nanowires.

12. The electrically conductive nanowire of claim 1, wherein the type IV pilin monomer in the fusion protein is a PilA monomer or a variant thereof.

13. The electrically conductive nanowire of claim 1, wherein the type IV pilin monomer in the fusion protein comprises an amino acid sequence that has at least 90% sequence identity to the wildtype *Geobacter sulfurreducens* PilA monomer (SEQ ID NO: 2).

14. The electrically conductive nanowire of claim 1, wherein the type IV pilin monomer in the fusion protein is wildtype *Geobacter sulfurreducens* PilA monomer (SEQ ID NO: 2).

15. The electrically conductive nanowire of claim 1, wherein the type IV pilin monomer in the fusion protein is a *Geobacter sulfurreducens* PilA variant comprising a deletion or a substitution of an aromatic amino acid in the wildtype *Geobacter sulfurreducens* PilA (SEQ ID NO: 2).

16. The electrically conductive nanowire of claim 1, wherein the tag comprises a binding motif.

17. The electrically conductive nanowire of claim 1, wherein the tag comprises two to ten consecutive histidine amino acids.

18. The electrically conductive nanowire of claim 1, wherein the tag comprises a human influenza hemagglutinin (HA) sequence (SEQ ID NO: 11).

19. The electrically conductive nanowire of claim 1, wherein the untagged type IV pilin monomer comprises an amino acid sequence that has at least 90% sequence identity to wildtype *Geobacter sulfurreducens* PilA (SEQ ID NO: 2).

20. The electrically conductive nanowire of claim 1, wherein the untagged type IV pilin monomer is a *Geobacter sulfurreducens* PilA variant comprising a deletion or a substitution of an aromatic amino acid in wildtype *Geobacter sulfurreducens* PilA (SEQ ID NO: 2).

* * * * *

UNITED STATES PATENT AND TRADEMARK OFFICE
CERTIFICATE OF CORRECTION

| | | |
|---|---|---|
| PATENT NO. | : 12,320,802 B2 | Page 1 of 1 |
| APPLICATION NO. | : 17/440632 | |
| DATED | : June 3, 2025 | |
| INVENTOR(S) | : Derek R. Lovley and Toshiyuki Ueki | |

It is certified that error appears in the above-identified patent and that said Letters Patent is hereby corrected as shown below:

In the Claims

In Claim 11, Column 98, Line 5, before "culturing" insert --c)--.

In Claim 11, Column 98, Line 6, delete "c)".

Signed and Sealed this
Twenty-third Day of September, 2025

John A. Squires
*Director of the United States Patent and Trademark Office*

SEQUENCE LISTING

<160> NUMBER OF SEQ ID NOS: 149

<210> SEQ ID NO 1
<211> LENGTH: 216
<212> TYPE: DNA
<213> ORGANISM: Geobacter sulfurreducens

<400> SEQUENCE: 1
atgcttcaga aactcagaaa caggaaaggt ttcaccctta tcgagctgct gatcgtcgtt      60
gcgatcatcg gtattctcgc tgcaattgcg attccgcagt tctcggcgta tcgtgtcaag     120

```
gcgtacaaca gcgcggcgtc aagcgacttg agaaacctga agactgctct tgagtccgca    180
tttgctgatg atcaaaccta tccgcccgaa agttaa                              216
```

<210> SEQ ID NO 2
<211> LENGTH: 61
<212> TYPE: PRT
<213> ORGANISM: Geobacter sulfurreducens

<400> SEQUENCE: 2

```
Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60
```

<210> SEQ ID NO 3
<211> LENGTH: 4
<212> TYPE: PRT
<213> ORGANISM: Artificial Sequence
<220> FEATURE:
<223> OTHER INFORMATION: peptide tag

<400> SEQUENCE: 3

```
His His His His
1
```

<210> SEQ ID NO 4
<211> LENGTH: 5
<212> TYPE: PRT
<213> ORGANISM: Artificial Sequence
<220> FEATURE:
<223> OTHER INFORMATION: peptide tag

<400> SEQUENCE: 4

```
His His His His His
1               5
```

<210> SEQ ID NO 5
<211> LENGTH: 6
<212> TYPE: PRT
<213> ORGANISM: Artificial Sequence
<220> FEATURE:
<223> OTHER INFORMATION: peptide tag

<400> SEQUENCE: 5

```
His His His His His His
1               5
```

<210> SEQ ID NO 6
<211> LENGTH: 7
<212> TYPE: PRT
<213> ORGANISM: Artificial Sequence
<220> FEATURE:
<223> OTHER INFORMATION: peptide tag

<400> SEQUENCE: 6

```
His His His His His His His
1               5
```

<210> SEQ ID NO 7
<211> LENGTH: 8

-continued

```
<212> TYPE: PRT
<213> ORGANISM: Artificial sequence
<220> FEATURE:
<223> OTHER INFORMATION: peptide tag

<400> SEQUENCE: 7

His His His His His His His His
1               5

<210> SEQ ID NO 8
<211> LENGTH: 9
<212> TYPE: PRT
<213> ORGANISM: Artificial Sequence
<220> FEATURE:
<223> OTHER INFORMATION: peptide tag

<400> SEQUENCE: 8

His His His His His His His His His
1               5

<210> SEQ ID NO 9
<211> LENGTH: 10
<212> TYPE: PRT
<213> ORGANISM: Artificial Sequence
<220> FEATURE:
<223> OTHER INFORMATION: peptide tag

<400> SEQUENCE: 9

His His His His His His His His His His
1               5                   10

<210> SEQ ID NO 10
<211> LENGTH: 7
<212> TYPE: PRT
<213> ORGANISM: Artificial Sequence
<220> FEATURE:
<223> OTHER INFORMATION: peptide tag

<400> SEQUENCE: 10

His His His His His His Cys
1               5

<210> SEQ ID NO 11
<211> LENGTH: 9
<212> TYPE: PRT
<213> ORGANISM: Artificial sequence
<220> FEATURE:
<223> OTHER INFORMATION: peptide tag

<400> SEQUENCE: 11

Tyr Pro Tyr Asp Val Pro Asp Tyr Ala
1               5

<210> SEQ ID NO 12
<211> LENGTH: 234
<212> TYPE: PRT
<213> ORGANISM: Artificial Sequence
<220> FEATURE:
<223> OTHER INFORMATION: PilA-6His Fusion Protein

<400> SEQUENCE: 12

Ala Thr Gly Cys Thr Thr Cys Ala Gly Ala Ala Ala Cys Thr Cys Ala
1               5                   10                  15

Gly Ala Ala Ala Cys Ala Gly Gly Ala Ala Ala Gly Gly Thr Thr Thr
                20                  25                  30

Cys Ala Cys Cys Cys Thr Thr Ala Thr Cys Gly Ala Gly Cys Thr Gly
```

```
             35                  40                  45
Cys Thr Gly Ala Thr Cys Gly Thr Cys Gly Thr Thr Gly Cys Gly Ala
         50                  55                  60

Thr Cys Ala Thr Cys Gly Gly Thr Ala Thr Thr Cys Thr Cys Gly Cys
65                  70                  75                  80

Thr Gly Cys Ala Ala Thr Thr Gly Cys Gly Ala Thr Thr Cys Cys Gly
                 85                  90                  95

Cys Ala Gly Thr Thr Cys Thr Cys Gly Gly Cys Gly Thr Ala Thr Cys
                100                 105                 110

Gly Thr Gly Thr Cys Ala Ala Gly Gly Cys Gly Thr Ala Cys Ala Ala
            115                 120                 125

Cys Ala Gly Cys Gly Cys Gly Gly Cys Gly Thr Cys Ala Ala Gly Cys
        130                 135                 140

Gly Ala Cys Thr Thr Gly Ala Gly Ala Ala Cys Cys Thr Gly Ala Ala
145                 150                 155                 160

Ala Gly Ala Cys Thr Gly Cys Thr Cys Thr Thr Gly Ala Gly Thr Cys
                165                 170                 175

Cys Gly Cys Ala Thr Thr Thr Gly Cys Thr Gly Ala Thr Gly Ala Thr
                180                 185                 190

Cys Ala Ala Ala Cys Cys Thr Ala Thr Cys Cys Gly Cys Cys Cys Gly
            195                 200                 205

Ala Ala Ala Gly Thr Cys Ala Cys Cys Ala Cys Cys Ala Cys Cys Ala
210                 215                 220

Cys Cys Ala Cys Cys Ala Cys Thr Ala Ala
225                 230
```

```
<210> SEQ ID NO 13
<211> LENGTH: 67
<212> TYPE: PRT
<213> ORGANISM: Artificial Sequence
<220> FEATURE:
<223> OTHER INFORMATION: PilA-6His Fusion Protein

<400> SEQUENCE: 13

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser His His His
    50                  55                  60

His His His
65
```

```
<210> SEQ ID NO 14
<211> LENGTH: 243
<212> TYPE: PRT
<213> ORGANISM: Artificial Sequence
<220> FEATURE:
<223> OTHER INFORMATION: PilA-HA Fusion Protein

<400> SEQUENCE: 14

Ala Thr Gly Cys Thr Thr Cys Ala Gly Ala Ala Cys Thr Cys Ala
1               5                   10                  15

Gly Ala Ala Ala Cys Ala Gly Gly Ala Ala Ala Gly Gly Thr Thr Thr
            20                  25                  30
```

```
Cys Ala Cys Cys Cys Thr Thr Ala Thr Cys Gly Ala Gly Cys Thr Gly
             35                  40                  45

Cys Thr Gly Ala Thr Cys Gly Thr Cys Gly Thr Thr Gly Cys Gly Ala
 50                  55                  60

Thr Cys Ala Thr Cys Gly Gly Thr Ala Thr Cys Thr Cys Gly Cys
 65                  70                  75                  80

Thr Gly Cys Ala Ala Thr Thr Gly Cys Gly Ala Thr Cys Cys Gly
             85                  90                  95

Cys Ala Gly Thr Thr Cys Thr Cys Gly Gly Cys Gly Thr Ala Thr Cys
             100                 105                 110

Gly Thr Gly Thr Cys Ala Ala Gly Gly Cys Gly Thr Ala Cys Ala Ala
             115                 120                 125

Cys Ala Gly Cys Gly Cys Gly Gly Cys Gly Thr Cys Ala Ala Gly Cys
             130                 135                 140

Gly Ala Cys Thr Thr Gly Ala Gly Ala Ala Cys Cys Thr Gly Ala
145                 150                 155                 160

Ala Gly Ala Cys Thr Gly Cys Thr Cys Thr Thr Gly Ala Gly Thr Cys
             165                 170                 175

Cys Gly Cys Ala Thr Thr Thr Gly Cys Thr Gly Ala Thr Gly Ala Thr
             180                 185                 190

Cys Ala Ala Cys Cys Thr Ala Thr Cys Cys Gly Cys Cys Cys Gly
             195                 200                 205

Ala Ala Ala Gly Thr Thr Ala Cys Cys Cys Gly Thr Ala Cys Gly Ala
             210                 215                 220

Cys Gly Thr Gly Cys Cys Gly Gly Ala Cys Thr Ala Cys Gly Cys Gly
225                 230                 235                 240

Thr Ala Ala
```

<210> SEQ ID NO 15
<211> LENGTH: 70
<212> TYPE: PRT
<213> ORGANISM: Artificial Sequence
<220> FEATURE:
<223> OTHER INFORMATION: PilA-HA Fusion Protein

<400> SEQUENCE: 15

```
Phe Thr Leu Ile Glu Leu Leu Ile Val Val Ala Ile Ile Gly Ile Leu
 1               5                  10                  15

Ala Ala Ile Ala Ile Pro Gln Phe Ser Ala Tyr Arg Val Lys Ala Tyr
             20                  25                  30

Asn Ser Ala Ala Ser Ser Asp Leu Arg Asn Leu Lys Thr Ala Leu Glu
         35                  40                  45

Ser Ala Phe Ala Asp Asp Gln Thr Tyr Pro Pro Glu Ser Tyr Pro Tyr
 50                  55                  60

Asp Val Pro Asp Tyr Ala
 65                  70
```

<210> SEQ ID NO 16
<211> LENGTH: 61
<212> TYPE: PRT
<213> ORGANISM: Artificial Sequence
<220> FEATURE:
<223> OTHER INFORMATION: PilA-Cys Fusion Protein

<400> SEQUENCE: 16

```
Phe Thr Leu Ile Glu Leu Leu Ile Val Val Ala Ile Ile Gly Ile Leu
 1               5                  10                  15
```

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
            35                  40                  45

Ser Ala Phe Ala Asp Asp Gln Thr Tyr Pro Pro Glu Cys
    50                  55                  60

<210> SEQ ID NO 17
<211> LENGTH: 68
<212> TYPE: PRT
<213> ORGANISM: Artificial Sequence
<220> FEATURE:
<223> OTHER INFORMATION: PilA-6His-Cys Fusion Protein

<400> SEQUENCE: 17

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
            35                  40                  45

Ser Ala Phe Ala Asp Asp Gln Thr Tyr Pro Pro Glu Ser His His His
    50                  55                  60

His His His Cys
65

<210> SEQ ID NO 18
<211> LENGTH: 59
<212> TYPE: PRT
<213> ORGANISM: Geobacter metallireducens

<400> SEQUENCE: 18

Phe Thr Leu Ile Glu Leu Leu Ile Val Val Ala Ile Ile Gly Ile Leu
1               5                   10                  15

Ala Ala Ile Ala Ile Pro Gln Phe Ala Ala Tyr Arg Gln Lys Ala Phe
            20                  25                  30

Asn Ser Ala Ala Glu Ser Asp Leu Lys Asn Thr Lys Thr Asn Leu Glu
            35                  40                  45

Ser Tyr Tyr Ser Glu His Gln Phe Tyr Pro Asn
    50                  55

<210> SEQ ID NO 19
<211> LENGTH: 119
<212> TYPE: PRT
<213> ORGANISM: Calditerrivibrio nitroreducens

<400> SEQUENCE: 19

Phe Thr Leu Ile Glu Leu Leu Val Val Val Ala Ile Ile Ala Ile Leu
1               5                   10                  15

Ala Ala Ile Ala Ile Pro Gln Phe Ala Lys Tyr Arg Glu Asn Ala Ala
            20                  25                  30

Lys Ala Ser Ala Val Ala Asp Ala Lys Asn Ile Ala Thr Ala Ile Glu
            35                  40                  45

Ser Tyr Tyr Ala Asp Thr Gln Ser Phe Pro Ser Ser Ile Ser Asp Gly
    50                  55                  60

Ser Ile Val Pro Leu Gly Thr Gln Thr Phe Ser Leu Ser Lys Asn Asn
65                  70                  75                  80

Ser Phe Lys Gly Tyr Tyr Tyr Asn Asn Pro Ser Tyr Thr Phe Val Val
                85                  90                  95

```
Ser Asn Thr Ala Phe Asn Arg Ser Val Thr Phe Asn Ser Ala Thr Gly
            100                 105                 110

Gly Val Asp Val Asn Val Trp
        115

<210> SEQ ID NO 20
<211> LENGTH: 182
<212> TYPE: PRT
<213> ORGANISM: Desulfurvibrio alkaliphilus

<400> SEQUENCE: 20

Phe Thr Leu Val Glu Leu Met Ile Val Val Ala Ile Ile Gly Ile Leu
1               5                   10                  15

Ala Ala Val Ala Ile Pro Gln Phe Ala Gln Tyr Arg Ile Arg Gly Phe
            20                  25                  30

Asn Ser Ser Ala Leu Ser Asp Val Arg Asn Leu Thr Thr Ala Gln Glu
        35                  40                  45

Ala Phe Phe Ala Asp Trp Leu Arg Tyr Ala Val Thr His Glu Ala Ala
    50                  55                  60

Asp Val Thr Glu Val Lys Ala Thr Gly Asp Leu Leu Glu Gly Pro Ser
65                  70                  75                  80

Thr Gly Ala Met Val Leu Ala Gln Trp Ala Arg Gln Ala His Gln Gln
                85                  90                  95

Leu Pro Leu Ala Ile Gly Asn Gly Val Val Met Gln Ala Asp Val Ile
            100                 105                 110

Pro Ala Thr Ala Val Ser Tyr Val Ala Ile Ser Lys His Leu Gln Gly
        115                 120                 125

Asn Thr Met Tyr Gly Ala Thr Asn Thr Ser Thr Ala Ile His Arg Asp
    130                 135                 140

Gln Glu Thr Leu Val Pro Gly Gln Gly Gly Asp Val Leu Pro Ile Thr
145                 150                 155                 160

Gly Tyr Met Pro Glu Pro His Gly Thr Asp Asp Pro Phe Ile Asp His
                165                 170                 175

Glu Glu Phe Glu Ala Gln
            180

<210> SEQ ID NO 21
<211> LENGTH: 60
<212> TYPE: PRT
<213> ORGANISM: Felxistipes sinusarabici

<400> SEQUENCE: 21

Phe Thr Leu Ile Glu Leu Leu Val Val Ala Ile Ile Gly Ile Leu
1               5                   10                  15

Ala Ala Ile Ala Ile Pro Gln Phe Ala Lys Tyr Arg Ile Asn Ala Phe
            20                  25                  30

Asn Ser Ala Ala Gln Ser Asp Leu Ala Asn Val Lys Ser Ala Leu Glu
        35                  40                  45

Ser Tyr Tyr Ala Glu Asn Phe Thr Tyr Pro Ser Pro
    50                  55                  60

<210> SEQ ID NO 22
<211> LENGTH: 110
<212> TYPE: PRT
<213> ORGANISM: Synthrophus aciditrophicus

<400> SEQUENCE: 22
```

```
Phe Thr Leu Ile Glu Leu Met Ile Val Ile Ala Ile Gly Ile Leu
1               5                   10                  15

Ala Ala Ile Ala Ile Pro Gln Phe Gln Gln Tyr Arg Thr Arg Gly Tyr
            20                  25                  30

Asn Thr Ala Ala Lys Ala Asp Ala Lys Asn Ala Tyr Thr Ala Ala Gln
        35                  40                  45

Ala Tyr Phe Ser Asp His Pro Ser Val Thr Ile Ser Ser Ile Thr Asp
    50                  55                  60

Leu Ala Asn Tyr Gly Phe Lys Ala Ser Ala Asp Val Thr Thr Thr Ala
65                  70                  75                  80

Ala Gly Asp Met Asp Gly Leu Ala Ile Thr Ala Lys His Ser Ala Ser
                85                  90                  95

Asp Thr Thr Tyr Gln Val Asp Ser Gln Gly Thr Ile Thr Pro
            100                 105                 110
```

<210> SEQ ID NO 23
<211> LENGTH: 120
<212> TYPE: PRT
<213> ORGANISM: Syntrophus gentianae

<400> SEQUENCE: 23

```
Phe Thr Leu Ile Glu Leu Met Ile Val Ile Ala Ile Gly Ile Leu
1               5                   10                  15

Ala Ala Ile Ala Ile Pro Gln Phe Thr Gln Tyr Arg Lys Arg Ala Tyr
            20                  25                  30

Asp Ala Ser Ser Lys Ala Asp Leu Lys Ser Ala Tyr Thr Ala Ala Gln
        35                  40                  45

Ala Trp Phe Asn Asp Asn Pro Ser Gly Thr Leu Pro Ala Ala Thr Ile
    50                  55                  60

Thr Ser Ala Thr Thr Thr Gly Glu Leu Pro Gly Asn Gly Phe Lys Ala
65                  70                  75                  80

Ser Thr Gly Val Thr Ala Thr Val Thr Ser Gly Thr Met Gly Thr Phe
                85                  90                  95

Ser Ile Ala Thr Thr His Ser Gln Gly Thr Lys Thr Tyr Asn Ile Thr
            100                 105                 110

Ala Gly Gly Thr Leu Thr Glu Ser
        115                 120
```

<210> SEQ ID NO 24
<211> LENGTH: 109
<212> TYPE: PRT
<213> ORGANISM: Smithella sp. F21

<400> SEQUENCE: 24

```
Phe Thr Leu Ile Glu Leu Met Ile Val Val Ala Ile Ile Gly Ile Leu
1               5                   10                  15

Ala Ala Ile Ala Ile Pro Gln Phe Ala Asn Tyr Arg Thr Lys Gly Tyr
            20                  25                  30

Asn Thr Lys Ala Lys Ala Glu Leu Lys Ser Ala Tyr Thr Ala Cys Gln
        35                  40                  45

Ala Tyr Phe Ser Asp Asn Pro Gly Ala Thr Ala Cys Ala Asn Ala Thr
    50                  55                  60

Leu Gly Gly Phe Asn Asn Ser Ser Asp Val Asn Ile Ala Val Gly Leu
65                  70                  75                  80

Ser Thr Pro Thr Gly Trp Thr Ala Thr Ala Ser His Ile Gly Gly Asn
                85                  90                  95
```

```
Gln Thr Phe Thr Val Asp Asn Gly Gly Arg Ile Thr Pro
            100                 105
```

<210> SEQ ID NO 25
<211> LENGTH: 141
<212> TYPE: PRT
<213> ORGANISM: Syntrophobacter fumaroxidans

<400> SEQUENCE: 25

```
Phe Thr Leu Val Glu Leu Met Ile Val Ala Ile Ile Gly Ile Leu
1               5                   10                  15

Ala Ala Val Ala Val Pro Tyr Tyr Gln Lys Tyr Ile Gln Lys Ser Arg
                20                  25                  30

Met Val Ser Lys Val Phe Pro Gly Met His Ala Ile Glu Thr Asn Met
            35                  40                  45

Gly Thr Tyr Phe Ser Phe Lys Asn Thr Leu Leu Asp Val Gly Ser Thr
        50                  55                  60

Ala Thr Phe Gly Gln Phe Val Gln Asp Ala Asp Thr Lys Cys Phe Ser
65                  70                  75                  80

Pro Ser Trp Ala Gly Glu Tyr Leu Leu Ile Thr Ile Lys Asp Pro Thr
                85                  90                  95

Leu Cys Gln Glu Leu Lys Ala Leu Thr Gly Met Thr Leu Ser Ala Thr
            100                 105                 110

Pro Arg Met Asp Thr Ser Arg Thr Lys Ile Arg Gly Trp Ala Leu Ala
        115                 120                 125

Gly Pro Leu Ala Val Gln Leu Gly Leu Glu Gly Glu Gln
    130                 135                 140
```

<210> SEQ ID NO 26
<211> LENGTH: 159
<212> TYPE: PRT
<213> ORGANISM: Syntrophobacter sp. DG_60

<400> SEQUENCE: 26

```
Phe Thr Leu Ile Glu Leu Met Ile Val Ala Ile Ala Ile Leu
1               5                   10              15

Ala Ala Ile Ala Ile Pro Gln Tyr Lys Lys Phe Gln Leu Lys Ala Lys
                20                  25                  30

Thr Ser Glu Ala Lys Ala Asn Leu Gly Ser Ile Arg Ser Cys Glu Glu
            35                  40                  45

Ala Tyr Ser Ala Glu Thr Asp Asn Tyr Val Phe Cys Gly Trp Thr Pro
        50                  55                  60

Ser Asn Ala Pro Thr Ala Ala Gly Gln Ala Trp Val Thr Thr Ser Gly
65                  70                  75                  80

His Glu Gly Phe Val Ser Ile Gly Phe Ala Pro Ala Gly Thr Ser Arg
                85                  90                  95

Tyr Cys Tyr Cys Val Gly Gly Ser Val Asn Thr Ala Gly Thr Asp Ala
            100                 105                 110

Ala Thr Asn Ala Phe Asn Glu Gly Asn Val Asp Ile Tyr Met Thr Ala
        115                 120                 125

Lys Gly Asp Leu Asp Gly Asp Gly Ser Asn Gln Trp Phe Tyr Ala Thr
130                 135                 140

Asp Glu Asp Leu Lys Val Met Ala Asp Tyr Ser Gln Asp Asp Phe
145                 150                 155
```

<210> SEQ ID NO 27
<211> LENGTH: 145

<212> TYPE: PRT
<213> ORGANISM: Syntrophobacter sp. SbD1

<400> SEQUENCE: 27

```
Phe Thr Leu Val Glu Leu Met Ile Val Ala Ile Ile Gly Ile Leu
1               5                   10                  15

Ala Ala Val Ala Val Pro Tyr Tyr Gln Lys Tyr Ile Gln Lys Ala Arg
            20                  25                  30

Leu Thr Ser Lys Val Ile Pro Gly Ile His Ser Ile Gln Thr Asp Leu
            35                  40                  45

Ala Thr Tyr Phe Ser Phe Gln Gln Met Phe Pro Gly Ala Gly Ala Thr
        50                  55                  60

Val Asn Ala Met Phe Thr Asp Ala Asn Thr His Cys Phe Thr Pro Thr
65                  70                  75                  80

Val Thr Ser Ala Ala Gly Ala Thr Ser Asn Phe Lys Ile Thr Phe Ala
                85                  90                  95

Ile Val Gly Ala Gly Cys Thr Glu Leu Ser Ser Leu Tyr Asn Gln Thr
            100                 105                 110

Ile Thr Ala Ser Pro Ile Leu Gly Asn Asn Ala Gln Val Ile Thr Gly
        115                 120                 125

Trp Thr Phe Gly Gly Thr Leu Ala Ala Asn Met Gly Leu Ala Gly Ala
130                 135                 140

Gln
145
```

<210> SEQ ID NO 28
<211> LENGTH: 128
<212> TYPE: PRT
<213> ORGANISM: Syntrophorhabdus aromaticivorans

<400> SEQUENCE: 28

```
Phe Thr Leu Ile Glu Leu Leu Ile Val Ile Ala Ile Ile Gly Val Leu
1               5                   10                  15

Ala Ala Ile Ala Ile Pro Ala Tyr Thr Gly Tyr Thr Lys Lys Ala Lys
            20                  25                  30

Val Gly Glu Ile Ile His Ala Leu Gly Ala Ile Lys Ser Ala Val Ser
            35                  40                  45

Val Tyr Tyr Ser Glu Ala Gly Ala Thr Thr Asp Ala Thr Thr Ala Asp
        50                  55                  60

Leu Ile Arg Thr Thr Tyr Gly Val Asp Val Pro Thr Gly Arg Ala Ser
65                  70                  75                  80

Phe Gln Tyr Thr Ala Thr Ser Arg Glu Ile Gln Ala Thr Ser Lys Ile
                85                  90                  95

Thr Gly Val Thr Gly Thr Met Thr Leu Thr Gly Ser Thr Asp Phe Lys
            100                 105                 110

Thr Trp Thr Trp Asp Gly Thr Met Asp Lys Ala Tyr Ile Pro Lys Asn
        115                 120                 125
```

<210> SEQ ID NO 29
<211> LENGTH: 114
<212> TYPE: PRT
<213> ORGANISM: Desulfatibacillum alkenivorans

<400> SEQUENCE: 29

```
Phe Thr Leu Ile Glu Leu Met Ile Val Ile Ala Ile Ile Gly Ile Leu
1               5                   10                  15

Ala Ala Ile Ala Ile Pro Asn Phe Val Ser Tyr Arg Lys Lys Ala Tyr
```

```
            20                  25                  30
Asn Arg Thr Ala Gln Ala Asp Leu Ser Ser Ala Tyr Ser Thr Val Met
            35                  40                  45

Ala Tyr Tyr Ala Asp Glu Lys His Lys Glu Ile Asp Asn Phe Thr Leu
    50                  55                  60

Asp Asn Leu Lys Asp Ala Gly Phe Lys Gln Thr Val Gly Val Ala Val
65                  70                  75                  80

Thr Val Thr Ser Val Asn Phe Gln Asp Phe Glu Leu Thr Ala Arg His
                85                  90                  95

Ser Gln Gly Asp Ile Val Tyr Thr Ile Asp Ala Ala Gly Ala Arg Ser
            100                 105                 110

His Asn

<210> SEQ ID NO 30
<211> LENGTH: 157
<212> TYPE: PRT
<213> ORGANISM: Syntrophomonas zehnderi

<400> SEQUENCE: 30

Phe Thr Leu Ile Glu Ile Leu Val Ala Leu Phe Leu Ala Ile Leu Val
1               5                   10                  15

Ala Ser Ser Leu Val Thr Val Phe Gln Met Ser His His Ile Phe Tyr
            20                  25                  30

Arg Asp Phe Ser Arg Ser Glu Leu Gln Tyr Met Ala Arg Lys Ala Met
        35                  40                  45

Glu Asp Ile Ile Asp Tyr Val Val Gln Ala Gln Pro Asp Ser Leu Ala
    50                  55                  60

Val Asn Gly Ala Glu Gly Ser Gln Leu Glu Phe Ile Leu Ser Ser Gly
65                  70                  75                  80

Ala Lys Ile Gln Tyr Ser Gln Gly Ala Asn Tyr Trp Leu Tyr Arg Lys
                85                  90                  95

Gly Pro Asp Ser Gly Pro Pro Gln Pro Ile Val Glu Gln Ile Ala Lys
            100                 105                 110

Val Lys Phe Cys Leu Ser Gly Pro His Ile Leu Thr Val Asp Val Val
        115                 120                 125

Ala Gly Asn Glu Lys Asn Ser Phe Thr Leu Thr Gln Met Ile Val Pro
    130                 135                 140

Arg Ala Glu Ile Asp Glu Asn Asp Trp Leu Asn Ser Leu
145                 150                 155

<210> SEQ ID NO 31
<211> LENGTH: 105
<212> TYPE: PRT
<213> ORGANISM: Syntrophaceticus schinkii

<400> SEQUENCE: 31

Phe Thr Leu Val Glu Leu Met Val Val Leu Ile Ile Gly Ile Leu
1               5                   10                  15

Val Ala Ile Ala Ile Pro Ile Tyr Asn Lys Thr Gln Glu Asn Ala Gln
            20                  25                  30

Lys Arg Ala Cys Gln Ser Asn Leu Arg Thr Leu Asp Ser Ala Ala Ala
        35                  40                  45

Gln Tyr Gly Ala Ala Thr Gly Asn Tyr Pro Asp Pro Leu Asn Asn
    50                  55                  60

Ala Asn Phe Val Gly Glu Asn Gly Tyr Val Lys Thr Lys Pro Thr Cys
65                  70                  75                  80
```

```
Pro Ala Gly Gly Val Tyr Asn Tyr Asp Ala Thr Asn Gly Lys Phe Ser
                85                  90                  95

Cys Asn Val Pro Asp His Val Tyr Pro
            100                 105

<210> SEQ ID NO 32
<211> LENGTH: 144
<212> TYPE: PRT
<213> ORGANISM: Tepidanaerobacter acetatoxydans

<400> SEQUENCE: 32

Phe Thr Leu Ile Glu Leu Ile Leu Ala Leu Gly Leu Leu Ser Leu Ile
1               5                   10                  15

Met Thr Thr Ser Phe Thr Ile Tyr Ser Ala Gly Gln Lys Thr Tyr Glu
            20                  25                  30

Tyr Glu Asn Ser Lys Ile Phe Val Gln Gln Asn Ala Arg Gln Ala Phe
        35                  40                  45

Leu Trp Leu Ser Thr Ser Ile Lys Gln Ala Arg Ser Val Glu Val Met
    50                  55                  60

Ser Glu Asn Ser Ile Lys Thr Val Ala Gly Asp Gly Glu Thr Ile Ile
65                  70                  75                  80

Tyr Tyr Phe Lys Asn Gly Val Leu Tyr Arg Glu Lys Asn Asn Gly Ile
                85                  90                  95

Asn Pro Ile Ala Glu Leu Ser Gln Leu Lys Phe Lys Gln Pro Lys Asp
            100                 105                 110

Lys Gln Tyr Ile Glu Ile Phe Leu Ala Ala Gln Gly Lys Glu Gly Asp
        115                 120                 125

Asp Ile Ile Ile Lys Thr Lys Ala Thr Pro Phe Gly Leu Trp Val Asn
    130                 135                 140

<210> SEQ ID NO 33
<211> LENGTH: 128
<212> TYPE: PRT
<213> ORGANISM: Thermacetogenium phaeum

<400> SEQUENCE: 33

Phe Thr Met Ile Glu Met Met Val Val Leu Ile Ile Ile Ala Val Leu
1               5                   10                  15

Ile Ala Gly Gly Ile Arg Phe Tyr Leu Gly Tyr Val Glu Arg Ala Lys
            20                  25                  30

Val Thr Lys Ala Lys Ser Glu Ile Thr Thr Met Gln Ala Ala Leu Asp
        35                  40                  45

Ser Tyr Tyr Ala Glu Lys Gly Glu Tyr Pro Asp Asp Glu Asn Asp Arg
    50                  55                  60

Glu Leu Val Lys Ala Gly Leu Ala Thr Asp Arg Ile Ser Ile Ser Thr
65                  70                  75                  80

Glu Gly Asn Asp Ser Ile Gln Tyr Ile Tyr Glu Gly Gly Asn Ser
                85                  90                  95

Tyr Lys Ile Ile Thr Thr Ala Thr Phe Arg Ala Gly Lys Leu Val Gly
            100                 105                 110

Glu Gly Gln Asp Gly Lys Ser Thr Glu Pro Asp Phe Gly Ser Gly Glu
        115                 120                 125

<210> SEQ ID NO 34
<211> LENGTH: 11
<212> TYPE: PRT
<213> ORGANISM: Artificial Sequence
```

```
<220> FEATURE:
<223> OTHER INFORMATION: peptide tag

<400> SEQUENCE: 34

Gly Pro Leu Gly Val Arg Gly Lys Gly Gly Cys
1               5                   10

<210> SEQ ID NO 35
<211> LENGTH: 11
<212> TYPE: PRT
<213> ORGANISM: Artificial Sequence
<220> FEATURE:
<223> OTHER INFORMATION: peptide tag

<400> SEQUENCE: 35

Cys Glu His Ser Ser Lys Leu Gln Leu Ala Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: peptide tag

<400> SEQUENCE: 36

Cys Ala Thr Ala Cys Ala Cys Cys Thr Cys Cys Ala Gly Cys
1               5                   10

<210> SEQ ID NO 37
<211> LENGTH: 11
<212> TYPE: PRT
<213> ORGANISM: Artificial Sequence
<220> FEATURE:
<223> OTHER INFORMATION: peptide tag

<400> SEQUENCE: 37

Leu Thr Pro Leu Gly Gly Gly Gly Gly Gly Cys
1               5                   10

<210> SEQ ID NO 38
<211> LENGTH: 14
<212> TYPE: PRT
<213> ORGANISM: Artificial Sequence
<220> FEATURE:
<223> OTHER INFORMATION: peptide tag

<400> SEQUENCE: 38

Lys Lys Lys Arg Pro Leu Ala Leu Trp Arg Ser Cys Cys Cys
1               5                   10

<210> SEQ ID NO 39
<211> LENGTH: 4
<212> TYPE: PRT
<213> ORGANISM: Artificial Sequence
<220> FEATURE:
<223> OTHER INFORMATION: peptide tag

<400> SEQUENCE: 39

Asp Glu Val Asp
1

<210> SEQ ID NO 40
<211> LENGTH: 12
<212> TYPE: PRT
<213> ORGANISM: Artificial Sequence
<220> FEATURE:
```

<223> OTHER INFORMATION: peptide tag

<400> SEQUENCE: 40

Glu Lys Glu Lys Glu Lys Glu Pro Pro Pro Cys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: peptide tag

<400> SEQUENCE: 41

Pro Pro Leu Arg Ile Asn Arg His Ile Leu Thr Arg
1               5                   10

<210> SEQ ID NO 42
<211> LENGTH: 9
<212> TYPE: PRT
<213> ORGANISM: Artificial Sequence
<220> FEATURE:
<223> OTHER INFORMATION: peptide tag

<400> SEQUENCE: 42

Tyr Pro Tyr Asp Val Pro Asp Tyr Ala
1               5

<210> SEQ ID NO 43

<400> SEQUENCE: 43

000

<210> SEQ ID NO 44
<211> LENGTH: 8
<212> TYPE: PRT
<213> ORGANISM: Artificial Sequence
<220> FEATURE:
<223> OTHER INFORMATION: peptide tag

<400> SEQUENCE: 44

Cys His Ser Ser Leu Lys Gln Lys
1               5

<210> SEQ ID NO 45

<400> SEQUENCE: 45

000

<210> SEQ ID NO 46
<211> LENGTH: 11
<212> TYPE: PRT
<213> ORGANISM: Artificial Sequence
<220> FEATURE:
<223> OTHER INFORMATION: peptide tag

<400> SEQUENCE: 46

Arg Pro Leu Ala Leu Trp Arg Ser Cys Cys Cys
1               5                   10

<210> SEQ ID NO 47
<211> LENGTH: 28
<212> TYPE: PRT
<213> ORGANISM: Artificial Sequence
<220> FEATURE:

```
<223> OTHER INFORMATION: peptide tag

<400> SEQUENCE: 47

Gln Ser Pro Ser Tyr Pro Asp Arg Glu Tyr Ser Asp Glu Asp Arg Gln
1               5                   10                  15

Ile Lys Gln Met Leu His Gln Glu Cys Pro Arg Leu
            20                  25

<210> SEQ ID NO 48
<211> LENGTH: 9
<212> TYPE: PRT
<213> ORGANISM: Artificial Sequence
<220> FEATURE:
<223> OTHER INFORMATION: peptide tag

<400> SEQUENCE: 48

Cys Thr Asn Thr Leu Ser Asn Asn Cys
1               5

<210> SEQ ID NO 49
<211> LENGTH: 7
<212> TYPE: PRT
<213> ORGANISM: Artificial Sequence
<220> FEATURE:
<223> OTHER INFORMATION: peptide tag

<400> SEQUENCE: 49

Glu Lys Glu Lys Glu Lys Glu
1               5

<210> SEQ ID NO 50
<211> LENGTH: 11
<212> TYPE: PRT
<213> ORGANISM: Artificial Sequence
<220> FEATURE:
<223> OTHER INFORMATION: peptide tag

<400> SEQUENCE: 50

Gly Pro Leu Gly Val Arg Gly Lys Gly Gly Cys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: peptide tag

<400> SEQUENCE: 51

Lys Lys Lys Arg Pro Leu Ala Leu Trp Arg Ser Cys Cys Cys
1               5                   10

<210> SEQ ID NO 52
<211> LENGTH: 8
<212> TYPE: PRT
<213> ORGANISM: Artificial Sequence
<220> FEATURE:
<223> OTHER INFORMATION: peptide tag

<400> SEQUENCE: 52

Asn Cys Gly Ala Ile Thr Ile Gly
1               5

<210> SEQ ID NO 53
<211> LENGTH: 8
<212> TYPE: PRT
```

```
<213> ORGANISM: Artificial Sequence
<220> FEATURE:
<223> OTHER INFORMATION: peptide tag

<400> SEQUENCE: 53

Asn Asn Phe Gln Gly Ala Ala Cys
1               5

<210> SEQ ID NO 54
<211> LENGTH: 4
<212> TYPE: PRT
<213> ORGANISM: Artificial Sequence
<220> FEATURE:
<223> OTHER INFORMATION: peptide tag

<400> SEQUENCE: 54

Phe Leu Asp Gln
1

<210> SEQ ID NO 55
<211> LENGTH: 4
<212> TYPE: PRT
<213> ORGANISM: Artificial Sequence
<220> FEATURE:
<223> OTHER INFORMATION: peptide tag

<400> SEQUENCE: 55

Glu Tyr Tyr Tyr
1

<210> SEQ ID NO 56
<211> LENGTH: 7
<212> TYPE: PRT
<213> ORGANISM: Artificial Sequence
<220> FEATURE:
<223> OTHER INFORMATION: peptide tag

<400> SEQUENCE: 56

Ala Ser Ser Leu Asn Ile Ala
1               5

<210> SEQ ID NO 57
<211> LENGTH: 9
<212> TYPE: PRT
<213> ORGANISM: Artificial Sequence
<220> FEATURE:
<223> OTHER INFORMATION: peptide tag

<400> SEQUENCE: 57

Gln Arg Lys Leu Ala Ala Lys Leu Thr
1               5

<210> SEQ ID NO 58
<211> LENGTH: 17
<212> TYPE: PRT
<213> ORGANISM: Artificial Sequence
<220> FEATURE:
<223> OTHER INFORMATION: peptide tag

<400> SEQUENCE: 58

His Lys His Ala His Asn Tyr Arg Leu Pro Ala Ser Gly Gly Gly Lys
1               5                   10                  15

Lys

<210> SEQ ID NO 59
<211> LENGTH: 12
```

```
<212> TYPE: PRT
<213> ORGANISM: Artificial Sequence
<220> FEATURE:
<223> OTHER INFORMATION: peptide tag

<400> SEQUENCE: 59

Phe Tyr Ser His Ser Phe His Glu Asn Trp Pro Ser
1               5                   10

<210> SEQ ID NO 60
<211> LENGTH: 11
<212> TYPE: PRT
<213> ORGANISM: Artificial Sequence
<220> FEATURE:
<223> OTHER INFORMATION: peptide tag

<400> SEQUENCE: 60

Ser Ile Phe Pro Leu Cys Asn Ser Gly Ala Leu
1               5                   10

<210> SEQ ID NO 61
<211> LENGTH: 5
<212> TYPE: PRT
<213> ORGANISM: Artificial Sequence
<220> FEATURE:
<223> OTHER INFORMATION: peptide tag

<400> SEQUENCE: 61

His Ala Ser Tyr Ser
1               5

<210> SEQ ID NO 62
<211> LENGTH: 9
<212> TYPE: PRT
<213> ORGANISM: Artificial Sequence
<220> FEATURE:
<223> OTHER INFORMATION: peptide tag

<400> SEQUENCE: 62

Cys Asp Tyr Lys Asp Asp Asp Asp Lys
1               5

<210> SEQ ID NO 63
<211> LENGTH: 7
<212> TYPE: PRT
<213> ORGANISM: Artificial Sequence
<220> FEATURE:
<223> OTHER INFORMATION: peptide tag

<400> SEQUENCE: 63

His Cys Val Ala Arg Phe Pro
1               5

<210> SEQ ID NO 64
<211> LENGTH: 19
<212> TYPE: PRT
<213> ORGANISM: Artificial Sequence
<220> FEATURE:
<223> OTHER INFORMATION: peptide tag

<400> SEQUENCE: 64

Asp Ala Asx Cys Tyr Leu Ser Gln Asn Tyr Pro Ile Val Gln Glu Asp
1               5                   10                  15

Ala Asn Ser

<210> SEQ ID NO 65
```

```
<211> LENGTH: 21
<212> TYPE: PRT
<213> ORGANISM: Artificial Sequence
<220> FEATURE:
<223> OTHER INFORMATION: peptide tag
<220> FEATURE:
<221> NAME/KEY: misc_feature
<222> LOCATION: (10)..(10)
<223> OTHER INFORMATION: Xaa can be any naturally occurring amino acid

<400> SEQUENCE: 65

Asp Ala Asx Cys Tyr Leu Gly Pro Ala Xaa Ala Ala Leu Ala Ile Gly
1               5                   10                  15

Glu Asp Ala Asn Ser
            20

<210> SEQ ID NO 66
<211> LENGTH: 8
<212> TYPE: PRT
<213> ORGANISM: Artificial Sequence
<220> FEATURE:
<223> OTHER INFORMATION: peptide tag

<400> SEQUENCE: 66

Ser Gly Asp Glu Val Asp Ser Gly
1               5

<210> SEQ ID NO 67
<211> LENGTH: 9
<212> TYPE: PRT
<213> ORGANISM: Artificial Sequence
<220> FEATURE:
<223> OTHER INFORMATION: peptide tag

<400> SEQUENCE: 67

Arg Pro Leu Ala Leu Trp Arg Ser Cys
1               5

<210> SEQ ID NO 68
<211> LENGTH: 4
<212> TYPE: PRT
<213> ORGANISM: Artificial Sequence
<220> FEATURE:
<223> OTHER INFORMATION: peptide tag

<400> SEQUENCE: 68

Lys Thr Phe Lys
1

<210> SEQ ID NO 69
<211> LENGTH: 9
<212> TYPE: PRT
<213> ORGANISM: Artificial Sequence
<220> FEATURE:
<223> OTHER INFORMATION: peptide tag

<400> SEQUENCE: 69

Gly Asp Gly Asp Glu Val Asp Gly Cys
1               5

<210> SEQ ID NO 70
<211> LENGTH: 6
<212> TYPE: PRT
<213> ORGANISM: Artificial Sequence
<220> FEATURE:
<223> OTHER INFORMATION: peptide tag

<400> SEQUENCE: 70
```

Ala Met Phe Leu Glu Ala
1               5

<210> SEQ ID NO 71
<211> LENGTH: 4
<212> TYPE: PRT
<213> ORGANISM: Artificial Sequence
<220> FEATURE:
<223> OTHER INFORMATION: peptide tag

<400> SEQUENCE: 71

Tyr His Asn Asn
1

<210> SEQ ID NO 72
<211> LENGTH: 4
<212> TYPE: PRT
<213> ORGANISM: Artificial Sequence
<220> FEATURE:
<223> OTHER INFORMATION: peptide tag

<400> SEQUENCE: 72

Gln Tyr His His
1

<210> SEQ ID NO 73
<211> LENGTH: 9
<212> TYPE: PRT
<213> ORGANISM: Artificial Sequence
<220> FEATURE:
<223> OTHER INFORMATION: peptide tag

<400> SEQUENCE: 73

Gly Pro Leu Gly Met Trp Ser Arg Cys
1               5

<210> SEQ ID NO 74
<211> LENGTH: 7
<212> TYPE: PRT
<213> ORGANISM: Artificial Sequence
<220> FEATURE:
<223> OTHER INFORMATION: peptide tag

<400> SEQUENCE: 74

Gly Arg Pro Ser Pro Glu Gly
1               5

<210> SEQ ID NO 75
<211> LENGTH: 10
<212> TYPE: PRT
<213> ORGANISM: Artificial Sequence
<220> FEATURE:
<223> OTHER INFORMATION: peptide tag

<400> SEQUENCE: 75

Arg Phe Ser Arg Pro Gln Leu Pro Glu Gly
1               5                   10

<210> SEQ ID NO 76
<211> LENGTH: 5
<212> TYPE: PRT
<213> ORGANISM: Artificial Sequence
<220> FEATURE:
<223> OTHER INFORMATION: peptide tag

<400> SEQUENCE: 76

Lys Thr Lys Thr Cys
1               5

<210> SEQ ID NO 77
<211> LENGTH: 12
<212> TYPE: PRT
<213> ORGANISM: Artificial Sequence
<220> FEATURE:
<223> OTHER INFORMATION: peptide tag

<400> SEQUENCE: 77

Tyr His Trp Tyr Gly Tyr Thr Pro Gln Asn Val Ile
1               5                   10

<210> SEQ ID NO 78
<211> LENGTH: 7
<212> TYPE: PRT
<213> ORGANISM: Artificial Sequence
<220> FEATURE:
<223> OTHER INFORMATION: peptide tag

<400> SEQUENCE: 78

His Ser Ser Lys Leu Gln Leu
1               5

<210> SEQ ID NO 79
<211> LENGTH: 9
<212> TYPE: PRT
<213> ORGANISM: Artificial Sequence
<220> FEATURE:
<223> OTHER INFORMATION: peptide tag

<400> SEQUENCE: 79

Arg Gly Thr Trp Glu Gly Lys Trp Lys
1               5

<210> SEQ ID NO 80
<211> LENGTH: 10
<212> TYPE: PRT
<213> ORGANISM: Artificial Sequence
<220> FEATURE:
<223> OTHER INFORMATION: peptide tag

<400> SEQUENCE: 80

Glu Ala Ala Glu Trp Asp Arg Val His Pro
1               5                   10

<210> SEQ ID NO 81
<211> LENGTH: 4
<212> TYPE: PRT
<213> ORGANISM: Artificial Sequence
<220> FEATURE:
<223> OTHER INFORMATION: peptide tag

<400> SEQUENCE: 81

Ala Ala Ala Asn
1

<210> SEQ ID NO 82
<211> LENGTH: 4
<212> TYPE: PRT
<213> ORGANISM: Artificial Sequence
<220> FEATURE:
<223> OTHER INFORMATION: peptide tag

<400> SEQUENCE: 82

Leu Arg Phe Gly

```
<210> SEQ ID NO 83
<211> LENGTH: 8
<212> TYPE: PRT
<213> ORGANISM: Artificial Sequence
<220> FEATURE:
<223> OTHER INFORMATION: peptide tag

<400> SEQUENCE: 83

Asp Asp Ala Gly Asn Arg Gln Pro
1               5

<210> SEQ ID NO 84
<211> LENGTH: 8
<212> TYPE: PRT
<213> ORGANISM: Artificial Sequence
<220> FEATURE:
<223> OTHER INFORMATION: peptide tag

<400> SEQUENCE: 84

Val Ser Gly Ser Ser Pro Asp Ser
1               5

<210> SEQ ID NO 85
<211> LENGTH: 12
<212> TYPE: PRT
<213> ORGANISM: Artificial Sequence
<220> FEATURE:
<223> OTHER INFORMATION: peptide tag

<400> SEQUENCE: 85

Leu Lys Ala His Leu Pro Pro Ser Arg Leu Pro Ser
1               5                   10

<210> SEQ ID NO 86
<211> LENGTH: 12
<212> TYPE: PRT
<213> ORGANISM: Artificial Sequence
<220> FEATURE:
<223> OTHER INFORMATION: peptide tag

<400> SEQUENCE: 86

Thr Gly Thr Ser Val Leu Ile Ala Thr Pro Tyr Val
1               5                   10

<210> SEQ ID NO 87
<211> LENGTH: 12
<212> TYPE: PRT
<213> ORGANISM: Artificial Sequence
<220> FEATURE:
<223> OTHER INFORMATION: peptide tag

<400> SEQUENCE: 87

Ala Tyr Ser Ser Gly Ala Pro Pro Met Pro Pro Phe
1               5                   10

<210> SEQ ID NO 88
<211> LENGTH: 12
<212> TYPE: PRT
<213> ORGANISM: Artificial Sequence
<220> FEATURE:
<223> OTHER INFORMATION: peptide tag

<400> SEQUENCE: 88

Ile Arg Pro Ala Ile His Ile Ile Pro Ile Ser His
1               5                   10
```

<210> SEQ ID NO 89
<211> LENGTH: 12
<212> TYPE: PRT
<213> ORGANISM: Artificial Sequence
<220> FEATURE:
<223> OTHER INFORMATION: peptide tag

<400> SEQUENCE: 89

Trp Ser Trp Arg Ser Pro Thr Pro His Val Val Thr
1               5                   10

<210> SEQ ID NO 90
<211> LENGTH: 12
<212> TYPE: PRT
<213> ORGANISM: Artificial Sequence
<220> FEATURE:
<223> OTHER INFORMATION: peptide tag

<400> SEQUENCE: 90

Met Ser Pro His Pro His Pro Arg His His His Thr
1               5                   10

<210> SEQ ID NO 91
<211> LENGTH: 12
<212> TYPE: PRT
<213> ORGANISM: Artificial Sequence
<220> FEATURE:
<223> OTHER INFORMATION: peptide tag

<400> SEQUENCE: 91

Arg Gly Arg Arg Arg Arg Leu Ser Cys Arg Leu Leu
1               5                   10

<210> SEQ ID NO 92
<211> LENGTH: 12
<212> TYPE: PRT
<213> ORGANISM: Artificial Sequence
<220> FEATURE:
<223> OTHER INFORMATION: peptide tag

<400> SEQUENCE: 92

Arg Leu Asn Pro Pro Ser Gln Met Asp Pro Pro Phe
1               5                   10

<210> SEQ ID NO 93
<211> LENGTH: 12
<212> TYPE: PRT
<213> ORGANISM: Artificial Sequence
<220> FEATURE:
<223> OTHER INFORMATION: peptide tag

<400> SEQUENCE: 93

Gln Thr Trp Pro Pro Pro Leu Trp Phe Ser Thr Ser
1               5                   10

<210> SEQ ID NO 94
<211> LENGTH: 12
<212> TYPE: PRT
<213> ORGANISM: Artificial Sequence
<220> FEATURE:
<223> OTHER INFORMATION: peptide tag

<400> SEQUENCE: 94

His Pro Pro Met Asn Ala Ser His Pro His Met His
1               5                   10

<210> SEQ ID NO 95
<211> LENGTH: 12
<212> TYPE: PRT
<213> ORGANISM: Artificial Sequence
<220> FEATURE:
<223> OTHER INFORMATION: peptide tag

<400> SEQUENCE: 95

His Thr Lys His Ser His Thr Ser Pro Pro Pro Leu
1               5                   10

<210> SEQ ID NO 96
<211> LENGTH: 9
<212> TYPE: PRT
<213> ORGANISM: Artificial Sequence
<220> FEATURE:
<223> OTHER INFORMATION: peptide tag

<400> SEQUENCE: 96

Cys His Lys Lys Pro Ser Lys Ser Cys
1               5

<210> SEQ ID NO 97
<211> LENGTH: 12
<212> TYPE: PRT
<213> ORGANISM: Artificial Sequence
<220> FEATURE:
<223> OTHER INFORMATION: peptide tag

<400> SEQUENCE: 97

Arg Lys Leu Pro Asp Ala Pro Gly Met His Thr Trp
1               5                   10

<210> SEQ ID NO 98
<211> LENGTH: 12
<212> TYPE: PRT
<213> ORGANISM: Artificial Sequence
<220> FEATURE:
<223> OTHER INFORMATION: peptide tag

<400> SEQUENCE: 98

Tyr Pro Ser Ala Pro Pro Gln Trp Leu Thr Asn Thr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: peptide tag

<400> SEQUENCE: 99

Ser Thr Pro Leu Val Thr Gly Thr Asn Asn Leu Met
1               5                   10

<210> SEQ ID NO 100
<211> LENGTH: 12
<212> TYPE: PRT
<213> ORGANISM: Artificial Sequence
<220> FEATURE:
<223> OTHER INFORMATION: peptide tag

<400> SEQUENCE: 100

Gln Ser Gly Ser His Val Thr Gly Asp Leu Arg Leu
1               5                   10

```
<210> SEQ ID NO 101
<211> LENGTH: 12
<212> TYPE: PRT
<213> ORGANISM: Artificial Sequence
<220> FEATURE:
<223> OTHER INFORMATION: peptide tag

<400> SEQUENCE: 101

Ala Thr Thr Leu His Pro Pro Arg Thr Ser Leu Pro
1               5                   10

<210> SEQ ID NO 102
<211> LENGTH: 19
<212> TYPE: PRT
<213> ORGANISM: Artificial Sequence
<220> FEATURE:
<223> OTHER INFORMATION: peptide tag

<400> SEQUENCE: 102

Ser Cys Ser Asp Cys Leu Lys Ser Val Asp Phe Ile Pro Ser Ser Leu
1               5                   10                  15

Ala Ser Ser

<210> SEQ ID NO 103
<211> LENGTH: 12
<212> TYPE: PRT
<213> ORGANISM: Artificial Sequence
<220> FEATURE:
<223> OTHER INFORMATION: peptide tag

<400> SEQUENCE: 103

Leu Asn Ala Ala Val Pro Phe Thr Met Ala Gly Ser
1               5                   10

<210> SEQ ID NO 104
<211> LENGTH: 7
<212> TYPE: PRT
<213> ORGANISM: Artificial Sequence
<220> FEATURE:
<223> OTHER INFORMATION: peptide tag

<400> SEQUENCE: 104

Ala Thr Trp Val Ser Pro Tyr
1               5

<210> SEQ ID NO 105
<211> LENGTH: 16
<212> TYPE: PRT
<213> ORGANISM: Artificial Sequence
<220> FEATURE:
<223> OTHER INFORMATION: peptide tag

<400> SEQUENCE: 105

Arg Lys Lys Arg Thr Lys Asn Pro Thr His Lys Leu Gly Gly Gly Trp
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: peptide tag

<400> SEQUENCE: 106

Lys Ser Leu Ser Arg His Asp His Ile His His His Gly Gly Gly Trp
1               5                   10                  15
```

<210> SEQ ID NO 107
<211> LENGTH: 16
<212> TYPE: PRT
<213> ORGANISM: Artificial Sequence
<220> FEATURE:
<223> OTHER INFORMATION: peptide tag

<400> SEQUENCE: 107

Thr Gln His Leu Ser His Pro Arg Tyr Ala Thr Lys Gly Gly Gly Trp
1               5                   10                  15

<210> SEQ ID NO 108
<211> LENGTH: 12
<212> TYPE: PRT
<213> ORGANISM: Artificial Sequence
<220> FEATURE:
<223> OTHER INFORMATION: peptide tag

<400> SEQUENCE: 108

Glu Ala His Val Met His Lys Val Ala Pro Arg Pro
1               5                   10

<210> SEQ ID NO 109
<211> LENGTH: 12
<212> TYPE: PRT
<213> ORGANISM: Artificial Sequence
<220> FEATURE:
<223> OTHER INFORMATION: peptide tag

<400> SEQUENCE: 109

Gly Leu His Val Met His Leu Val Ala Pro Pro Arg
1               5                   10

<210> SEQ ID NO 110
<211> LENGTH: 12
<212> TYPE: PRT
<213> ORGANISM: Artificial Sequence
<220> FEATURE:
<223> OTHER INFORMATION: peptide tag

<400> SEQUENCE: 110

Val Arg Thr Arg Asp Asp Ala Arg Thr His Arg Lys
1               5                   10

<210> SEQ ID NO 111
<211> LENGTH: 8
<212> TYPE: PRT
<213> ORGANISM: Artificial Sequence
<220> FEATURE:
<223> OTHER INFORMATION: peptide tag

<400> SEQUENCE: 111

Ala Gly Glu Thr Gln Gln Ala Met
1               5

<210> SEQ ID NO 112
<211> LENGTH: 12
<212> TYPE: PRT
<213> ORGANISM: Artificial Sequence
<220> FEATURE:
<223> OTHER INFORMATION: peptide tag

<400> SEQUENCE: 112

Leu Ser Thr Val Gln Thr Ile Ser Pro Ser Asn His
1               5                   10

```
<210> SEQ ID NO 113
<211> LENGTH: 12
<212> TYPE: PRT
<213> ORGANISM: Artificial Sequence
<220> FEATURE:
<223> OTHER INFORMATION: peptide tag

<400> SEQUENCE: 113

Thr Gly His Gln Ser Pro Gly Ala Tyr Ala Ala His
1               5                   10

<210> SEQ ID NO 114
<211> LENGTH: 12
<212> TYPE: PRT
<213> ORGANISM: Artificial Sequence
<220> FEATURE:
<223> OTHER INFORMATION: peptide tag

<400> SEQUENCE: 114

Ser Leu Lys Met Pro His Trp Pro His Leu Leu Pro
1               5                   10

<210> SEQ ID NO 115
<211> LENGTH: 9
<212> TYPE: PRT
<213> ORGANISM: Artificial Sequence
<220> FEATURE:
<223> OTHER INFORMATION: peptide tag

<400> SEQUENCE: 115

Cys Pro Thr Ser Thr Gly Gln Ala Cys
1               5

<210> SEQ ID NO 116
<211> LENGTH: 9
<212> TYPE: PRT
<213> ORGANISM: Artificial Sequence
<220> FEATURE:
<223> OTHER INFORMATION: peptide tag

<400> SEQUENCE: 116

Cys Thr Leu His Val Ser Ser Tyr Cys
1               5

<210> SEQ ID NO 117
<211> LENGTH: 7
<212> TYPE: PRT
<213> ORGANISM: Artificial Sequence
<220> FEATURE:
<223> OTHER INFORMATION: peptide tag

<400> SEQUENCE: 117

Gln Gln Ser Trp Pro Ile Ser
1               5

<210> SEQ ID NO 118
<211> LENGTH: 12
<212> TYPE: PRT
<213> ORGANISM: Artificial Sequence
<220> FEATURE:
<223> OTHER INFORMATION: peptide tag

<400> SEQUENCE: 118

Asn Phe Met Ser Leu Pro Arg Leu Gly His Met His
1               5                   10

<210> SEQ ID NO 119
```

```
<211> LENGTH: 7
<212> TYPE: PRT
<213> ORGANISM: Artificial Sequence
<220> FEATURE:
<223> OTHER INFORMATION: peptide tag

<400> SEQUENCE: 119

Ser Val Thr Gln Asn Lys Tyr
1               5

<210> SEQ ID NO 120
<211> LENGTH: 7
<212> TYPE: PRT
<213> ORGANISM: Artificial Sequence
<220> FEATURE:
<223> OTHER INFORMATION: peptide tag

<400> SEQUENCE: 120

Ser Pro His Pro Gly Pro Tyr
1               5

<210> SEQ ID NO 121
<211> LENGTH: 7
<212> TYPE: PRT
<213> ORGANISM: Artificial Sequence
<220> FEATURE:
<223> OTHER INFORMATION: peptide tag

<400> SEQUENCE: 121

His Ala Pro Thr Pro Met Leu
1               5

<210> SEQ ID NO 122
<211> LENGTH: 12
<212> TYPE: PRT
<213> ORGANISM: Artificial Sequence
<220> FEATURE:
<223> OTHER INFORMATION: peptide tag

<400> SEQUENCE: 122

Val Pro Ser Ser Gly Pro Gln Asp Thr Arg Thr Thr
1               5                   10

<210> SEQ ID NO 123
<211> LENGTH: 12
<212> TYPE: PRT
<213> ORGANISM: Artificial Sequence
<220> FEATURE:
<223> OTHER INFORMATION: peptide tag

<400> SEQUENCE: 123

Tyr Ser Pro Asp Pro Arg Pro Trp Ser Ser Arg Tyr
1               5                   10

<210> SEQ ID NO 124
<211> LENGTH: 12
<212> TYPE: PRT
<213> ORGANISM: Artificial Sequence
<220> FEATURE:
<223> OTHER INFORMATION: peptide tag

<400> SEQUENCE: 124

Met Thr Trp Asp Pro Ser Leu Ala Ser Pro Arg Ser
1               5                   10

<210> SEQ ID NO 125
<211> LENGTH: 12
```

```
<212> TYPE: PRT
<213> ORGANISM: Artificial Sequence
<220> FEATURE:
<223> OTHER INFORMATION: peptide tag

<400> SEQUENCE: 125

Ala Thr Ile His Asp Ala Phe Tyr Ser Ala Pro Glu
1               5                   10

<210> SEQ ID NO 126
<211> LENGTH: 12
<212> TYPE: PRT
<213> ORGANISM: Artificial Sequence
<220> FEATURE:
<223> OTHER INFORMATION: peptide tag

<400> SEQUENCE: 126

Asn Leu Asn Pro Asn Thr Ala Ser Ala Met His Val
1               5                   10

<210> SEQ ID NO 127
<211> LENGTH: 12
<212> TYPE: PRT
<213> ORGANISM: Artificial Sequence
<220> FEATURE:
<223> OTHER INFORMATION: peptide tag

<400> SEQUENCE: 127

His Asn Lys His Leu Pro Ser Thr Gln Pro Leu Ala
1               5                   10

<210> SEQ ID NO 128
<211> LENGTH: 12
<212> TYPE: PRT
<213> ORGANISM: Artificial Sequence
<220> FEATURE:
<223> OTHER INFORMATION: peptide tag

<400> SEQUENCE: 128

Ser Val Ser Val Gly Met Lys Pro Ser Pro Arg Pro
1               5                   10

<210> SEQ ID NO 129
<211> LENGTH: 12
<212> TYPE: PRT
<213> ORGANISM: Artificial Sequence
<220> FEATURE:
<223> OTHER INFORMATION: peptide tag

<400> SEQUENCE: 129

Val Ile Ser Asn His Arg Glu Ser Ser Arg Pro Leu
1               5                   10

<210> SEQ ID NO 130
<211> LENGTH: 12
<212> TYPE: PRT
<213> ORGANISM: Artificial Sequence
<220> FEATURE:
<223> OTHER INFORMATION: peptide tag

<400> SEQUENCE: 130

His Ser Val Arg Trp Leu Leu Pro Gly Ala His Pro
1               5                   10

<210> SEQ ID NO 131
<211> LENGTH: 12
<212> TYPE: PRT
```

```
<213> ORGANISM: Artificial Sequence
<220> FEATURE:
<223> OTHER INFORMATION: peptide tag

<400> SEQUENCE: 131

Lys Leu His Ser Ser Pro His Thr Leu Pro Val Gln
1               5                   10

<210> SEQ ID NO 132
<211> LENGTH: 12
<212> TYPE: PRT
<213> ORGANISM: Artificial Sequence
<220> FEATURE:
<223> OTHER INFORMATION: peptide tag

<400> SEQUENCE: 132

Ser Val Ser Val Gly Met Lys Pro Ser Pro Arg Pro
1               5                   10

<210> SEQ ID NO 133
<211> LENGTH: 9
<212> TYPE: PRT
<213> ORGANISM: Artificial Sequence
<220> FEATURE:
<223> OTHER INFORMATION: peptide tag

<400> SEQUENCE: 133

Cys Met Leu Pro His His Gly Ala Cys
1               5

<210> SEQ ID NO 134
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 134
ctaggtaccg tggtggaccc ccttaccggt                                      30

<210> SEQ ID NO 135
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 135
cgaactagtt gtgaccgctg ccggctccg                                       29

<210> SEQ ID NO 136
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 136
cacgcggccg caagaggagc cagtgacgaa aatc                                 34

<210> SEQ ID NO 137
<211> LENGTH: 48
<212> TYPE: DNA
<213> ORGANISM: Artificial Sequence
<220> FEATURE:
<223> OTHER INFORMATION: oligonucleotide primer
```

<400> SEQUENCE: 137
gagttagtgg tggtggtggt ggtgactttc gggcggatag gtttgatc        48

<210> SEQ ID NO 138
<211> LENGTH: 42
<212> TYPE: DNA
<213> ORGANISM: Artificial Sequence
<220> FEATURE:
<223> OTHER INFORMATION: oligonucleotide primer

<400> SEQUENCE: 138
ctccagtatg tatttaatca attagtggtg gtggtggtgg tg              42

<210> SEQ ID NO 139
<211> LENGTH: 42
<212> TYPE: DNA
<213> ORGANISM: Artificial Sequence
<220> FEATURE:
<223> OTHER INFORMATION: oligonucleotide primer

<400> SEQUENCE: 139
caccaccacc accaccacta attgattaaa tacatactgg ag              42

<210> SEQ ID NO 140
<211> LENGTH: 40
<212> TYPE: DNA
<213> ORGANISM: Artificial Sequence
<220> FEATURE:
<223> OTHER INFORMATION: oligonucleotide primer

<400> SEQUENCE: 140
ctgctcgagg atacctaggc tattccgaca actacgagac                 40

<210> SEQ ID NO 141
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 141
catcctagga gggcagacat tgcggaacgt                            30

<210> SEQ ID NO 142
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 142
catctcgagc gggttccgct gccgtcgtac                            30

<210> SEQ ID NO 143
<211> LENGTH: 58
<212> TYPE: DNA
<213> ORGANISM: Artificial Sequence
<220> FEATURE:
<223> OTHER INFORMATION: oligonucleotide primer

<400> SEQUENCE: 143
gtatttaatc aattacgcgt agtccggcac gtcgtacggg taactttcgg gcggatag    58

<210> SEQ ID NO 144
<211> LENGTH: 58

```
<212> TYPE: DNA
<213> ORGANISM: Artificial Sequence
<220> FEATURE:
<223> OTHER INFORMATION: oligonucleotide primer

<400> SEQUENCE: 144
ctatccgccc gaaagttacc cgtacgacgt gccggactac gcgtaattga ttaaatac      58

<210> SEQ ID NO 145
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 145
tctgaattcc gatatgacta ctgcgac                                        27

<210> SEQ ID NO 146
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 146
tctgaattcc gatatgacta ctgcgac                                        27

<210> SEQ ID NO 147
<211> LENGTH: 14
<212> TYPE: PRT
<213> ORGANISM: Artificial Sequence
<220> FEATURE:
<223> OTHER INFORMATION: PilA peptide

<400> SEQUENCE: 147

Glu Ser Ala Phe Ala Asp Asp Gln Thr Tyr Pro Pro Glu Ser
1               5                   10

<210> SEQ ID NO 148
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 148
tctggatcca ggaggagaca cttatgcttc agaaac                              36

<210> SEQ ID NO 149
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 149
tctggatcca ggaggagaca cttatgcttc agaaac                              36
```